United States Patent [19]

Ring

[11] Patent Number: 6,054,561
[45] Date of Patent: *Apr. 25, 2000

[54] ANTIGEN-BINDING SITES OF ANTIBODY MOLECULES SPECIFIC FOR CANCER ANTIGENS

[75] Inventor: David B. Ring, Palo Alto, Calif.

[73] Assignee: Chiron Corporation, Emeryville, Calif.

[*] Notice: This patent is subject to a terminal disclaimer.

[21] Appl. No.: 08/483,749

[22] Filed: Jun. 7, 1995

Related U.S. Application Data

[63] Continuation-in-part of application No. 08/288,981, Aug. 11, 1994, Pat. No. 5,629,197, which is a continuation of application No. 07/190,778, May 8, 1988, Pat. No. 5,169,774, which is a continuation of application No. 06/842,476, Mar. 21, 1986, abandoned, which is a continuation-in-part of application No. 06/690,750, Jan. 11, 1985, Pat. No. 4,753,894, which is a continuation-in-part of application No. 06/577,976, Feb. 8, 1984, abandoned.

[51] Int. Cl.$^7$ .......................... C07K 16/18; C07K 16/28; C07K 16/30; C07K 16/32
[52] U.S. Cl. .................... 530/388.1; 530/388.2; 530/388.22; 530/388.8; 530/395
[58] Field of Search .............................. 530/388.1, 388.2, 530/388.22, 388.8, 395

[56] References Cited

U.S. PATENT DOCUMENTS

| | | |
|---|---|---|
| Re. 35,491 | 4/1997 | Cline et al. . |
| 4,753,894 | 6/1988 | Frankel et al. . |
| 4,938,948 | 7/1990 | Ring et al. .................................. 424/9 |
| 4,946,778 | 8/1990 | Ladner et al. .......................... 435/69.6 |
| 5,169,774 | 12/1992 | Frankel et al. . |
| 5,585,089 | 12/1996 | Queen et al. ......................... 424/133.1 |
| 5,629,197 | 5/1997 | Ring et al. . |
| 5,677,171 | 10/1997 | Hudziak et al. . |
| 5,720,937 | 2/1998 | Hudziak et al. . |
| 5,720,954 | 2/1998 | Hudziak et al. . |
| 5,725,856 | 3/1998 | Hudziak et al. . |
| 5,770,195 | 6/1998 | Hudziak et al. . |
| 5,772,997 | 6/1998 | Hudziak et al. . |

FOREIGN PATENT DOCUMENTS

| | | |
|---|---|---|
| 0 519 596 A1 | 12/1992 | European Pat. Off. . |
| 62-108157 | 5/1987 | Japan . |
| 2 276 169 | 9/1994 | United Kingdom . |
| 91/09967 | 11/1991 | WIPO . |
| WO 92/22653 | 12/1992 | WIPO . |

OTHER PUBLICATIONS

Benkar, I et al. PMAS USA 91(25):12051–5, 1994.
Diegel, ML et al. AIDS Res. Human Retroviruses 9(5): 465–73, 1993.
Padlan, EA. Mol. Immunol. 28(4/5):489–498, 1991.
Huston et al., "Protein Engineering of Antibody Binding Sites: Recovery of Specific Activity in an Anti–digoxin Single–chain Fv Analogue Produced in *Escherichia coli*," *Proc. Natl. Acad. Sci.* (USA) (1988) 85:5879–5883.
Riechmann et al., "Reshaping Human Antibodies for Therapy," *Nature* (1988) 332:323–327.
Ring et al., "Identity of BCA200 and c–erbB–2 Indicated by Reactivity of Monoclonal Antibodies with Recombinant c–erbB–2," *Molecular Immunology* (1991) 28(8):915–917.
Verhoeyen et al., "Reshaping Human Antibodies: Grafting an Antilyxozyme Activity," *Science* (1988) 239:1534–1536.
Allen et al., "Microvillin: A 200–Kilodalton Protein in Microvilli of Rat Mammary Cells Detected by a Monoclonal Antibody," *Proc. Natl. Acad. Sci. USA* 81:5459–5463 (1984).
Carter et al., "Humanization of an Anti–p185$^{HER2}$ Antibody for Human Cancer Therapy," *Proc. Natl. Acad. Sci. USA* 89:4285–4289 (1992).
Cohen et al., "Expression Pattern on neu (NGL) Gene–Encoded Growth Factor Receptor Protein (p185$^{neu}$) in Normal and Transformed Epithelial Tissues of the Digestive Tract," *Oncogene* 4:81–88 (1989).
Colcher et al., "A Spectrum of Monoclonal Antibodies Reactive with Human Mammary Tumor Cells," *Proc. Natl. Acad. Sci USA* 3:3199–3203 (1981).
Drebin et al., "Monoclonal Antibodies Identify a Cell–Surface Antigen Associated With an Activated Cellular Oncogene," *Nature* 312:545–548 (1984).
Drebin et al., "Down–Modulation of an Oncogene Protein Product and Reversion of the Transformed Phenotype by Monoclonal Antibodies," *Cell* 41:695–706 (1985).
Drebin et al., "Development of Monoclonal Antibodies Reactive with the Product of the neu Oncogene," *Immunology and Cancer* (Kripke et al., eds., the University of Texas Press, Austin) vol. 38, Chapter 18, pp. 277–289 (1986).
Fendly et al., "Characterization of Murine Monoclonal Antibodies Reactive to Either the Human Epidermal Growth Factor Receptor or HER2/neu Gene Product," *Cancer Research* 50:1550–1558 (1990).

(List continued on next page.)

*Primary Examiner*—Paula K. Hutzell
*Assistant Examiner*—Geetha P. Bansal
*Attorney, Agent, or Firm*—Roberta L. Robins; Joseph H. Guth; Robert P. Blackburn

[57] ABSTRACT

Novel compositions are provided that are derived from antigen-binding sites of immunoglobulins having affinity for cancer antigens. The compositions exhibit immunological binding properties of antibody molecules capable of binding specifically to a human tumor cell expressing an antigen selected from the group consisting of high molecular weight mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. A number of synthetic molecules are provided that include CDR and FR regions derived from same or different immunoglobulin moieties. Also provided are single chain polypeptides wherein $V_H$ and $V_L$ domains are attached by a single polypeptide linker. The sFv molecules can include ancillary polypeptide moieties which can be bioactive, or which provide a site of attachment for other useful moieties. The compositions are useful in specific binding assays, affinity purification schemes, drug or toxin targeting, imaging, and genetic or immunological therapeutics for various cancers. The invention thus provides novel polypeptides, the DNAs encoding those polypeptides, expression cassettes comprising those DNAs, and methods of inducing the production of the polypeptides.

31 Claims, 14 Drawing Sheets

OTHER PUBLICATIONS

Gullick et al., "Expression of the c–erbB–2 Protein in Normal and Transformed Cells," *Int. J. Cancer* 40:246–254 (1987).

Hand et al., "Definition of Antigenic Heterogeneity and Modulation Among Human Mammary Carcinoma Cell Populations Using Monoclonal Antibodies to Tumor–Associated Antigens," *Cancer Research* 43:728–735 (1983).

Hudziak et al.; "p185$^{HER2}$ Monoclonal Antibody Has Antiproliferative Effects In Vitro and Sensitizes Human Breast Tumor Cells to Tumor Necrosis Factor," *Molecular and Cellular Biology* 9(3):1165–1172 (1989).

Kennel et al., "Direct Binding of Radioiodinated Monoclonal Antibody to Tumor Cells: Significance of Antibody Purity and Affinity for Drug Targeting or Tumor Imaging," *Hybridoma* 2(3):297–310 (1983).

Kennel et al., "Tumor Antigen on Benign Adenomas and on Murine Lung Carcinomas Quantitated by a Two–Site Monoclonal Antibody Assay," *Cancer Research* 46:707–712 (1986).

Loop et al., "Two Human Tumor–Associated Antigens, p155 and p210, Detected by Monoclonal Antibodies," *Int. J. Cancer* 27:775–781 (1981).

Padhy et al., "Identification of a Phosphoprotein Specifically Induced by the Transforming DNA of Rat Neuroblastomas," *Cell* 28:865–871 (1982).

Ring et al., "Distribution and Physical Properties of BCA200, a $M_r$ 200,000 Glycoprotein Selectively Associated with Human Breast Cancer," *Cancer Research* 49:3070–3080 (1989).

Ring et al., "Identity of BCA200 and c–erbB–2 Indicated by Reactivity of Monoclonal Antibodies with Recombinant c–erbB–2," *Molecular Immunology* 28(8):915–917 (1991).

Schechter et al., "The neu Oncogene: an erb–B–related Gene Encoding a 185,000–$M_r$ Tumour Antigen," *Nature* 312:513–516 (1984).

Stramignoni et al., "Differential Reactivity of Monoclonal Antibodies with Human Colon Adenocarcinomas and Adenomas," *J. Cancer* 31:543–552 (1983).

2G3 HC

```
  1  GAA GTG AAG CTT GAG GAG TCT GGA GGA GGC TTG GTG CAA CCT GGA
     E   V   K   L   E   E   S   G   G   G   L   V   Q   P   G
     |------------------------------------------HFR1--------------

46  AGA TCC ATG AAA CTC TCC TGT GTT GCC TCT GGA TTC ACT TTC AGT
     R   S   M   K   L   S   C   V   A   S   G   F   T   F   S
     ----------------------------------------------------------|

91  AAC TAC TGG ATG AAC TGG GTC CGC CAG TCT CCA GAG AAG GGG CTT
     N   Y   W   M   N   W   V   R   Q   S   P   E   K   G   L
     |----HCDR1--------| |---------------HFR2--------------------

136  GAG TGG GTT GCT GAA ATT AGA TTG AAA TCT AAT AAT TAT GCA ACA
     E   W   V   A   E   I   R   L   K   S   N   N   Y   A   T
     ----------------| |-----------------------------HCDR2--------

181  CAT TAT GCG GAG TCT GTG AAA GGG AGG TTC ACC ATC TCA AGA GAT
     H   Y   A   E   S   V   K   G   R   F   T   I   S   R   D
     ------------------------------------| |-----------HFR3------

226  GAT TCC AAA AGT AGT GTC TAC CTG CAA CTG AAC AAC TTA AGA GCT
     D   S   K   S   S   V   Y   L   Q   L   N   N   L   R   A
     --------------------------------------------------------

271  GAA GAC ACT GGC ATT TAT TAC TGT GCC AGG GAG AGG TAC CTC TAT
     E   D   T   G   I   Y   Y   C   A   R   E   R   Y   L   Y
     ------------------------------------| |--------HCDR3--------

316  TAC TAT ACT ATG GAC TAC TGG GGT CAA GGA ACC TCA GTC ACA GTA
     Y   Y   T   M   D   Y   W   G   Q   G   T   S   V   T   V
     ------------------------| |-----------------HFR4------------

361  TCC TCG
     S   S
     ------|
```

```
  1  GAT ATT GTC ATG ACG CAA GCA GCA CCC TCT GTA CCT GTC ACT CCT
     D   I   V   M   T   Q   A   A   P   S   V   P   V   T   P
     |------------------------------------------LFR1---------------

46  GGA GAG TCA GTA TCC ATC TCC TGC AGG TCT AGT AAG AGT CTC CTG
     G   E   S   V   S   I   S   C   R   S   S   K   S   L   L
     ---------------------------------| |-------LCDR1--------------

91  CAT AGT AAT GGC AAC ACT TTC TTG TAT TGG TTC CTG CAG AGG CCA
     H   S   N   G   N   T   F   L   Y   W   F   L   Q   R   P
     --------------------------------| |-----------LFR2-------

136  GGC CAG TCT CCT CAG CTC CTG ATA TAT CGG ATG TCC AAC CTT GCC
     G   Q   S   P   Q   L   L   I   Y   R   M   S   N   L   A
     --------------------------------| |---------LCDR2---------

181  TCA GGA GTC CCA GAC AGG TTC AGT GGC AGT GGG TCA GGA ACT GCT
     S   G   V   P   D   R   F   S   G   S   G   S   G   T   A
     --| |-------------------------------------LFR3----------------

226  TTC ACA CTG AGA ATC AGT AGA GTG GAG GCT GAG GAT GTG GGT GTT
     F   T   L   R   I   S   R   V   E   A   E   D   V   G   V
     ---------------------------------------------------------

271  TAT TAC TGT ATG CAA TAT CTA GAA TAT CCT TTC ACG TTC GGC TCG
     Y   Y   C   M   Q   Y   L   E   Y   P   F   T   F   G   S
     -----------| |------------------LCDR3-------------| |---------

316  GGG ACA AAG TTG GAA ATC AAA
     G   T   K   L   E   I   K
     ----LFR4----------------|
```

```
  1  GAG GTG CAG CTG AAG GAG TCT GGG GGA GGC TTA GTG CAG CCT GGA
     E   V   Q   L   K   E   S   G   G   G   L   V   Q   P   G
     |---------------------HFR1-----------------------------------

46  GGG TCC CGG AAA CTC TCC TGT GCA GCC TCT GGA TTC ATT TTC AGT
     G   S   R   K   L   S   C   A   A   S   G   F   I   F   S
     ------------------------------------------------------------

91  AGC TAT GCC ATG TCT TGG GTC CGC CAG ACT CCG GAG AAG AGG CTG
     S   Y   A   M   S   W   V   R   Q   T   P   E   K   R   L
     |-----HCDR1-------| |----------------------HFR2-------------

136  GAG TGG GTC GCA GCC ATT AGT ACT GAT GGT AGT TTC ATC TTC TAC
     E   W   V   A   A   I   S   T   D   G   S   F   I   F   Y
     -----------------| |-----------------------HCDR2------------

181  CCA GAC ACT GTA AGA GGC CGA TTC ACC ATC TCC AGA GAC AAT GCC
     P   D   T   V   R   G   R   F   T   I   S   R   D   N   A
     ----------------------| |----------------------HFR3---------

226  AAG AAC ACC CTG TTT CTG CAA ATG AGC AGT CTA AGG TAT GAG GAC
     K   N   T   L   F   L   Q   M   S   S   L   R   Y   E   D
     ------------------------------------------------------------

271  ACG GCC ATG TAT TAC TGT TCT AGT *AC TAT GCT ATG GAC TAC TGG
     T   A   M   Y   Y   C   S   S   X   Y   A   M   D   Y   W
     -----------------------------| |-----------HCDR3------| |--

316  GAT CAA GGA ACC GCA GTC AAC GTC TCC TCA
     D   Q   G   T   A   V   N   V   S   S
     -----------------HFR4------------------|
```

```
  1 GAG CTC GTG CAC ACC CAG TCT CCA GCA ATC ATG TCT GCA TCT CCT
    E   L   V   H   T   Q   S   P   A   I   M   S   A   S   P
    |-----------------------------LFR1--------------------------
```

```
 46 GGG GAG AAG GTC GCC TTG ACC TGC AAT GCC AGC TCA AGT GTA AGT
    G   E   K   V   A   L   T   C   N   A   S   S   S   V   S
    --------------------------------| |----------------LCDR1----
```

```
 91 TCC AGC TAC TTG TAC TGG TAC CAG CAG AAG CCA GGA TCC TCC CCC
    S   S   Y   L   Y   W   Y   Q   Q   K   P   G   S   S   P
    --------------------| |----------------------------LFR2-----
```

```
136 AAA CTC TGG ATT TAT AGC ACA TCC AAC CTG GCT TCT GGA GTC CCT
    K   L   W   I   Y   S   T   S   N   L   A   S   G   V   P
    --------------------| |--------LCDR2------------| |---------
```

```
181 GCT CGC TTC AGT GGC CGT GGG TCT GGG ACC TCT TAC TCT CTC ACA
    A   R   F   S   G   R   G   S   G   T   S   Y   S   L   T
    -----------------------LFR3---------------------------------
```

```
226 ATC ACC AGC ATG GAG GCT GAA GAT GCT GCC TCT TAT TTC TGC CAT
    I   T   S   M   E   A   E   D   A   A   S   Y   F   C   H
    ------------------------------------------------------| |--
```

```
271 CAG TGG AGT AGT TTC CCA TTC ACG TTC GGC TCG GGA ACA AAG TTG
    Q   W   S   S   F   P   F   T   F   G   S   G   T   K   L
    ---------LCDR3-----------------| |--------------LFR4--------
```

```
316 GAA ATA AAA
    E   I   K
    ----------|
```

```
  1  GAG GTG AAA CTT GAG GAG TCT GGA GGA GGC TTG GTG CAA CCT GGA
     E   V   K   L   E   E   S   G   G   G   L   V   Q   P   G
     |--------------------------------------------------HFR1------------

46  GGA TCT ATG AAA CTC TCC TGT GTT GCC TCT GGA TTC ACT TTC AGT
     G   S   M   K   L   S   C   V   A   S   G   F   T   F   S
     --------------------------------------------------------------|

91  AAC TAT TGG ATG AAT TGG GTC CGC CAG TCT CCA GAG AAG GGG CTT
     N   Y   W   M   N   W   V   R   Q   S   P   E   K   G   L
     |------HCDR1------|  |-------------------HFR2----------------

136  GAG TGG GTC GCT GAA ATT AAA TTA AAA TCT AAT AAT TAT CCA ACA
     E   W   V   A   E   I   K   L   K   S   N   N   Y   P   T
     ---------------|  |--------------------HCDR2-----------------

181  CAT TAT GCG GAG TCT GTG AAA GGG AGG TTC ACC GCC TCA AGA GAT
     H   Y   A   E   S   V   K   G   R   F   T   A   S   R   D
     ----------------------------------|  |---------------HFR3-------

226  GAT TCC AAA AGT AGT ATC TAC CTG CAA ATG AAT AAC TTA AGA ACT
     D   S   K   S   S   I   Y   L   Q   M   N   N   L   R   T
     ----------------------------------------------------------------

271  GAA GAC ACT GGC ATT TAT TTC TGT ACG TTC TGG GAC TAT TGG GGC
     E   D   T   G   I   Y   F   C   T   F   W   D   Y   W   G
     -----------------------------------|  |--HCDR3--|  |------

316  CGA GGC ACC ACT CTC ACA GTC TCC TCG
     R   G   T   T   L   T   V   S   S
     ----------------HFR4----------------|
```

```
  1  GAT ATT CTC ATG ACC CAA TCT CCA TCC TCC ATG TCT GTG TCT CTG
      D   I   L   M   T   Q   S   P   S   S   M   S   V   S   L
     |---------------------------------------------LFR1---------------

46  GGA GAC ACA GTC AGC ATC ACT TGC CAT GCA AGT CAG GGC ATT GAC
      G   D   T   V   S   I   T   C   H   A   S   Q   G   I   D
     -------------------------------| |----------------LCDR1--------

91  AAG AAT ATT GGG TGG TTG CAG CAG AGA CCA GGG AAA TCA TTT AAG
      K   N   I   G   W   L   Q   Q   R   P   G   K   S   F   K
     ---------------| |------------------------------LFR2-----------

136  GGC CTG ATC TAT CTT GCA ACC AAC TTA GAA GAT GGA ATT CCA TCA
      G   L   I   Y   L   A   T   N   L   E   D   G   I   P   S
     ---------------| |----------LCDR2-------------| |-------------

181  AGG TTC AGT GGC AGT GGA TCT GGA GCA GAT TAT TCT CTC ACC ATC
      R   F   S   G   S   G   S   G   A   D   Y   S   L   T   I
     -----------------------------------LFR3-----------------------

226  ACC AGC CTG GAA TCT GAA GAT TTT GCA GAC TAT TAC TGT GTA CAG
      T   S   L   E   S   E   D   F   A   D   Y   Y   C   V   Q
     -----------------------------------------------------| |------

271  TAT GCT CAG TTT CCA TTC ACG TTC GGC TCG GGG ACA AAG TTG GAA
      Y   A   Q   F   P   F   T   F   S   G   S   T   K   L   E
     --------LCDR3--------------| |-----------------LFR4-----------

316  ATT AAA
      I   K
     ------|
```

```
  1  GAG GTG CAA CTG CAG GAG TCA GGA CCT GGC CTG GTG GCG CCC TCA
     E   V   Q   L   Q   E   S   G   P   G   L   V   A   P   S
     |-------------------------------------------HFR1-----------

46  CAG AGG CTG TCC ATC ACT TGC TCT GTC TCT GGG TTT TCA TTA ACC
     Q   R   L   S   I   T   C   S   V   S   G   F   S   L   T
     ---------------------------------------------------------|

91  AAC TAT GGT GTA CAC TGG GTT CGC CAG TCT CCA GGA AAG GGT CTA
     N   Y   G   V   H   W   V   R   Q   S   P   G   K   G   L
     |-----HCDR1-------| |----------------------------HFR2--------

136  GAG TGG CTG GGA GCA ATA TGG GCT GCT GGA AGC ACA AAT TAT AAT
     E   W   L   G   A   I   W   A   A   G   S   T   N   Y   N
     ---------------| |----------------HCDR2-----------------

181  TCG GCT CTC ATG TCC AGA CTG AGC ATC AGC AGA GAC AAC TCC AAG
     S   A   L   M   S   R   L   S   I   S   R   D   N   S   K
     ---------------| |----------------------------HFR3----------

226  AGC CAA GTT TTC TTA GAA ATG AAC GTT CTG CAA ACT GAT GAC ACA
     S   Q   V   F   L   E   M   N   V   L   Q   T   D   D   T
     -----------------------------------------------------------

271  GCC ATG TAC TAC TGT GCC AGA GAC GGG GAT TAC GAC TCT TAT ACT
     A   M   Y   Y   C   A   R   D   G   D   Y   D   S   Y   T
     -----------------------------| |----------HCDR3---------------

316  TTG GAC TAC TGG GGT CAA GGA ACC TCA GTC ACC GTC TCC TCA
     L   D   Y   W   G   Q   G   T   S   V   T   V   S   S
     ----------| |-------------------HFR4-------------------|
```

```
  1  GAG CTC GTA ATG ACA CAG TCT CCA TCC TCC CTA GCT GTG TCA GTT
      E   L   V   M   T   Q   S   P   S   S   L   A   V   S   V
      |---------------------------------------------------LFR1-----------

46  GGA GAG AAG GTT ACT ATG GGC TGC AAA TCC AGT CAG AGC CTT TTA
      G   E   K   V   T   M   G   C   K   S   S   Q   S   L   L
     --------------------------------| |-----------------LCDR1----

91  TAT AGT AGC AAT CAA AAG AAC TAC TTG GCC TGG TAC CAG CAG AAA
      Y   S   S   N   Q   K   N   Y   L   A   W   Y   Q   Q   K
     ---------------------------------------| |---------LFR2-----

136  CCA GGG CAG TCT CCT AAA CTG CTG ATT TAC TGG GCA TCC ACT AGG
      P   G   Q   S   P   K   L   L   I   Y   W   A   S   T   R
     ---------------------------------------| |-------LCDR2------

181  GAA TCT GGG GTC CCT GAT CGC TTC ACA GGC AGT GGA TCT GGG ACA
      E   S   G   V   P   D   R   F   T   G   S   G   S   G   T
     ------| |---------------------------LFR3--------------------

226  GAT TTC ACT CTC ACC ATC AGC AGT GTG AAG GCT GAA GAC CTG GCA
      D   F   T   L   T   I   S   S   V   K   A   E   D   L   A
     ------------------------------------------------------------

271  GTT TAT TAC TGT CAG CAA TAT TAT AGC TAT CCA TTC ACG TTC GGC
      V   Y   Y   C   Q   Q   Y   Y   S   Y   P   F   T   F   G
     ----------------| |-------------LCDR3----------------| |------

316  TCG GGG ACA AAG TTG GAA ATA AAA
      S   G   T   K   L   E   I   K
     -------LFR4---------------------|
```

```
  1  GAG GTT AAG CTT CTC GAG TCT GGA GGT GGC CTG GTG CAG CCT GGA
     E   V   K   L   L   E   S   G   G   G   L   V   Q   P   G
     |------------------------------HFR1-----------------

46  GGA TCC CTG AAA CTC TCC TGT GCA GCC TCA GGA TTC GAT TTT AGT
     G   S   L   K   L   S   C   A   A   S   G   F   D   F   S
     -----------------------------------------------------|

91  AGA TAC TGG ATG AGT TGG GTC CGG CAG GCT CCA GGG AAA GGG CTA
     R   Y   W   M   S   W   V   R   Q   A   P   G   K   G   L
     |----HCDR1--------|  |------------------------HFR2--------

136  GAA TGG ATT GGA GAA ATT AAT CCA GAT AGC AGT ACG ATA AAC TAT
     E   W   I   G   E   I   N   P   D   S   S   T   I   N   Y
     ---------------|  |------------------------HCDR2----------

181  ACG CCA TCT CTA AAG GAT AAA TTC ATC ATC TCC AGA GAC AAC GCC
     T   P   S   L   K   D   K   F   I   I   S   R   D   N   A
     ----------------------|  |------------------------HFR3-------

226  AAA AAT ACG CTG TAC CTG CAA ATG AGC GAA GTG AGA TCT GAG GAC
     K   N   T   L   Y   L   Q   M   S   E   V   R   S   E   D
     -----------------------------------------------------------

271  ACA GCC CTT TAT TAC TGT GCA AGA GGG GCG TAT ACT CTG GAC TAC
     T   A   L   Y   Y   C   A   R   G   A   Y   T   L   D   Y
     ----------------------------------|  |--------HCDR3------------|

316  TGG GGT CAA GGA ACC TCA GTC ACA GTA TCC TCG
     W   G   Q   G   T   S   V   T   V   S   S
     |---------------HFR4---------------------|
```

```
  1 GAT ATC GTG CTC ACA CAG TCT CCT GCT TCC TTA GCT GTA TCT CTG
    D   I   V   L   T   Q   S   P   A   S   L   A   V   S   L
    |-----------------------------------------------------LFR1----------

46 GGG CAG AGG GCC ACC ATC TCA TAC AGG GCC AGC AAA AGT GTC AGT
    G   Q   R   A   T   I   S   Y   R   A   S   K   S   V   S
    --------------------------------|  |---------------LCDR1------

91 ACA TCT GGC TAT AGT TAT ATG CAC TGG AAC CAA CAG AAA CCA GGA
    T   S   G   Y   S   Y   M   H   W   N   Q   Q   K   P   G
    --------------------------------|  |-----------LFR2----------

136 CAG CCA CCC AGA CTC CTC ATC TAT CTT GTA TCC AAC CTA GAA TCT
    Q   P   P   R   L   L   I   Y   L   V   S   N   L   E   S
    --------------------------------|  |----------LCDR2----------|

181 GGG GTC CCT GCC AGG TTC AGT GGC AGT GGG TCT GGG ACA GAC TTC
    G   V   P   A   R   F   S   G   S   G   S   G   T   D   F
    |-----------------------------------------LFR3---------------------

226 ACC CTC AAC ATC CAT CCT GTG GAG GAG GAG GAT GCT GCA ACC TAT
    T   L   N   I   H   P   V   E   E   E   D   A   A   T   Y
    ---------------------------------------------------------------

271 TAC TGT CAG CAC ATT AGG GAG *CT TAC ACG TTC GGA GGG GGG ACC
    Y   C   Q   H   I   R   E   X   Y   T   F   G   G   G   T
    ------|  |------------LCDR3--------------|  |----------LFR4----

316 AAG CTG GAA ATC AAA
    K   L   E   I   K
    -------------------|
```

```
  1  GAG CTC GTC ATG ACC CAG TCT CCA GCT TCT TTG GCT GTG TCT CTA
      E   L   V   M   T   Q   S   P   A   S   L   A   V   S   L
     |------------------------------------------------LFR1----------

46  GGG CAG AGG GCC ACC ATC TCC TGC AGA GCC AGC GAA ACT GTT GAT
      G   Q   R   A   T   I   S   C   R   A   S   E   T   V   D
     ---------------------------------| |--------------LCDR1-----

91  AAT TAT GGT ATT AGT TTC ATG AAC TGG TTC CAA CAG AAA CCA GGA
      N   Y   G   I   S   F   M   N   W   F   Q   Q   K   P   G
     ---------------------------------| |--------------LFR2--------

136  CAG CCA CCC CAA CTC CTC ATC TAT GAT GCT TCC AAC CAA GGA TCC
      Q   P   P   Q   L   L   I   Y   D   A   S   N   Q   G   S
     ---------------------------------| |----------LCDR2----------|

181  GGG GTC CCT GCC AGG TTT AGA GGC AGT GGG TCT GGG ACA GAC TTC
      G   V   P   A   R   F   R   G   S   G   S   G   T   D   F
     |-------------------------------LFR3-----------------------------

226  AGT CTC AAC ATC CAT CCT ATG GAG GAA AAT GAT ACT GCA ATG TAT
      S   L   N   I   H   P   M   E   E   N   D   T   A   M   Y
     ----------------------------------------------------------------

271  TTC TGT CAG CAA AGT AAG GAC ATT CCG TAC ACG TTC GGA GGG GGG
      F   C   Q   Q   S   K   D   I   P   Y   T   F   G   G   G
     ------| |--------------LCDR3----------------| |---------------

316  ACC AAG CTG GAA ATA AAA
      T   K   L   E   I   K
     --------LFR4----------|
```

```
  1  GAG ATC CAA TTG GTG CAG TCT GGA CCT GAG CTG AAG AAG CCT GGA
     E   I   Q   L   V   Q   S   G   P   E   L   K   K   P   G
     |-----------------------------------------------HFR1------------

46  GAG ACA GTC AAG ATC TCC TGC AAG GCT TCT GGA TAT ACC TTC GCA
     E   T   V   K   I   S   C   K   A   S   G   Y   T   F   A
     ------------------------------------------------------------|

91  AAC TAT GGA ATG AAC TGG ATG AAG CAG GCT CCA GGA AAG GGT TTA
     N   Y   G   M   N   W   M   K   Q   A   P   G   K   G   L
     |----HCDR1--------|  |--------------------HFR2--------------

136  AAG TGG ATG GGC TGG ATA AAC ACC TAC ACT GGA CAG TCA ACA TAT
     K   W   M   G   W   I   N   T   Y   T   G   Q   S   T   Y
     --------------|  |------------------------HCDR2--------------

181  GCT GAT GAC TTC AAG GAA CGG TTT GCC TTC TCT TTG GAA ACC TCT
     A   D   D   F   K   E   R   F   A   F   S   L   E   T   S
     ------------------------|  |----------------HFR3-----------

226  GCC ACC ACT GCC CAT TTG CAG ATC AAC AAC CTC AGA AAT GAG GAC
     A   T   T   A   H   L   Q   I   N   N   L   R   N   E   D
     ------------------------------------------------------------

271  TCG GCC ACA TAT TTC TGT GCA AGA CGA TTT GGG TTT GCT TAC TGG
     S   A   T   Y   F   C   A   R   R   F   G   F   A   Y   W
     ----------------------------|  |------HCDR3----------|  |--

316  GGC CAA GGG ACT CTG GTC AGT GTC TCT GCA
     G   Q   G   T   L   V   S   V   S   A
     --------------HFR4---------------------|
```

```
  1  GAC ATC CAG ATG ACC CAG TCT CCA TCC TCC TTA TCT GCC TCT CTG
      D   I   Q   M   T   Q   S   P   S   S   L   S   A   S   L
     |---------------------------------------------LFR1------------

46  GGA GAA AGA GTC AGT CTC ACT TGT CGG GCA AGT CAG GAC ATT GGT
      G   E   R   V   S   L   T   C   R   A   S   Q   D   I   G
     -------------------------------| |-----------------LCDR1----

91  AAT AGC TTA ACC TGG CTT CAG CAG GAA CCA GAT GGA ACT ATT AAA
      N   S   L   T   W   L   Q   Q   E   P   D   G   T   I   K
     ---------------| |-----------------------LFR2---------------

136  CGC CTG ATC TAC GCC ACA TCC AGT TTA GAT TCT GGT GTC CCC AAA
      R   L   I   Y   A   T   S   S   L   D   S   G   V   P   K
     ---------------| |------------LCDR2---------| |-------------

181  AGG TTC AGT GGC AGT CGG TCT GGG TCA GAT TAT TCT CTC ACC ATC
      R   F   S   G   S   R   S   G   S   D   Y   S   L   T   I
     ------------------------------LFR3--------------------------

226  AGT AGC CTT GAG TCT GAA GAT TTT GTA GTC TAT TAC TGT CTA CAA
      S   S   L   E   S   E   D   F   V   V   Y   Y   C   L   Q
     ------------------------------------------------| |------

271  TAT GCT ATT TTT CCG TAC ACG TTC GGA GGG GGG ACC AAC CTG GAA
      Y   A   I   F   P   Y   T   F   G   G   G   T   N   L   E
     --------LCDR3--------------| |--------------------LFR4--------

316  ATA AAA
      I   K
     ------|
```

```
  1  GAG CTC GTC ATG ACC CAG TCT CCA TCC TCC TTA TCT GCC TCT CTG
      E   L   V   M   T   Q   S   P   S   S   L   S   A   S   L
     |----------------------------------------------------LFR1----------
```

```
 46  GGA GAA AGA GTC AGT CTC ACT TGT CGG GCA AGT CAG GAA ATT AGT
      G   E   R   V   S   L   T   C   R   A   S   Q   E   I   S
     ------------------------------| |--------------LCDR1--------
```

```
 91  GAT TAC TTA AGT TGC CTT CAG CAG AAA CCA GGT GGA ACT TTT AAA
      D   Y   L   S   C   L   Q   Q   K   P   G   G   T   F   K
     --------------| |-----------------------LFR2---------------
```

```
136  CGC CTG ATC TAC GCC GCA TCC ACT TTA GAT TCT GGT GTC CCA AAA
      R   L   I   Y   A   A   S   T   L   D   S   G   V   P   K
     --------------| |---------------LCDR2-----| |---------------
```

```
181  AGG TTC AGT GGC AGT AGG TCT GGG TCA GAT TAT TCT CTC ACC ATC
      R   F   S   G   S   R   S   G   S   D   Y   S   L   T   I
     -----------------------------LFR3--------------------------
```

```
226  AGC AGC CTT GAG TCT GAA GAT TTT GCA GAC CAT TAC TGT CTA CAA
      S   S   L   E   S   E   D   F   A   D   H   Y   C   L   Q
     ----------------------------------------------------| |------
```

```
271  GAT GTT AGT TAT CCG TGG ACG TTC GGT GGA GGC ACC AAG GTG GAA
      D   V   S   Y   P   W   T   F   G   G   G   T   K   V   E
     ----------LCDR3-----------| |-------------------LFR4--------
```

```
316  ATC AAA
      I   K
     ------|
```

FIG. 14

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 366 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..366

(xi) SEQUENCE DESCRIPTION: SEQ ID NO:1:

```
GAA GTG AAG CTT GAG GAG TCT GGA GGA GGC TTG GTG CAA CCT GGA AGA      48
Glu Val Lys Leu Glu Glu Ser Gly Gly Gly Leu Val Gln Pro Gly Arg
 1               5                  10                  15

TCC ATG AAA CTC TCC TGT GTT GCC TCT GGA TTC ACT TTC AGT AAC TAC      96
Ser Met Lys Leu Ser Cys Val Ala Ser Gly Phe Thr Phe Ser Asn Tyr
             20                  25                  30

TGG ATG AAC TGG GTC CGC CAG TCT CCA GAG AAG GGG CTT GAG TGG GTT     144
Trp Met Asn Trp Val Arg Gln Ser Pro Glu Lys Gly Leu Glu Trp Val
         35                  40                  45

GCT GAA ATT AGA TTG AAA TCT AAT AAT TAT GCA ACA CAT TAT GCG GAG     192
Ala Glu Ile Arg Leu Lys Ser Asn Asn Tyr Ala Thr His Tyr Ala Glu
     50                  55                  60

TCT GTG AAA GGG AGG TTC ACC ATC TCA AGA GAT GAT TCC AAA AGT AGT     240
Ser Val Lys Gly Arg Phe Thr Ile Ser Arg Asp Asp Ser Lys Ser Ser
 65                  70                  75                  80

GTC TAC CTG CAA CTG AAC AAC TTA AGA GCT GAA GAC ACT GGC ATT TAT     288
Val Tyr Leu Gln Leu Asn Asn Leu Arg Ala Glu Asp Thr Gly Ile Tyr
                 85                  90                  95

TAC TGT GCC AGG GAG AGG TAC CTC TAT TAC TAT ACT ATG GAC TAC TGG     336
Tyr Cys Ala Arg Glu Arg Tyr Leu Tyr Tyr Tyr Thr Met Asp Tyr Trp
            100                 105                 110

GGT CAA GGA ACC TCA GTC ACA GTA TCC TCG                             366
Gly Gln Gly Thr Ser Val Thr Val Ser Ser
            115                 120
```

(2) INFORMATION FOR SEQ ID NO:2:

(i) SEQUENCE CHARACTERISTICS:
      (A) LENGTH: 122 amino acids
      (B) TYPE: amino acid
      (D) TOPOLOGY: linear (ii) MOLECULE TYPE: protein (xi) SEQUENCE DESCRIPTION: SEQ ID NO:2:

```
Glu Val Lys Leu Glu Glu Ser Gly Gly Gly Leu Val Gln Pro Gly Arg
 1               5                  10                  15

Ser Met Lys Leu Ser Cys Val Ala Ser Gly Phe Thr Phe Ser Asn Tyr
             20                  25                  30

Trp Met Asn Trp Val Arg Gln Ser Pro Glu Lys Gly Leu Glu Trp Val
         35                  40                  45

Ala Glu Ile Arg Leu Lys Ser Asn Asn Tyr Ala Thr His Tyr Ala Glu
     50                  55                  60

Ser Val Lys Gly Arg Phe Thr Ile Ser Arg Asp Asp Ser Lys Ser Ser
```

```
                65                  70                  75                  80
Val Tyr Leu Gln Leu Asn Asn Leu Arg Ala Glu Asp Thr Gly Ile Tyr
                        85                  90                  95

Tyr Cys Ala Arg Glu Arg Tyr Leu Tyr Tyr Tyr Thr Met Asp Tyr Trp
                100                 105                 110

Gly Gln Gly Thr Ser Val Thr Val Ser Ser
            115                 120
```

(2) INFORMATION FOR SEQ ID NO:3:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..336

(xi) SEQUENCE DESCRIPTION: SEQ ID NO:3:

```
GAT ATT GTC ATG ACG CAA GCA GCA CCC TCT GTA CCT GTC ACT CCT GGA      48
Asp Ile Val Met Thr Gln Ala Ala Pro Ser Val Pro Val Thr Pro Gly
            125                 130                 135

GAG TCA GTA TCC ATC TCC TGC AGG TCT AGT AAG AGT CTC CTG CAT AGT      96
Glu Ser Val Ser Ile Ser Cys Arg Ser Ser Lys Ser Leu Leu His Ser
        140                 145                 150

AAT GGC AAC ACT TTC TTG TAT TGG TTC CTG CAG AGG CCA GGC CAG TCT     144
Asn Gly Asn Thr Phe Leu Tyr Trp Phe Leu Gln Arg Pro Gly Gln Ser
155                 160                 165                 170

CCT CAG CTC CTG ATA TAT CGG ATG TCC AAC CTT GCC TCA GGA GTC CCA     192
Pro Gln Leu Leu Ile Tyr Arg Met Ser Asn Leu Ala Ser Gly Val Pro
                175                 180                 185

GAC AGG TTC AGT GGC AGT GGG TCA GGA ACT GCT TTC ACA CTG AGA ATC     240
Asp Arg Phe Ser Gly Ser Gly Ser Gly Thr Ala Phe Thr Leu Arg Ile
            190                 195                 200

AGT AGA GTG GAG GCT GAG GAT GTG GGT GTT TAT TAC TGT ATG CAA TAT     288
Ser Arg Val Glu Ala Glu Asp Val Gly Val Tyr Tyr Cys Met Gln Tyr
        205                 210                 215

CTA GAA TAT CCT TTC ACG TTC GGC TCG GGG ACA AAG TTG GAA ATC AAA     336
Leu Glu Tyr Pro Phe Thr Phe Gly Ser Gly Thr Lys Leu Glu Ile Lys
    220                 225                 230
```

(2) INFORMATION FOR SEQ ID NO:4:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Ile Val Met Thr Gln Ala Ala Pro Ser Val Pro Val Thr Pro Gly
  1                 5                  10                  15

Glu Ser Val Ser Ile Ser Cys Arg Ser Ser Lys Ser Leu Leu His Ser
             20                  25                  30

Asn Gly Asn Thr Phe Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Ala Phe Thr Leu Arg Ile
```

```
                65                  70                  75                  80
Ser Arg Val Glu Ala Glu Asp Val Gly Val Tyr Tyr Cys Met Gln Tyr
                        85                  90                  95

Leu Glu Tyr Pro Phe Thr Phe Gly Ser Gly Thr Lys Leu Glu Ile Lys
                100                 105                 110
```

(2) INFORMATION FOR SEQ ID NO:5:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..344

(ix) FEATURE:
        (A) NAME/KEY: misc_difference
        (B) LOCATION: replace(295, "")
        (D) OTHER INFORMATION: /note= "This position is * which
            indicates a single base deletion (probably an artifact of
            sequencing)."

(xi) SEQUENCE DESCRIPTION: SEQ ID NO:5:

```
GAG GTG CAG CTG AAG GAG TCT GGG GGA GGC TTA GTG CAG CCT GGA GGG      48
Glu Val Gln Leu Lys Glu Ser Gly Gly Gly Leu Val Gln Pro Gly Gly
            115                 120                 125

TCC CGG AAA CTC TCC TGT GCA GCC TCT GGA TTC ATT TTC AGT AGC TAT      96
Ser Arg Lys Leu Ser Cys Ala Ala Ser Gly Phe Ile Phe Ser Ser Tyr
        130                 135                 140

GCC ATG TCT TGG GTC CGC CAG ACT CCG GAG AAG AGG CTG GAG TGG GTC     144
Ala Met Ser Trp Val Arg Gln Thr Pro Glu Lys Arg Leu Glu Trp Val
145                 150                 155                 160

GCA GCC ATT AGT ACT GAT GGT AGT TTC ATC TTC TAC CCA GAC ACT GTA     192
Ala Ala Ile Ser Thr Asp Gly Ser Phe Ile Phe Tyr Pro Asp Thr Val
                165                 170                 175

AGA GGC CGA TTC ACC ATC TCC AGA GAC AAT GCC AAG AAC ACC CTG TTT     240
Arg Gly Arg Phe Thr Ile Ser Arg Asp Asn Ala Lys Asn Thr Leu Phe
            180                 185                 190

CTG CAA ATG AGC AGT CTA AGG TAT GAG GAC ACG GCC ATG TAT TAC TGT     288
Leu Gln Met Ser Ser Leu Arg Tyr Glu Asp Thr Ala Met Tyr Tyr Cys
        195                 200                 205

TCT AGT CAC TAT GCT ATG GAC TAC TGG GAT CAA GGA ACC GCA GTC AAC     336
Ser Ser Xaa Tyr Ala Met Asp Tyr Trp Asp Gln Gly Thr Ala Val Asn
    210                 215                 220

GTC TCC TCA                                                          345
Val Ser Ser
225
```

(2) INFORMATION FOR SEQ ID NO:6:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:6:

```
Glu Val Gln Leu Lys Glu Ser Gly Gly Gly Leu Val Gln Pro Gly Gly
1               5                   10                  15

Ser Arg Lys Leu Ser Cys Ala Ala Ser Gly Phe Ile Phe Ser Ser Tyr
            20                  25                  30
```

```
Ala Met Ser Trp Val Arg Gln Thr Pro Glu Lys Arg Leu Glu Trp Val
        35                  40                  45

Ala Ala Ile Ser Thr Asp Gly Ser Phe Ile Phe Tyr Pro Asp Thr Val
    50                  55                  60

Arg Gly Arg Phe Thr Ile Ser Arg Asp Asn Ala Lys Asn Thr Leu Phe
65                  70                  75                  80

Leu Gln Met Ser Ser Leu Arg Tyr Glu Asp Thr Ala Met Tyr Tyr Cys
                85                  90                  95

Ser Ser Xaa Tyr Ala Met Asp Tyr Trp Asp Gln Gly Thr Ala Val Asn
                100                 105                 110

Val Ser Ser
```

(2) INFORMATION FOR SEQ ID NO:7:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..324

(xi) SEQUENCE DESCRIPTION: SEQ ID NO:7:

```
GAG CTC GTG CAC ACC CAG TCT CCA GCA ATC ATG TCT GCA TCT CCT GGG      48
Glu Leu Val His Thr Gln Ser Pro Ala Ile Met Ser Ala Ser Pro Gly
115                 120                 125                 130

GAG AAG GTC GCC TTG ACC TGC AAT GCC AGC TCA AGT GTA AGT TCC AGC      96
Glu Lys Val Ala Leu Thr Cys Asn Ala Ser Ser Ser Val Ser Ser Ser
                135                 140                 145

TAC TTG TAC TGG TAC CAG CAG AAG CCA GGA TCC TCC CCC AAA CTC TGG     144
Tyr Leu Tyr Trp Tyr Gln Gln Lys Pro Gly Ser Ser Pro Lys Leu Trp
            150                 155                 160

ATT TAT AGC ACA TCC AAC CTG GCT TCT GGA GTC CCT GCT CGC TTC AGT     192
Ile Tyr Ser Thr Ser Asn Leu Ala Ser Gly Val Pro Ala Arg Phe Ser
        165                 170                 175

GGC CGT GGG TCT GGG ACC TCT TAC TCT CTC ACA ATC ACC AGC ATG GAG     240
Gly Arg Gly Ser Gly Thr Ser Tyr Ser Leu Thr Ile Thr Ser Met Glu
    180                 185                 190

GCT GAA GAT GCT GCC TCT TAT TTC TGC CAT CAG TGG AGT AGT TTC CCA     288
Ala Glu Asp Ala Ala Ser Tyr Phe Cys His Gln Trp Ser Ser Phe Pro
195                 200                 205                 210

TTC ACG TTC GGC TCG GGG ACA AAG TTG GAA ATA AAA                     324
Phe Thr Phe Gly Ser Gly Thr Lys Leu Glu Ile Lys
                215                 220
```

(2) INFORMATION FOR SEQ ID NO:8:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:8:

```
Glu Leu Val His Thr Gln Ser Pro Ala Ile Met Ser Ala Ser Pro Gly
1               5                   10                  15

Glu Lys Val Ala Leu Thr Cys Asn Ala Ser Ser Ser Val Ser Ser Ser
            20                  25                  30
```

```
Tyr Leu Tyr Trp Tyr Gln Gln Lys Pro Gly Ser Ser Pro Lys Leu Trp
         35                  40                  45

Ile Tyr Ser Thr Ser Asn Leu Ala Ser Gly Val Pro Ala Arg Phe Ser
     50                  55                  60

Gly Arg Gly Ser Gly Thr Ser Tyr Ser Leu Thr Ile Thr Ser Met Glu
 65                  70                  75                  80

Ala Glu Asp Ala Ala Ser Tyr Phe Cys His Gln Trp Ser Ser Phe Pro
                 85                  90                  95

Phe Thr Phe Gly Ser Gly Thr Lys Leu Glu Ile Lys
                100                 105
```

(2) INFORMATION FOR SEQ ID NO:9:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..342

(xi) SEQUENCE DESCRIPTION: SEQ ID NO:9:

```
GAG GTG AAA CTT GAG GAG TCT GGA GGA GGC TTG GTG CAA CCT GGA GGA      48
Glu Val Lys Leu Glu Glu Ser Gly Gly Gly Leu Val Gln Pro Gly Gly
110                 115                 120

TCT ATG AAA CTC TCC TGT GTT GCC TCT GGA TTC ACT TTC AGT AAC TAT      96
Ser Met Lys Leu Ser Cys Val Ala Ser Gly Phe Thr Phe Ser Asn Tyr
125                 130                 135                 140

TGG ATG AAT TGG GTC CGC CAG TCT CCA GAG AAG GGG CTT GAG TGG GTC     144
Trp Met Asn Trp Val Arg Gln Ser Pro Glu Lys Gly Leu Glu Trp Val
                145                 150                 155

GCT GAA ATT AAA TTA AAA TCT AAT AAT TAT CCA ACA CAT TAT GCG GAG     192
Ala Glu Ile Lys Leu Lys Ser Asn Asn Tyr Pro Thr His Tyr Ala Glu
            160                 165                 170

TCT GTG AAA GGG AGG TTC ACC GCC TCA AGA GAT GAT TCC AAA AGT AGT     240
Ser Val Lys Gly Arg Phe Thr Ala Ser Arg Asp Asp Ser Lys Ser Ser
        175                 180                 185

ATC TAC CTG CAA ATG AAT AAC TTA AGA ACT GAA GAC ACT GGC ATT TAT     288
Ile Tyr Leu Gln Met Asn Asn Leu Arg Thr Glu Asp Thr Gly Ile Tyr
    190                 195                 200

TTC TGT ACG TTC TGG GAC TAT TGG GGC CGA GGC ACC ACT CTC ACA GTC     336
Phe Cys Thr Phe Trp Asp Tyr Trp Gly Arg Gly Thr Thr Leu Thr Val
205                 210                 215                 220

TCC TCG                                                             342
Ser Ser
```

(2) INFORMATION FOR SEQ ID NO:10:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:10:

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
            20                  25                  30
```

-continued

```
Trp Met Asn Trp Val Arg Gln Ser Pro Glu Lys Gly Leu Glu Trp Val
        35                  40                  45

Ala Glu Ile Lys Leu Lys Ser Asn Asn Tyr Pro Thr His Tyr Ala Glu
 50                  55                  60

Ser Val Lys Gly Arg Phe Thr Ala Ser Arg Asp Asp Ser Lys Ser Ser
 65                  70                  75                  80

Ile Tyr Leu Gln Met Asn Asn Leu Arg Thr Glu Asp Thr Gly Ile Tyr
                 85                  90                  95

Phe Cys Thr Phe Trp Asp Tyr Trp Gly Arg Gly Thr Thr Leu Thr Val
                100                 105                 110

Ser Ser
```

(2) INFORMATION FOR SEQ ID NO:11:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO:11:

```
GAT ATT CTC ATG ACC CAA TCT CCA TCC TCC ATG TCT GTG TCT CTG GGA         48
Asp Ile Leu Met Thr Gln Ser Pro Ser Ser Met Ser Val Ser Leu Gly
115                 120                 125                 130

GAC ACA GTC AGC ATC ACT TGC CAT GCA AGT CAG GGC ATT GAC AAG AAT         96
Asp Thr Val Ser Ile Thr Cys His Ala Ser Gln Gly Ile Asp Lys Asn
                135                 140                 145

ATT GGG TGG TTG CAG CAG AGA CCA GGG AAA TCA TTT AAG GGC CTG ATC        144
Ile Gly Trp Leu Gln Gln Arg Pro Gly Lys Ser Phe Lys Gly Leu Ile
        150                 155                 160

TAT CTT GCA ACC AAC TTA GAA GAT GGA ATT CCA TCA AGG TTC AGT GGC        192
Tyr Leu Ala Thr Asn Leu Glu Asp Gly Ile Pro Ser Arg Phe Ser Gly
        165                 170                 175

AGT GGA TCT GGA GCA GAT TAT TCT CTC ACC ATC ACC AGC CTG GAA TCT        240
Ser Gly Ser Gly Ala Asp Tyr Ser Leu Thr Ile Thr Ser Leu Glu Ser
180                 185                 190

GAA GAT TTT GCA GAC TAT TAC TGT GTA CAG TAT GCT CAG TTT CCA TTC        288
Glu Asp Phe Ala Asp Tyr Tyr Cys Val Gln Tyr Ala Gln Phe Pro Phe
195                 200                 205                 210

ACG TTC GGC TCG GGG ACA AAG TTG GAA ATT AAA                            321
Thr Phe Gly Ser Gly Thr Lys Leu Glu Ile Lys
                215                 220
```

(2) INFORMATION FOR SEQ ID NO:12:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Ile Leu Met Thr Gln Ser Pro Ser Ser Met Ser Val Ser Leu Gly
 1                   5                  10                  15

Asp Thr Val Ser Ile Thr Cys His Ala Ser Gln Gly Ile Asp Lys Asn
                 20                  25                  30

Ile Gly Trp Leu Gln Gln Arg Pro Gly Lys Ser Phe Lys Gly Leu Ile
```

```
                          35                  40                      45
Tyr Leu Ala Thr Asn Leu Glu Asp Gly Ile Pro Ser Arg Phe Ser Gly
             50                  55                  60

Ser Gly Ser Gly Ala Asp Tyr Ser Leu Thr Ile Thr Ser Leu Glu Ser
 65                  70                  75                  80

Glu Asp Phe Ala Asp Tyr Tyr Cys Val Gln Tyr Ala Gln Phe Pro Phe
                     85                  90                  95

Thr Phe Gly Ser Gly Thr Lys Leu Glu Ile Lys
            100                 105
```

(2) INFORMATION FOR SEQ ID NO:13:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..357

(xi) SEQUENCE DESCRIPTION: SEQ ID NO:13:

```
GAG GTG CAA CTG CAG GAG TCA GGA CCT GGC CTG GTG GCG CCC TCA CAG          48
Glu Val Gln Leu Gln Glu Ser Gly Pro Gly Leu Val Ala Pro Ser Gln
            110                 115                 120

AGG CTG TCC ATC ACT TGC TCT GTC TCT GGG TTT TCA TTA ACC AAC TAT          96
Arg Leu Ser Ile Thr Cys Ser Val Ser Gly Phe Ser Leu Thr Asn Tyr
        125                 130                 135

GGT GTA CAC TGG GTT CGC CAG TCT CCA GGA AAG GGT CTA GAG TGG CTG         144
Gly Val His Trp Val Arg Gln Ser Pro Gly Lys Gly Leu Glu Trp Leu
140                 145                 150                 155

GGA GCA ATA TGG GCT GCT GGA AGC ACA AAT TAT AAT TCG GCT CTC ATG         192
Gly Ala Ile Trp Ala Ala Gly Ser Thr Asn Tyr Asn Ser Ala Leu Met
                160                 165                 170

TCC AGA CTG AGC ATC AGC AGA GAC AAC TCC AAG AGC CAA GTT TTC TTA         240
Ser Arg Leu Ser Ile Ser Arg Asp Asn Ser Lys Ser Gln Val Phe Leu
            175                 180                 185

GAA ATG AAC GTT CTG CAA ACT GAT GAC ACA GCC ATG TAC TAC TGT GCC         288
Glu Met Asn Val Leu Gln Thr Asp Asp Thr Ala Met Tyr Tyr Cys Ala
        190                 195                 200

AGA GAC GGG GAT TAC GAC TCT TAT ACT TTG GAC TAC TGG GGT CAA GGA         336
Arg Asp Gly Asp Tyr Asp Ser Tyr Thr Leu Asp Tyr Trp Gly Gln Gly
    205                 210                 215

ACC TCA GTC ACC GTC TCC TCA                                             357
Thr Ser Val Thr Val Ser Ser
220                 225
```

(2) INFORMATION FOR SEQ ID NO:14:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:14:

```
Glu Val Gln Leu Gln Glu Ser Gly Pro Gly Leu Val Ala Pro Ser Gln
 1               5                  10                  15

Arg Leu Ser Ile Thr Cys Ser Val Ser Gly Phe Ser Leu Thr Asn Tyr
            20                  25                  30
```

```
Gly Val His Trp Val Arg Gln Ser Pro Gly Lys Gly Leu Glu Trp Leu
         35                  40                  45

Gly Ala Ile Trp Ala Ala Gly Ser Thr Asn Tyr Asn Ser Ala Leu Met
     50                  55                  60

Ser Arg Leu Ser Ile Ser Arg Asp Asn Ser Lys Ser Gln Val Phe Leu
 65                  70                  75                  80

Glu Met Asn Val Leu Gln Thr Asp Thr Ala Met Tyr Tyr Cys Ala
                 85                  90                  95

Arg Asp Gly Asp Tyr Asp Ser Tyr Thr Leu Asp Tyr Trp Gly Gln Gly
             100                 105                 110

Thr Ser Val Thr Val Ser Ser
         115
```

(2) INFORMATION FOR SEQ ID NO:15:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..339

(xi) SEQUENCE DESCRIPTION: SEQ ID NO:15:

```
GAG CTC GTA ATG ACA CAG TCT CCA TCC TCC CTA GCT GTG TCA GTT GGA        48
Glu Leu Val Met Thr Gln Ser Pro Ser Ser Leu Ala Val Ser Val Gly
120                 125                 130                 135

GAG AAG GTT ACT ATG GGC TGC AAA TCC AGT CAG AGC CTT TTA TAT AGT        96
Glu Lys Val Thr Met Gly Cys Lys Ser Ser Gln Ser Leu Leu Tyr Ser
                140                 145                 150

AGC AAT CAA AAG AAC TAC TTG GCC TGG TAC CAG CAG AAA CCA GGG CAG       144
Ser Asn Gln Lys Asn Tyr Leu Ala Trp Tyr Gln Gln Lys Pro Gly Gln
            155                 160                 165

TCT CCT AAA CTG CTG ATT TAC TGG GCA TCC ACT AGG GAA TCT GGG GTC       192
Ser Pro Lys Leu Leu Ile Tyr Trp Ala Ser Thr Arg Glu Ser Gly Val
        170                 175                 180

CCT GAT CGC TTC ACA GGC AGT GGA TCT GGG ACA GAT TTC ACT CTC ACC       240
Pro Asp Arg Phe Thr Gly Ser Gly Ser Gly Thr Asp Phe Thr Leu Thr
    185                 190                 195

ATC AGC AGT GTG AAG GCT GAA GAC CTG GCA GTT TAT TAC TGT CAG CAA       288
Ile Ser Ser Val Lys Ala Glu Asp Leu Ala Val Tyr Tyr Cys Gln Gln
200                 205                 210                 215

TAT TAT AGC TAT CCA TTC ACG TTC GGC TCG GGG ACA AAG TTG GAA ATA       336
Tyr Tyr Ser Tyr Pro Phe Thr Phe Gly Ser Gly Thr Lys Leu Glu Ile
                220                 225                 230

AAA                                                                    339
Lys
```

(2) INFORMATION FOR SEQ ID NO:16:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:16:

```
Glu Leu Val Met Thr Gln Ser Pro Ser Ser Leu Ala Val Ser Val Gly
 1               5                  10                  15
```

```
Glu Lys Val Thr Met Gly Cys Lys Ser Ser Gln Ser Leu Leu Tyr Ser
             20                  25                  30

Ser Asn Gln Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Phe Thr Phe Gly Ser Gly Thr Lys Leu Glu Ile
             100                 105                 110

Lys
```

(2) INFORMATION FOR SEQ ID NO:17:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..348

(xi) SEQUENCE DESCRIPTION: SEQ ID NO:17:

```
GAG GTT AAG CTT CTC GAG TCT GGA GGT GGC CTG GTG CAG CCT GGA GGA        48
Glu Val Lys Leu Leu Glu Ser Gly Gly Gly Leu Val Gln Pro Gly Gly
115                 120                 125

TCC CTG AAA CTC TCC TGT GCA GCC TCA GGA TTC GAT TTT AGT AGA TAC        96
Ser Leu Lys Leu Ser Cys Ala Ala Ser Gly Phe Asp Phe Ser Arg Tyr
130                 135                 140                 145

TGG ATG AGT TGG GTC CGG CAG GCT CCA GGG AAA GGG CTA GAA TGG ATT       144
Trp Met Ser Trp Val Arg Gln Ala Pro Gly Lys Gly Leu Glu Trp Ile
                150                 155                 160

GGA GAA ATT AAT CCA GAT AGC AGT ACG ATA AAC TAT ACG CCA TCT CTA       192
Gly Glu Ile Asn Pro Asp Ser Ser Thr Ile Asn Tyr Thr Pro Ser Leu
            165                 170                 175

AAG GAT AAA TTC ATC ATC TCC AGA GAC AAC GCC AAA AAT ACG CTG TAC       240
Lys Asp Lys Phe Ile Ile Ser Arg Asp Asn Ala Lys Asn Thr Leu Tyr
        180                 185                 190

CTG CAA ATG AGC GAA GTG AGA TCT GAG GAC ACA GCC CTT TAT TAC TGT       288
Leu Gln Met Ser Glu Val Arg Ser Glu Asp Thr Ala Leu Tyr Tyr Cys
    195                 200                 205

GCA AGA GGG GCG TAT ACT CTG GAC TAC TGG GGT CAA GGA ACC TCA GTC       336
Ala Arg Gly Ala Tyr Thr Leu Asp Tyr Trp Gly Gln Gly Thr Ser Val
210                 215                 220                 225

ACA GTA TCC TCG                                                       348
Thr Val Ser Ser
```

(2) INFORMATION FOR SEQ ID NO:18:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:18:

Glu Val Lys Leu Leu Glu Ser Gly Gly Gly Leu Val Gln Pro Gly Gly

```
                 1               5                   10                  15
            Ser Leu Lys Leu Ser Cys Ala Ala Ser Gly Phe Asp Phe Ser Arg Tyr
                         20                  25                  30

Trp Met Ser Trp Val Arg Gln Ala Pro Gly Lys Gly Leu Glu Trp Ile
                     35                  40                  45

Gly Glu Ile Asn Pro Asp Ser Ser Thr Ile Asn Tyr Thr Pro Ser Leu
                 50                  55                  60

Lys Asp Lys Phe Ile Ile Ser Arg Asp Asn Ala Lys Asn Thr Leu Tyr
            65                  70                  75                  80

Leu Gln Met Ser Glu Val Arg Ser Glu Asp Thr Ala Leu Tyr Tyr Cys
                             85                  90                  95

Ala Arg Gly Ala Tyr Thr Leu Asp Tyr Trp Gly Gln Gly Thr Ser Val
                        100                 105                 110

Thr Val Ser Ser
                    115
```

(2) INFORMATION FOR SEQ ID NO:19:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..329

(ix) FEATURE:
        (A) NAME/KEY: misc_difference
        (B) LOCATION: replace(292, "")
        (D) OTHER INFORMATION: /note= "This position is * which
            indicates a single base deletion (probably an artifact of
            sequencing). This position is generally Pro."

(xi) SEQUENCE DESCRIPTION: SEQ ID NO:19:

```
GAT ATC GTG CTC ACA CAG TCT CCT GCT TCC TTA GCT GTA TCT CTG GGG        48
Asp Ile Val Leu Thr Gln Ser Pro Ala Ser Leu Ala Val Ser Leu Gly
            120                 125                 130

CAG AGG GCC ACC ATC TCA TAC AGG GCC AGC AAA AGT GTC AGT ACA TCT        96
Gln Arg Ala Thr Ile Ser Tyr Arg Ala Ser Lys Ser Val Ser Thr Ser
        135                 140                 145

GGC TAT AGT TAT ATG CAC TGG AAC CAA CAG AAA CCA GGA CAG CCA CCC       144
Gly Tyr Ser Tyr Met His Trp Asn Gln Gln Lys Pro Gly Gln Pro Pro
150                 155                 160

AGA CTC CTC ATC TAT CTT GTA TCC AAC CTA GAA TCT GGG GTC CCT GCC       192
Arg Leu Leu Ile Tyr Leu Val Ser Asn Leu Glu Ser Gly Val Pro Ala
165                 170                 175                 180

AGG TTC AGT GGC AGT GGG TCT GGG ACA GAC TTC ACC CTC AAC ATC CAT       240
Arg Phe Ser Gly Ser Gly Ser Gly Thr Asp Phe Thr Leu Asn Ile His
                185                 190                 195

CCT GTG GAG GAG GAG GAT GCT GCA ACC TAT TAC TGT CAG CAC ATT AGG       288
Pro Val Glu Glu Glu Asp Ala Ala Thr Tyr Tyr Cys Gln His Ile Arg
            200                 205                 210

GAG CCT TAC ACG TTC GGA GGG GGG ACC AAG CTG GAA ATC AAA               330
Glu Xaa Tyr Thr Phe Gly Gly Gly Thr Lys Leu Glu Ile Lys
        215                 220                 225
```

(2) INFORMATION FOR SEQ ID NO:20:

(i) SEQUENCE CHARACTERISTICS:
        (A) LENGTH: 110 amino acids
        (B) TYPE: amino acid (D) TOPOLOGY: linear (ii) MOLECULE TYPE: protein (xi) SEQUENCE DESCRIPTION: SEQ ID NO:20:

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Xaa Tyr Thr Phe Gly Gly Gly Thr Lys Leu Glu Ile Lys
            100                 105                 110

(2) INFORMATION FOR SEQ ID NO:21:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..333

(xi) SEQUENCE DESCRIPTION: SEQ ID NO:21:

GAG CTC GTC ATG ACC CAG TCT CCA GCT TCT TTG GCT GTG TCT CTA GGG        48
Glu Leu Val Met Thr Gln Ser Pro Ala Ser Leu Ala Val Ser Leu Gly
110                 115                 120                 125

CAG AGG GCC ACC ATC TCC TGC AGA GCC AGC GAA ACT GTT GAT AAT TAT        96
Gln Arg Ala Thr Ile Ser Cys Arg Ala Ser Glu Thr Val Asp Asn Tyr
            130                 135                 140

GGT ATT AGT TTC ATG AAC TGG TTC CAA CAG AAA CCA GGA CAG CCA CCC       144
Gly Ile Ser Phe Met Asn Trp Phe Gln Gln Lys Pro Gly Gln Pro Pro
        145                 150                 155

CAA CTC CTC ATC TAT GAT GCT TCC AAC CAA GGA TCC GGG GTC CCT GCC       192
Gln Leu Leu Ile Tyr Asp Ala Ser Asn Gln Gly Ser Gly Val Pro Ala
    160                 165                 170

AGG TTT AGA GGC AGT GGG TCT GGG ACA GAC TTC AGT CTC AAC ATC CAT       240
Arg Phe Arg Gly Ser Gly Ser Gly Thr Asp Phe Ser Leu Asn Ile His
175                 180                 185

CCT ATG GAG GAA AAT GAT ACT GCA ATG TAT TTC TGT CAG CAA AGT AAG       288
Pro Met Glu Glu Asn Asp Thr Ala Met Tyr Phe Cys Gln Gln Ser Lys
190                 195                 200                 205

GAC ATT CCG TAC ACG TTC GGA GGG GGG ACC AAG CTG GAA ATA AAA           333
Asp Ile Pro Tyr Thr Phe Gly Gly Gly Thr Lys Leu Glu Ile Lys
            210                 215                 220

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:22:

```
Glu Leu Val Met Thr Gln Ser Pro Ala Ser Leu Ala Val Ser Leu Gly
 1               5                  10                  15

Gln Arg Ala Thr Ile Ser Cys Arg Ala Ser Glu Thr Val Asp Asn Tyr
             20                  25                  30

Gly Ile Ser Phe Met Asn Trp Phe Gln Gln Lys Pro Gly Gln Pro Pro
         35                  40                  45

Gln Leu Leu Ile Tyr Asp Ala Ser Asn Gln Gly Ser Gly Val Pro Ala
     50                  55                  60

Arg Phe Arg Gly Ser Gly Ser Gly Thr Asp Phe Ser Leu Asn Ile His
 65                  70                  75                  80

Pro Met Glu Glu Asn Asp Thr Ala Met Tyr Phe Cys Gln Gln Ser Lys
                 85                  90                  95

Asp Ile Pro Tyr Thr Phe Gly Gly Gly Thr Lys Leu Glu Ile Lys
            100                 105                 110
```

(2) INFORMATION FOR SEQ ID NO:23:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..345

(xi) SEQUENCE DESCRIPTION: SEQ ID NO:23:

```
GAG ATC CAA TTG GTG CAG TCT GGA CCT GAG CTG AAG AAG CCT GGA GAG      48
Glu Ile Gln Leu Val Gln Ser Gly Pro Glu Leu Lys Lys Pro Gly Glu
            115                 120                 125

ACA GTC AAG ATC TCC TGC AAG GCT TCT GGA TAT ACC TTC GCA AAC TAT      96
Thr Val Lys Ile Ser Cys Lys Ala Ser Gly Tyr Thr Phe Ala Asn Tyr
            130                 135                 140

GGA ATG AAC TGG ATG AAG CAG GCT CCA GGA AAG GGT TTA AAG TGG ATG     144
Gly Met Asn Trp Met Lys Gln Ala Pro Gly Lys Gly Leu Lys Trp Met
145                 150                 155

GGC TGG ATA AAC ACC TAC ACT GGA CAG TCA ACA TAT GCT GAT GAC TTC     192
Gly Trp Ile Asn Thr Tyr Thr Gly Gln Ser Thr Tyr Ala Asp Asp Phe
160                 165                 170                 175

AAG GAA CGG TTT GCC TTC TCT TTG GAA ACC TCT GCC ACC ACT GCC CAT     240
Lys Glu Arg Phe Ala Phe Ser Leu Glu Thr Ser Ala Thr Thr Ala His
                180                 185                 190

TTG CAG ATC AAC AAC CTC AGA AAT GAG GAC TCG GCC ACA TAT TTC TGT     288
Leu Gln Ile Asn Asn Leu Arg Asn Glu Asp Ser Ala Thr Tyr Phe Cys
            195                 200                 205

GCA AGA CGA TTT GGG TTT GCT TAC TGG GGC CAA GGG ACT CTG GTC AGT     336
Ala Arg Arg Phe Gly Phe Ala Tyr Trp Gly Gln Gly Thr Leu Val Ser
            210                 215                 220

GTC TCT GCA                                                          345
Val Ser Ala
    225
```

(2) INFORMATION FOR SEQ ID NO:24:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:24:

| Glu | Ile | Gln | Leu | Val | Gln | Ser | Gly | Pro | Glu | Leu | Lys | Lys | Pro | Gly | Glu |
|---|---|---|---|---|---|---|---|---|---|---|---|---|---|---|---|
| 1 | | | | 5 | | | | | 10 | | | | | 15 | |

| Thr | Val | Lys | Ile | Ser | Cys | Lys | Ala | Ser | Gly | Tyr | Thr | Phe | Ala | Asn | Tyr |
|---|---|---|---|---|---|---|---|---|---|---|---|---|---|---|---|
| | | | 20 | | | | | 25 | | | | | 30 | | |

| Gly | Met | Asn | Trp | Met | Lys | Gln | Ala | Pro | Gly | Lys | Gly | Leu | Lys | Trp | Met |
|---|---|---|---|---|---|---|---|---|---|---|---|---|---|---|---|
| | | 35 | | | | | 40 | | | | | 45 | | | |

| Gly | Trp | Ile | Asn | Thr | Tyr | Thr | Gly | Gln | Ser | Thr | Tyr | Ala | Asp | Asp | Phe |
|---|---|---|---|---|---|---|---|---|---|---|---|---|---|---|---|
| | 50 | | | | | 55 | | | | | 60 | | | | |

| Lys | Glu | Arg | Phe | Ala | Phe | Ser | Leu | Glu | Thr | Ser | Ala | Thr | Thr | Ala | His |
|---|---|---|---|---|---|---|---|---|---|---|---|---|---|---|---|
| 65 | | | | | 70 | | | | | 75 | | | | | 80 |

| Leu | Gln | Ile | Asn | Asn | Leu | Arg | Asn | Glu | Asp | Ser | Ala | Thr | Tyr | Phe | Cys |
|---|---|---|---|---|---|---|---|---|---|---|---|---|---|---|---|
| | | | | 85 | | | | | 90 | | | | | 95 | |

| Ala | Arg | Arg | Phe | Gly | Phe | Ala | Tyr | Trp | Gly | Gln | Gly | Thr | Leu | Val | Ser |
|---|---|---|---|---|---|---|---|---|---|---|---|---|---|---|---|
| | | | 100 | | | | | 105 | | | | | 110 | | |

| Val | Ser | Ala |
|---|---|---|
| | | 115 |

(2) INFORMATION FOR SEQ ID NO:25:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO:25:

| GAC | ATC | CAG | ATG | ACC | CAG | TCT | CCA | TCC | TCC | TTA | TCT | GCC | TCT | CTG | GGA | 48 |
|---|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Leu | Gly | |
| | | | | 120 | | | | | 125 | | | | | 130 | | |

| GAA | AGA | GTC | AGT | CTC | ACT | TGT | CGG | GCA | AGT | CAG | GAC | ATT | GGT | AAT | AGC | 96 |
|---|---|---|---|---|---|---|---|---|---|---|---|---|---|---|---|---|
| Glu | Arg | Val | Ser | Leu | Thr | Cys | Arg | Ala | Ser | Gln | Asp | Ile | Gly | Asn | Ser | |
| | | | 135 | | | | | 140 | | | | | 145 | | | |

| TTA | ACC | TGG | CTT | CAG | CAG | GAA | CCA | GAT | GGA | ACT | ATT | AAA | CGC | CTG | ATC | 144 |
|---|---|---|---|---|---|---|---|---|---|---|---|---|---|---|---|---|
| Leu | Thr | Trp | Leu | Gln | Gln | Glu | Pro | Asp | Gly | Thr | Ile | Lys | Arg | Leu | Ile | |
| | | 150 | | | | | 155 | | | | | 160 | | | | |

| TAC | GCC | ACA | TCC | AGT | TTA | GAT | TCT | GGT | GTC | CCC | AAA | AGG | TTC | AGT | GGC | 192 |
|---|---|---|---|---|---|---|---|---|---|---|---|---|---|---|---|---|
| Tyr | Ala | Thr | Ser | Ser | Leu | Asp | Ser | Gly | Val | Pro | Lys | Arg | Phe | Ser | Gly | |
| | 165 | | | | | 170 | | | | | 175 | | | | | |

| AGT | CGG | TCT | GGG | TCA | GAT | TAT | TCT | CTC | ACC | ATC | AGT | AGC | CTT | GAG | TCT | 240 |
|---|---|---|---|---|---|---|---|---|---|---|---|---|---|---|---|---|
| Ser | Arg | Ser | Gly | Ser | Asp | Tyr | Ser | Leu | Thr | Ile | Ser | Ser | Leu | Glu | Ser | |
| 180 | | | | | 185 | | | | | 190 | | | | | 195 | |

| GAA | GAT | TTT | GTA | GTC | TAT | TAC | TGT | CTA | CAA | TAT | GCT | ATT | TTT | CCG | TAC | 288 |
|---|---|---|---|---|---|---|---|---|---|---|---|---|---|---|---|---|
| Glu | Asp | Phe | Val | Val | Tyr | Tyr | Cys | Leu | Gln | Tyr | Ala | Ile | Phe | Pro | Tyr | |
| | | | 200 | | | | | 205 | | | | | 210 | | | |

| ACG | TTC | GGA | GGG | GGG | ACC | AAC | CTG | GAA | ATA | AAA | | | | | | 321 |
|---|---|---|---|---|---|---|---|---|---|---|---|---|---|---|---|---|
| Thr | Phe | Gly | Gly | Gly | Thr | Asn | Leu | Glu | Ile | Lys | | | | | | |
| | | | 215 | | | | | 220 | | | | | | | | |

(2) INFORMATION FOR SEQ ID NO:26:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:26:

```
Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Asp Ile Gly Asn Ser
                20                  25                  30

Leu Thr Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Val Val Tyr Tyr Cys Leu Gln Tyr Ala Ile Phe Pro Tyr
                85                  90                  95

Thr Phe Gly Gly Gly Thr Asn Leu Glu Ile Lys
            100                 105
```

(2) INFORMATION FOR SEQ ID NO:27:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..321

(xi) SEQUENCE DESCRIPTION: SEQ ID NO:27:

```
GAG CTC GTC ATG ACC CAG TCT CCA TCC TCC TTA TCT GCC TCT CTG GGA      48
Glu Leu Val Met Thr Gln Ser Pro Ser Ser Leu Ser Ala Ser Leu Gly
            110                 115                 120

GAA AGA GTC AGT CTC ACT TGT CGG GCA AGT CAG GAA ATT AGT GAT TAC      96
Glu Arg Val Ser Leu Thr Cys Arg Ala Ser Gln Glu Ile Ser Asp Tyr
        125                 130                 135

TTA AGT TGC CTT CAG CAG AAA CCA GGT GGA ACT TTT AAA CGC CTG ATC     144
Leu Ser Cys Leu Gln Gln Lys Pro Gly Gly Thr Phe Lys Arg Leu Ile
140                 145                 150                 155

TAC GCC GCA TCC ACT TTA GAT TCT GGT GTC CCA AAA AGG TTC AGT GGC     192
Tyr Ala Ala Ser Thr Leu Asp Ser Gly Val Pro Lys Arg Phe Ser Gly
            160                 165                 170

AGT AGG TCT GGG TCA GAT TAT TCT CTC ACC ATC AGC AGC CTT GAG TCT     240
Ser Arg Ser Gly Ser Asp Tyr Ser Leu Thr Ile Ser Ser Leu Glu Ser
        175                 180                 185

GAA GAT TTT GCA GAC CAT TAC TGT CTA CAA GAT GTT AGT TAT CCG TGG     288
Glu Asp Phe Ala Asp His Tyr Cys Leu Gln Asp Val Ser Tyr Pro Trp
    190                 195                 200

ACG TTC GGT GGA GGC ACC AAG GTG GAA ATC AAA                         321
Thr Phe Gly Gly Gly Thr Lys Val Glu Ile Lys
205                 210
```

(2) INFORMATION FOR SEQ ID NO:28:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:28:

```
Glu Leu Val Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Asp Tyr
                20                  25                  30

Leu Ser Cys Leu Gln Gln Lys Pro Gly Gly Thr Phe Lys Arg Leu Ile
            35                  40                  45

Tyr Ala Ala Ser Thr Leu Asp Ser Gly Val Pro Lys Arg Phe Ser Gly
        50                  55                  60

Ser Arg Ser Gly Ser Asp Tyr Ser Leu Thr Ile Ser Ser Leu Glu Ser
 65                 70                  75                  80

Glu Asp Phe Ala Asp His Tyr Cys Leu Gln Asp Val Ser Tyr Pro Trp
                85                  90                  95

Thr Phe Gly Gly Gly Thr Lys Val Glu Ile Lys
            100                 105
```

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:29:

```
Gly Gly Gly Gly Ser Gly Gly Gly Gly Ser Gly Gly Gly Gly Ser
 1               5                  10                  15
```

(2) INFORMATION FOR SEQ ID NO:30:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:30:

```
Ser Ser Ser Ser Gly
 1               5
```

(2) INFORMATION FOR SEQ ID NO:31:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:31:

```
Ser Ser Ser Ser Gly Ser Ser Ser Ser Gly Ser Ser Ser Ser Gly
 1               5                  10                  15
```

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:32:

```
Ile Glu Gly Arg
 1
```

```
(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:33:

Asp Asp Asp Asp Lys
1               5
```

ANTIGEN-BINDING SITES OF ANTIBODY MOLECULES SPECIFIC FOR CANCER ANTIGENS

CROSS REFERENCE TO RELATED APPLICATION

This application is a continuation-in-part of U.S. patent application Ser. No. 08/288,981, filed Aug. 11, 1994 (U.S. Pat. No. 5,629,197), which is a continuation of U.S. patent application Ser. No. 07/190,778 filed May 8, 1998, U.S. Pat. No. 5,169,774, which is a continuation of U.S. patent application Ser. No. 06/842,476, filed Mar. 21, 1986 (abondoned), which is a continuation-in-part of U.S. patent application Ser. No. 06/690,750, filed Jan. 11, 1985 (U.S. Pat. No. 4,753, 894 ), which is a continuation-in-part of U.S. patent application Ser. No. 06/577,976, filed Feb. 8, 1984 (abondoned), which applications are incorporated by reference herein in their entireties and from which priority is claimed pursuant to 35 USC §120.

TECHNICAL FIELD

The present invention relates to novel compositions derived from antigen-binding sites of immunoglobulin molecules specific for cancer antigens. More particularly, the invention relates to molecules that are capable of exhibiting immunological binding properties of antibody antigen-binding sites, and which are useful in specific binding assays, affinity purification schemes, drug or toxin targeting, imaging, and genetic or immunological therapeutics for various cancers among other uses. The invention relates to novel polypeptides having structure and function substantially homologous to native antibody antigen-binding sites, the DNAs encoding those polypeptides, expression cassettes comprising those DNAs, and methods of inducing the production of the polypeptides.

BACKGROUND

Antibodies are normally synthesized by lymphoid cells derived from B lymphocytes of bone marrow. Lymphocytes derived from the same clone produce immunoglobulin of a single amino acid sequence. Lymphocytes cannot be directly cultured over long periods of time to produce substantial amounts of their specific antibody. However, Kohler et al. (1975) *Nature* 256:495–497, demonstrated that a process of somatic cell fusion, specifically between a lymphocyte and a myeloma cell, could yield hybrid cells which grow in culture and produce a specific antibody called a "monoclonal antibody" (hereinafter also referred to as "MAB"). The resulting hybrid cell was called a "hybridoma". A monoclonal antibody belongs to a group of antibodies whose population is substantially homogeneous, i.e. the individual molecules of the antibody population are identical except for naturally occurring mutations. Myeloma cells are lymphocyte tumor cells which, depending upon the cell strain, frequently produce an antibody themselves, although "non-producing" strains are known.

The development of monoclonal antibody technology has provided an enormous opportunity for science and medicine in implementing research, diagnosis and therapy. Monoclonal antibodies are used in radioimmunoassays, enzyme-linked immunosorbent assays, immunocytopathology, and flow cytometry for in vitro diagnosis, and in vivo for diagnosis and immunotherapy of human disease. Waldmann, T. A. (1991) *Science* 252:1657–1662. In particular, monoclonal antibodies have been widely applied to the diagnosis and therapy of cancer, wherein it is desirable to target malignant lesions while avoiding normal tissue. See, e.g., U.S. Pat. Nos. 4,753,894 to Frankel, et al.; 4,938,948 to Ring et al.; and 4,956,453 to Bjorn et al.

For a number of practical and economic reasons, most clinical applications have been based on murine antihuman monoclonal antibodies. Murine antibodies can be raised against molecules which are particularly associated with neoplastic cells using techniques known in the art. In this regard, tumor cells express increased numbers of various receptors for molecules which augment their proliferation (Goustin et al. (1986) *Cancer Res.* 46:1015–1029), many of which receptors are the products of oncogenes (Cline et al. (1984) *Ann Intern Med.* 101:223–228). Thus, a number of monoclonal antibodies directed against receptors for transferrin (Taetle et al. (1987) *Cancer Res.* 47:2040–2044 and Sauvage et al. (1987) *Cancer Res.* 47:747–753), interleukin-2 (Waldmann, T. A. (1986) *Science* 232:727–732 and Wong, et al. (1987) *J. Exp Med.* 166:1055–1069), and epidermal growth factor (Masui et al. (1984) *Cancer Res.* 44:1002–1007, Sato et al. (1983) *Mol Biol Med.* 1:511–529, and Rodeck et al. (1987) *Cancer Res.* 57:3692–3696) have been described. Although such molecules have antigen binding specificities of significant therapeutic value, the use of such murine antibodies in the treatment of human neoplastic disease has been limited since those molecules are immunogenic to the human immune system.

A number of investigators have used monoclonal antibodies as carriers of cytotoxic substances in attempts to selectively direct those agents to malignant tissue. In this manner, radioisotopes, natural toxins, chemotherapy agents, or other substances (such as biological response modifiers) are chemically linked or conjugated to a monoclonal antibody to form "immunoconjugates" and "immunotoxins." More particularly, a number of monoclonal antibodies have been conjugated to toxins such as ricin, abrin, diphtheria toxin and Pseudomonas exotoxin or to enzymatically active portions (A chains) thereof via heterobifunctional agents. See, e.g., U.S. Pat. No. 4,753,894 to Frankel et al.; Nevelle, et al. (1982) *Immunol Rev* 62:75–91; Ross et al. (1980) *European J Biochem* 104; Vitteta et al. (1982) *Immunol Rev* 62:158–183; Raso et al. (1982) *Cancer Res* 42:457–464, and Trowbridge et al. (1981) *Nature* 294:171–173. However, several factors have limited therapy using immunoconjugates or immunotoxins, particularly the production of human antimurine antibodies which greatly lowers the therapeutic index associated with those agents.

Since the mid-1970's, there have been numerous reports of murine monoclonal antibodies that interact with human breast cancer associated antigens. In these reported studies, mice were immunized and boosted with human milk fat globule proteins, breast cancer cell lines or breast cancer membrane extracts. Immune splenocytes were fused with mouse myeloma cells and hybridomas were selected based on some specificity of the culture media for breast or breast cancer antigens. Taylor-Papadimitriou, et al. (1981) *Int. J. Cancer* 28:17–21; Yuan et al. (1982) *JNCI* 68:719–728; Ciocca et al. (1982) *Cancer Res.* 42:4256–4258.

Because of the immunogenicity problems associated with the therapeutic use of murine antibody molecules, a number of chimeric antibodies composed of human and non-human amino acid sequences have been proposed. Particularly, hybrid antibody molecules having variable regions derived from, for example, a murine immunoglobulin fused to constant regions derived from a human immunoglobulin have been described. See e.g., U.S. Pat. No. 4,816,567; Winter et al. (1991) *Nature* 349:293–299; and Lobuglio et al. (1989) *Proc. Nat. Acad. Sci. USA* 86:4220–4224. Further, since constant regions are not required for antigen recognition or binding, antibody fragments such as F(ab), F(ab')$_2$ and Fv which do not comprise the Fc portion have been indicated as useful in radioimmunodetection, or as candidates for conjugation to a large toxin subunit such as ricin A-chain to provide a less immunogenic immunotoxin with an appreciable serum half-life. Dillman, R. O. (1989) *Ann Intern Med.* 111(7):592–603.

A number of recombinant or biosynthetic molecules comprising rodent antigen-binding sites have been described. Particularly, molecules having rodent antigen-binding sites built directly onto human antibodies by grafting only the rodent binding site, rather than the entire variable domain, into human immunoglobulin heavy and light chain domains have been described. See, e.g., Riechmann et al. (1988) *Nature* 332:323–327 and Verhoeyen et al. (1988) *Science* 239:1534–1536. Molecules having an antigen-binding site wherein at least one of the complementarity determining regions (CDRS) of the variable domain is derived from a murine monoclonal antibody and the remaining immunoglobulin-derived parts of the molecule are derived from human immunoglobulin have been described in U.K Patent Publication No. GB 2,276,169, published Sep. 21, 1994. A number of single chain antigen-binding site polypeptides and single chain Fv (sFv) molecules have also been described. See, e.g., U.S. Pat. Nos. 5,132,405 and 5,091,513 to Huston et al.; and U.S. Pat. No. 4,946,778 to Ladner et al.

SUMMARY OF THE INVENTION

It is an object of the invention to provide novel compositions that are derived from antigen-binding sites of immunoglobulins having affinity for cancer antigens. In one aspect of the invention, nucleotide sequences encoding complementarity determining regions ("CDRs") and framework regions ("FRs") derived from variable domains of heavy ("$V_H$") and light ("$V_L$") chains of monoclonal antibodies—capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1—are used in the design and construction of molecules which exhibit immunological binding properties of antibody antigen-binding sites.

In one particular embodiment, a nucleic acid molecule is provided which includes a plurality of nucleotide sequences that encode a monomeric polypeptide. The monomeric polypeptide includes a group of amino acid residues that are homologous to one or more CDRs derived from a $V_H$ or a $V_L$ domain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The CDR residues are interposed between groups of flanking amino acid residues that impart a three-dimensional structure to the molecule, wherein the CDR residues are displayed as projecting loops which form an antigen-binding surface. In one particular embodiment, the flanking amino acid residues are homologous to one or more FRs derived from a $V_H$ or a $V_L$ domain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1.

In various related embodiments, monomeric polypeptides are provided that include a group of amino acid residues that are homologous to one, two, or a set of three CDRs derived from a heavy or light chain of an antibody molecule. Further, monomeric polypeptides are provided that include a group of amino acid residues that are homologous to one, two, three, or a set of four FRs derived from a heavy or light chain of an antibody molecule. Thus, in particular aspects of the invention, nucleic acid molecules are provided that include nucleotide sequences that are substantially homologous to the nucleotide sequence of a single $V_H$ or $V_L$ domain of an antibody capable of binding specifically to a human tumor antigen selected from the group consisting of the HMW mucins bound by 2G3 and 369F10, c-erbB-2 related tumor antigen, an approximately 42 kD glycoprotein, an approximately 55 kD glycoprotein, and the approximately 40, 60, 100 and 200 kD antigens bound by 113F1. The polypeptides encoded by those molecules are capable of exhibiting immunological binding properties of antigen-binding sites.

It is a further object of the invention to use molecular biology techniques to provide nucleic acid molecules encoding synthetic or recombinant moieties derived from the above-described molecules and exhibiting altered or enhanced antigen-binding capabilities, reduced immunogenicity, or combinations thereof. In one particular embodiment, nucleic acid molecules are provided wherein nucleotide sequences encoding various CDRs can be switched or replaced to provide a synthetic variable domain molecule which displays an altered antigen binding specificity.

In various related embodiments, synthetic nucleic acid molecules are provided that include nucleotide sequences that encode one or more CDRs flanked by recombinantly engineered regions. In one particular embodiment, synthetic nucleic acid molecules are provided including sequences encoding a $V_H$ or $V_L$ domain molecule featuring a CDR set derived from a murine antibody molecule that is capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1, wherein the murine CDR set is supported by flanking FRs derived from a human immunoglobulin molecule. In another embodiment, synthetic nucleic acid molecules are provided including nucleotide sequences encoding a $V_H$ or $V_L$ domain molecule including a CDR set derived from a murine antibody molecule that is capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1, wherein the murine CDR set is supported by flanking recombinantly veneered FRs. The recombinantly veneered FRs include a first group of amino acid residues that are homologous to residues derived from a variable region of a heavy or light chain of a murine immunoglobulin, wherein those residues include canonical residues, buried residues, substantially buried residues, interdomain contact residues, and residues directly adjacent to a CDR. The veneered FRs further include a second group of amino acid residues that are homologous to residues derived from FRs of a variable region of a heavy or light chain of a human immunoglobulin.

It is yet a further object of the invention to provide a process for producing the above-described monomeric $V_H$ or $V_L$ domain molecules. Thus, in one embodiment, an expression cassette is provided which includes a nucleic acid molecule encoding a $V_H$ or $V_L$ domain molecule operably linked to a control sequence capable of directing the expression of the nucleic acid molecule. In this manner, expression of the variable domain molecules can be readily effected in a suitable host cell using methods well known in the art. In a related embodiment, a coexpression system is established whereby nucleic acid molecules encoding for complementary monomeric $V_H$ and $V_L$ domain molecules are expressed at substantially the same rate in a suitable host cell. In yet a further related embodiment, a coexpression system is used to produce non-covalent heterodimer molecules that exhibit immunological binding properties of an immunoglobulin which binds to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The subject heterodimer is formed by the coexpression of complementary $V_H$ and $V_L$ domain molecules in a transfected host cell wherein the coexpressed polypeptides dimerize under the influence of non-covalent interdomain contacts to form an antigen-binding site.

It is another object of the invention to provide biosynthetic single-chain Fv ("sFv") molecules which include an antigen-binding site that exhibits immunological binding properties of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. In one embodiment, sFv molecules are provided having at least two polypeptide domains connected by a polypeptide linker spanning the distance between the C-terminus of one domain and the N-terminus of the other, wherein each of the polypeptide domains includes amino acid residues homologous to a set of CDRs interposed between a set of FRs such that the CDRs are capable of participating in immunological binding activity.

In various related embodiments, nucleic acid molecules are provided including nucleotide sequences encoding sFv molecules having re-paired CDRs or CDR sets, molecules which combine murine CDRs with supporting human FRs, or molecules which feature murine CDRs supported by flanking recombinantly veneered FRs.

In yet further related embodiments, nucleic acid molecules are provided which include nucleotide sequences encoding sFv molecules having a third polypeptide domain. The third polypeptide domain is joined either to the first or the second domain by a further polypeptide linker moiety spanning the distance between the C-terminus or N-terminus of one of the first or second domains, and the N-terminus or C-terminus, respectively, of the third polypeptide domain. In particular embodiments, the third polypeptide domain comprises a second antigen-binding site formed as previously described. In other embodiments, the third polypeptide domain comprises an ancillary polypeptide chain that is bioactive, such as a cytokine, toxin, ligand, hormone or enzyme, or the third domain provides a site on which a toxin, drug or remotely detectable moiety can be attached. Thus the various embodiments are useful in specific binding assays, affinity purification techniques, drug or toxin targeting, tumor imaging, and immunological and genetic therapeutics for various cancers.

It is a further related object of the invention to provide expression cassettes which include nucleotide sequences encoding the novel sFv molecules and sFv molecules with ancillary polypeptide regions as just described. The sFv polypeptides can be expressed in suitable prokaryotic and eukaryotic host cells using techniques that are well known in the art.

BRIEF DESCRIPTION OF THE FIGURES

FIG. 1 (SEQ ID NOS: 1 and 2) shows the nucleotide sequence and the predicted amino acid sequence of the $V_H$ encoding domain derived from a 2G3 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 2 (SEQ ID NOS: 3 and 4) shows the nucleotide sequence and the predicted amino acid sequence of the $V_L$ encoding domain derived from a 2G3 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 3 (SEQ ID NOS: 5 and 6) shows the nucleotide sequence and the predicted amino acid sequence of the $V_H$ encoding domain derived from a 33F8 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4. A single base deletion (probably an artifact of sequencing) at the start of HCDR3 (position 295) is indicated with an (*). The predicted amino acid residue has been indicated with an (X).

FIG. 4 (SEQ ID NOS: 7 and 8) shows the nucleotide sequence and the predicted amino acid sequence of the $V_L$ encoding domain derived from a 33F8 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 5 (SEQ ID NOS: 9 and 10) shows the nucleotide sequence and the predicted amino acid sequence of the $V_H$ encoding domain derived from a 113F1 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 6 (SEQ ID NOS: 11 and 12) shows the nucleotide sequence and the predicted amino acid sequence of the $V_L$ encoding domain derived from a 113F1 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 7 (SEQ ID NOS: 13 and 14) shows the nucleotide sequence and the predicted amino acid sequence of the $V_H$ encoding domain derived from a 260F9 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 8 (SEQ ID NOS: 15 and 16) shows the nucleotide sequence and the predicted amino acid sequence of the $V_L$ encoding domain derived from a 260F9 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 9 (SEQ ID NOS: 17 and 18) shows the nucleotide sequence and the predicted amino acid sequence of the $V_H$ encoding domain derived from a 317G5 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 10 (SEQ ID NOS: 19 and 20) shows the nucleotide sequence and the predicted amino acid sequence of the $V_L$ encoding domain derived from a 317G5 hybridoma. Proceeding from the N-terminus, the sequences of the three CDRs are generally indicated LCDR1, LCDR2 and LCDR3, Also proceeding from the N-terminus, the sequences of the four FRs are generally indicated at LFR1, LFR2, LFR3 and LFR4. A single base deletion (probably an artifact of sequencing) within the LCDR3 (position 296) is indicated with an (*). The corresponding predicted amino acid residue has been indicated with an (X). The deletion is most likely the loss of a single base at position 16 or 17 within the CDR (LCDR3). This position is generally Pro (P), thus a Pro residue represents the most reasonable estimate of the identity of (X) in the predicted amino acid sequence.

FIG. 11 (SEQ ID NOS: 21 and 22) shows the nucleotide sequence and the predicted amino acid sequence of the $V_L$ encoding domain derived from a 369F10 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 12 (SEQ ID NOS: 23 and 24) shows the nucleotide sequence and the predicted amino acid sequence of the $V_H$ encoding domain derived from a 520C9 hybridoma. Proceeding from the N-terminus, the sequences of the three CDRs are generally indicated HCDR1, HCDR2 and HCDR3. Also proceeding from the N-terminus, the sequences of the four FRs are generally indicated at HFR1, HFR2, HFR3 and HFR4.

FIG. 13 (SEQ ID NOS: 25 and 26) shows the nucleotide sequence and the predicted amino acid sequence of the $V_L$ encoding domain derived from a 520C9 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

FIG. 14 (SEQ ID NOS: 27 and 28) shows the nucleotide sequence and the predicted amino acid sequence of the $V_L$ encoding domain derived from a 650E2 hybridoma. Proceeding from the N-terminus, the sequences of the three CDRs are generally indicated LCDR1, LCDR2 and LCDR3. Also proceeding from the N-terminus, the sequences of the four FRs are generally indicated at LFR1, LFR2, LFR3 and LFR4.

DETAILED DESCRIPTION OF THE INVENTION

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

An "antigen" includes any substance that may be specifically bound by an antibody molecule. Thus, the term "antigen" encompasses biologic molecules including, but not limited to, simple intermediary metabolites, sugars, lipids, autoacids, and hormones, as well as macromolecules such as complex carbohydrates, phopholipids, nucleic acids and proteins.

An "immunogen" is a macromolecular antigen that is capable of initiating lymphocyte activation resulting in an antigen-specific immune response. An immunogen therefore includes any molecule which contains one or more epitopes that will stimulate a host's immune system to initiate a secretory, humoral and/or cellular antigen-specific response.

The term "antibody" encompasses polyclonal and monoclonal antibody preparations, as well as preparations including hybrid antibodies, altered antibodies, chimeric antibodies and, humanized antibodies.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins.

Methods of making polyclonal and monoclonal antibodies are known in the art. Polyclonal antibodies are generated by immunizing a suitable animal, such as a mouse, rat, rabbit, sheep or goat, with an antigen of interest. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

Rabbits, sheep and goats are preferred for the preparation of polyclonal sera when large volumes of sera are desired. These animals are good design choices also because of the availability of labeled anti-rabbit, anti-sheep and anti-goat antibodies. Immunization is generally performed by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2–6 weeks later with one or more injections of the antigen in saline, preferably using Freund's incomplete adjuvant ("FIA"). Antibodies may also be generated by in vitro immunization, using methods known in the art. Polyclonal antisera is then obtained from the immunized animal.

Monoclonal antibodies are generally prepared using the method of Kohler and Milstein, *Nature* (1975) 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

The "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439–473.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, preferably at least 4–7 amino acids, more preferably at least 8–10 amino acids, and even more preferably at least 11–15 amino acids, or which is im-munologically identifiable with a polypeptide encoded in the sequence. This terminology also includes a polypeptide expressed from a designated nucleic acid sequence.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition. Thus, for example, an isolated nucleic acid molecule which encodes a particular CDR polypeptide consists essentially of the nucleotide coding sequence for the subject molecular recognition unit.

"Homology" refers to the percent of identity between two polynucleotide or polypeptide moieties. The correspondence between the sequence from one form to another can be determined by techniques known in the art. For example, homology can be determined by a direct comparison of the sequence information between two polypeptide molecules. Alternatively, homology can be determined by hybridization of polynucleotides under conditions which form stable duplexes between homologous regions (for example, those which would be used prior to $S_1$ digestion), followed by digestion with single-stranded specific nuclease(s), followed by size determination of the digested fragments. Two DNA or polypeptide sequences are "substantially homologous" when at least about 80% (preferably at least about 90%, and most preferably at least about 95%) of the nucleotides or amino acids match over a defined length of the molecule.

The terms "recombinant DNA molecule," or "recombinant nucleic acid molecule" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

The term "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for-example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "coding sequence" is a nucleic acid molecule which is translated into a polypeptide, usually via mRNA, when placed under the control of appropriate regulatory sequences. The boundaries of the coding sequence may be determined by a translation start codon at the 5'-terminus and a translation stop codon at the 3'-terminus. A coding sequence can include, but is not limited to, cDNA, and recombinant nucleotide sequences.

"Control sequence" refers to nucleic acid sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression of a coding sequence, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

"Transfection" refers to the uptake of foreign DNA by a cell, and a cell has been "transfected" when exogenous DNA has been introduced inside the cell membrane. In this manner, the exogenous DNA may or may not be integrated (covalently linked) to chromosomal DNA making up the genome of the cell. In procaryotes and yeasts, for example, the exogenous DNA can be maintained on an episomal element, such as a plasmid. With respect to the invention, a eucaryotic cell is "stably transfected" when exogenous DNA has become integrated into the cellular genome so that it is inherited by daughter cells through chromosome replication. This stability is demonstrated by the ability of the eucaryotic cell to establish cell lines or clones comprised of a population of daughter cells containing the exogenous DNA. "Transient transfection" refers to cases where exogenous DNA does not remain in the cells for an extended period of time, e.g., where plasmid DNA is transcribed into mRNA and translated into protein without integration into the host cell genome.

A "host cell" is a cell which has been transfected, or is capable of transfection, by an exogenous DNA sequence using methods within the skill of those in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. More particularly, there are two major steps in transfection: first, the exogenous DNA must traverse the recipient (host) cell plasma membrane in order to be exposed to the cell's transcription and replication machinery; and second, the DNA must either become stably integrated into the host cell genome, or be capable of extra-chromosomal replication at a sufficient rate. A number of transfection methods have been described in the art, such as calcium phosphate co-precipitation (Graham et al. (1973) *Virol.* 52:456–467), direct micro-injection into cultured cells (Capecchi, M. R. (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transfection (Felgner et al. (1987) *Proc. Natl. Acad. Sci. USA* 84:7413–7417), and nucleic acid delivery using high-velocity microprojectiles (Klein et al. (1987) *Nature* 327:70–73).

"Gene transfer" or "gene delivery" refers to methods or systems for reliably inserting foreign DNA into host cells such that the transferred genetic material is stable with respect to the loci of insertion and is also susceptible of expression by the host cells. Such methods provide a unique approach for the treatment of acquired and inherited diseases. A number of systems have been developed for gene transfer into mammalian cells. See, e.g., U.S. Pat. No. 5,399,346.

B. General Methods

As used herein with respect to the exemplified murine monoclonal antihuman breast cancer antibodies, the term "functional equivalent" means a monoclonal antibody that: (a) crossblocks an exemplified monoclonal antibody; (b) binds selectively to human breast cancer cells; (c) has a G or M isotype; and (d) binds to the same antigen as determined by immunoprecipitation or sandwich immunoassay. Further, as used herein with regard to the exemplified monoclonal antibody-producing hybridomas of the invention, the term "progeny" is intended to include all derivatives, issue, and offspring of the parent hybridoma that produce the monoclonal antihuman breast cancer antibody produced by the parent, regardless of generation or karyotypic identity.

Initially, mammalian immunoglobulin molecules prepared in response to an immunogen consisting essentially of membrane extracts derived from cancerous human breast tissue, or cells derived from a human cancer cell line selected from the group consisting of SKBr3, MCF7, BT20, ZR751, ZR7530 and MDAMB231 were produced to provide antigen-binding sites for use under the invention. More particularly, monoclonal antibodies capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1 were produced as follows.

Antibody-producing fusion partners used to make the following hybridomas were generated by immunizing mice with live human breast cancer cells, or membrane extracts derived from cancerous human breast tissue, or with cells derived from a human cancer cell line selected from the group consisting of SKBr3, MCF7, BT20, ZR751, ZR7530 and MDAMB231.

Fresh postsurgical human breast cancer tissue and a variety of normal tissues were used to prepare membrane extracts by homogenization and discontinuous sucrose gradient centrifugation. Human breast cancer cell lines were obtained from the Breast Cancer Task Force, the American Type Culture Collection (ATCC), and from Dr. Jorgen Fogh at Memorial Sloan Kettering. The cells were maintained and passaged as recommended by the Breast Cancer Task Force, the ATCC and Dr. Fogh. For immunizations, either the membrane extract containing 100 µg of protein (Lowry assay) or ten million live breast cancer cells were inoculated intra-peritoneally into five week old Balb/c mice. The mice were boosted identically twice at monthly intervals. Three days after the last boost, the spleens were removed for cell fusion.

Hybridomas were prepared using the general somatic cell hybridization techniques of Kohler et al. (1975) *Nature* 256:495–497 as modified by Buck et al. (1982) *In Vitro* 18:377–381. Available murine myeloma lines, such as those available from the Salk Institute, Cell Distribution Center, (San Diego, Calif.) can be used in the hybridization. More particularly, somatic cell hybrids were prepared by the method of Buck et al., (supra), using the azaguanine resistant, non-secreting murine myeloma cell line SP2/0-Ag14 (obtained from the American Type Culture Collection, designated under cell repository line number ATCC CRL1581). All hybridoma cell lines were cloned by limiting dilution. Half of the fusions employed splenocytes from mice immunized with breast cancer membrane extracts, and half used splenocytes from mice immunized with live breast cancer cell lines. 96-well polystyrene flat-bottom microtiter plates were used. Eighty-three thousand four hundred twenty four (83,424) wells were generated from those fusions, of which 22,459 exhibited hybridoma growth.

Hybridoma supernatant was assayed for reactive antibody in either a solid phase enzyme-linked immunosorbent assay (ELISA) with the immunizing breast cancer membrane extract or an indirect immunofluorescence assay with the immunizing breast cancer cell line. For the solid phase membrane ELISA, 40 µl of 0.1 mg/ml breast cancer membrane protein were placed in polyvinyl chloride (PVC) microtiter wells for 12 hr at 4° C. The extract was aspirated and the wells washed with phosphate buffered saline (PBS) containing 1% bovine serum albumin (BSA). The wells were then incubated with 45 µl of a 1:10 dilution of hybridoma supernatant. The diluent was medium with 25 mM of a buffer, 10% bovine serum, and 0.1% sodium azide. After 30 min at room temperature, the wells were again washed and incubated 45 min at 37° C. with a 1:200 dilution of peroxidase conjugated goat anti-mouse IgG. The diluent was PBS. The wells were then washed with PBS and reacted with 200 µl of 2,2-azino-di(3-ethylbenzthiazoline sulphonic acid) in 0.1 M sodium citrate buffer pH 4.2 for 30 min at room temperature. Optical density was measured at 405 nm on a MicroElisa Reader. For each experiment a positive control, anti-beta 2 microglobulin at 5 µg/ml, was reacted with normal human kidney membrane. This gave an optical density of 1.0±0.1 (standard deviation). The background was 0±0.1 optical density units (O.D.) using medium without mouse monoclonal antibody. Wells that gave a reaction on the breast cancer membrane extract of greater than 0.7 O.D. were saved.

For the indirect immunofluorescence cell line assay, one hundred thousand breast cancer cells of the immunizing cell line were placed overnight with appropriate media in each chamber of a set of eight chambered slides. Similarly, one hundred thousand fibroblast cells from cell line CC95 were incubated overnight in chambered slide wells. The cells were washed with PBS containing 1% BSA. The wells, both breast cancer and fibroblast, were incubated for 30 min at 4° C. with 1:10 dilutions of hybridomas supernatant. The cells were again washed and incubated 30 min at 4° C. with a 1:50 dilution of fluorescein isothiocyanate (FITC)-conjugated goat F(ab')$_2$ anti-mouse Ig. The cells were washed three times, fixed in 1.5% formaldehyde in PBS for five min, chambers removed and rinsed in PBS. The slides were then mounted in a composition containing polyvinyl alcohol, glycerol, buffers and a preservative and examined with a fluorescence microscope. Hybridoma wells showing strong fluorescent binding to breast cancer cells but no fluorescent binding to fibroblasts were saved. Five thousand one hundred fifty-six hybridoma wells revealed breast cancer reactivity in the initial screen.

Supernatants from the 5156 positive wells were then tested in solid phase ELISA with eight normal tissue membrane extracts (liver, lung, colon, stomach, kidney, tonsil, spleen and pancreas). Any well supernatant giving an ELISA O.D. greater than 0.3 was discarded. One thousand one hundred one of the supernatants were found to be unreactive with the normal tissue extracts.

The 1101 hybridoma supernatants were tested on frozen sections of human breast carcinoma tissues. Six micron sections were attached to slides, fixed 10 min in acetone at 4° C., dried 10 min at room temperature, washed with PBS, blocked with horse serum and incubated 20 min at room temperature with 200 µl (neat) hybridoma supernatant. The slides were washed with PBS, and finally incubated 20 min at 37° C. with a 1:50 dilution of peroxidase conjugated rabbit anti-mouse Ig, washed again with PBS, and finally 7.5 min at 37° C. with 0.5 mg/ml diaminobenzidine in 0.05 M Tris buffer pH 7.2 containing 0.01% peroxide. The slides were stained with hematoxylin, dehydrated and mounted in a medium containing 35.9% methyl/n-butylmethacrylate copolymer, 7.1% butyl benzyl phthalate, and 0.3%, 2,6-ditertbutyl-p-cresol. One hundred twenty-four wells yielded breast cancer selective binding and were cloned.

The selectivity and range of a given antibody is determined by testing it against panels of (a) human breast cancer tissues and cells and (b) normal human tissues or cells of breast or other origin. In selecting the antibodies used herein, over twenty-two thousand growing hybridoma cultures were initially screened against the immunizing breast tumor membranes or cell line, a panel of eight normal tissue membranes, a fibroblast cell line and breast tumor frozen sections. Clones that reacted with the neoplastic materials but not the normal materials were identified in this initial screen and chosen for isotyping and additional screening for selectivity and range. The additional screening involved; sixteen normal tissue sections, five normal blood cell types, eleven nonbreast neoplasm sections, twenty-one breast cancer sections and fourteen breast cancer cell lines. Antibodies were deemed to bind selectively to breast cancer if they bound strongly to less than about ⅓ of the normal tissues and blood cell types. One hundred twenty-seven antibodies were purified and tested on the additional screen.

Of the antibodies tested above, 8 monoclonal breast cancer selective antibodies were selected for further screening and classification under the invention. The antibodies selected are produced by the following hybridoma cell lines: 2G3 (ATCC No. HB8491), 33F8 (ATCC No. HB8697), 113F1 (ATCC No. HB8489), 260F9 (ATCC No. HB8488 and HB8662), 317G5 (ATCC No. HB8485), 369F10 (ATCC No. HB8682), 520C9 (ATCC No. HB8696), and 650E2 (ATCC No. HB10812). Seventeen (32A1, 33F8, 41B4, 44B2, 44F4, 106A10, 87H7, 113F1, 200F9, 219F3, 245E7, 2G3, 260F9. 274G6, 280D11, 266B2, and 454C11) human breast cancer selective IgGs were conjugated to ricin A chain using N-succinimidyl-3-(2-pyridyldithio) propionate (SPDP) as a coupling agent. The conjugates were tested against MCF-7 cells in a 24-hour tissue culture assay. Nine of the antibodies (260F9, 113F1, 2G3, 280D11, 266B2, 33F8, 245E7, and 454C11) exhibited TCID 50% of less than 10 nM.

Further details of the characterization of the subject antibodies are provided in the examples below.

More particularly, the immunoglobulin class and subclass of the monoclonal breast cancer selective antibodies were determined. Antibodies were also internally labeled by growing 2–3×10⁶ hybridoma cells for 4 hr in methionine-free medium containing 0.2 µCi $^{35}$S methionine. $^{35}$S-labeled antibodies were immunoprecipitated with fixed staphylococcus A cells or with staphylococcus A cells pre-coated with rabbit anti-mouse immunoglobulin, and the immunoprecipitates were analyzed by SDS-PAGE to determine antibody light and heavy chain mobility, lack of extra chains, and the ability of each antibody to bind staphylococcal protein A.

The antibodies were expanded in vivo. Balb/c or F1 (C57B/6 x Balb/c) mice were primed with 0.5 ml pristane intraperitoneally (ip) and after 10–14 days inoculated with one million log phase hybridoma cells in PBS. Ascites fluid was stored at −70° C. and thawed and filtered through a 0.8 micron filter unit before further purification.

IgG antibodies that bound staphylococcal protein A were purified by affinity chromatography on protein A-chromatographic resin containing agarose, dextron and/or acrylamide with pH step gradient elution. IgG antibodies that did not bind protein A were precipitated by addition of ammonium sulfate to 40% saturation at 0° C. The precipitates were redissolved in PBS, dialysed to 20 mM Tris pH 7.2 and chromatographed on a 1.6×50 cm column of diethylaminoethyl cellulose (DEAE) eluting with a 1.5 liter 0–600 mM NaCl gradient at 4° C. at a flow rate of 1 ml/min. In each case, column fractions were monitored by SDS-PAGE and the purest antibody fractions were pooled, concentrated to 1–3 mg/ml, dialysed to PBS/0.02% NaN$_3$, and stored at 4° C.

IgM antibodies were purified by gel filtration on a 2.6×40 cm column of chromatographic resin containing agarose, dextron and/or acrylamide eluting with PBS/0.01% sodium azide at room temperature at a flow rate of 1 ml/min.

In order to evaluate their selectivity for breast cancer, the purified antibodies were tested by immunoperoxidase section staining on sections of sixteen normal tissues, and by immunofluorescent cell sorting on five blood cell types. Immunoperoxidase staining was performed as above except that know dilutions of purified antibodies in PBS in the range of 1–40 µg/ml were used instead of hybridoma supernatants. The pure antibodies were first titrated to find the minimal concentration giving strong immunoperoxidase staining on breast cancer sections and then used at the concentration for the normal tissue tests. Peripheral blood cells (platelets, lymphocytes, red blood cells, granulocytes, and monocytes) were prepared by centrifugation using a medium which separates monocytes from polymorphonuclear leucocytes. The cells were reacted with antibody at the optimal concentration determined above for 30 min at 4° C., washed, reacted with a 1:50 dilution of fluorescence isothiocyanate-conjugated goat anti-mouse Ig for 30 min at 4° C., washed again and examined in a cell sorter. The wash buffer and diluents were PBS with 1% gelatin and 0.02% sodium azide. The cell sorter was equipped with a 76 micron nozzle and a one watt argon ion laser at 488 nm. An 80 mm confocal lens was used on the optical rail assembly for focusing. Other filters used were a 515 interference filter and a 515 nm absorbance filter (for scattered laser light) and a neutral density 1.5 filter for forward angle light scatter. Contour plots of log fluorescein fluorescence versus forward angle light scatter were used for sample analysis. Seventeen (32A1, 33F8, 41B4, 44B2, 44F4, 106A10, 87H7, 113F1, 200F9, 219F3, 245E7, 2G3, 260F9, 274G6, 280D11. 266B2, and 454C11) of the IgG antibodies were found to bind strongly to three or less of the normal tissues/cells (pancreas, esophagus, lung, kidney, colon, stomach, brain, tonsil, liver, heart, ovary, skin breast, platelets, red cells, lymphocytes, monocytes and granulocytes).

The binding behaviors of the antibodies disclosed herein are reported in Table 1 below.

TABLE 1

ANTIBODY BINDING TO NORMAL TISSUE SECTIONS

| Tissue Antibody | Pancreas | Esophagus | Lung | Kidney | Colon | Stomach | Brain | Tonsil |
|---|---|---|---|---|---|---|---|---|
| 33FB | 0 | 2E | 0 | 1T | 0 | 0 | 0 | 1Ly |
| 113F1 | 2Ac | 2E | 0 | 0 | 0 | 2G | 0 | 1E |
| 2G3 | 2Ac | 2E | 1A | 2T | 0 | 1L | 0 | 1E |
| 260F9 | 1Ac | 2E | 2A | 1T | 0 | 1G | 0 | 2E |
| 317G5 | 1Ac, I | 0 | 0 | 2T | 1G | 0 | 0 | 0 |
| 520C9 | 0 | 0 | 0 | 1T | 0 | 0 | 0 | 0 |
| 369F10 | 0 | 0 | 0 | 0 | 0 | 1G | 0 | 0 |
| 650E2 | 1Ac, I | 0 | 1–2A | 2T | 2G | 0 | 0 | 0 |

| Tissue Antibody | Liver | Heart | Ovary | Skin | Breast | Bone Marrow | Uterus | Bladder |
|---|---|---|---|---|---|---|---|---|
| 33FB | 0 | 0 | 0 | 1W | 0 | 1Mk | 1L | 1E |
| 113F1 | 0 | 0 | 0 | 0 | 0 | 0 | 0 | 1E |
| 2G3 | 0 | 0 | 0 | 0 | 2E | 0 | 2L | 2E |
| 260F9 | 2D | 0 | 0 | 2E, 2H | 2E | 0 | 1L | 2E |
| 317G5 | 2D | 0 | 0 | 0 | 0 | 0 | 1G | 0 |
| 520C9 | 0 | 0 | 0 | 0 | 0 | 0 | 0 | 0 |
| 369F10 | 0 | 0 | 0 | 1S | 0 | 0 | 0 | 0 |
| 650E2 | 2D | 0 | 0 | 0 | 1 | 0 | 2G | 0 |

Staining intensity: 2 = strong; 1 = weak; 0 = negative.
A = alveolar cells; Ac = acini; B = Bowman's capsule; D = ducts; T = epithelial; G = glands; Gr = granulocytes; H = hair follicles; I = islets; L = lumen; ± = apical cytoplasm; Ly = lymphocytes; M = macrophages; Mk = megakonyocytes; My = myelin; S = sepaceous; St = stroita; T = tubules; U = glomeruli; W = sweat glands. There was no binding to platelets, red cells, lymphocytes, monocytes or granulocytes. None of the antibodies bound fibroblasts.

In order to determine how wide a range of breast cancers might be recognized by each antibody, the breast cancer selective antibodies were tested by immunoperoxidase staining on frozen sections of 27 different breast tumors. The breast cancers used for section staining were all infiltrating intraductal carcinomas, so no correlation of antibody binding with histologic type of breast cancer could be made. In addition, no correlation between antibody binding and the nodal status or estrogen receptor status was found for the twelve tumors for which donor information was available. Antibodies reacted equally well with metastatic and primary breast tumors. The results of these tests for the subject antibodies are reported in Table 2 below.

TABLE 2

ANTIBODY BINDING TO BREAST CANCER TISSUE SECTIONS*

| Antibody | LA | KA | JA | IA | HA | GA | E | EA | TA |
|---|---|---|---|---|---|---|---|---|---|
| 2G3 | 1 | 2 | 1 | 2 | 2 | 2 | ND | 2 | 2 |
| 33F8 | 1 | 1 | 0 | 0 | 0 | 0 | 1 | 0 | 0 |
| 113F1 | 0 | 1 | 1 | 0 | 0 | 0 | 0 | 0 | 0 |
| 260F9 | 0 | 1 | 0 | 1 | 0 | 1 | ND | 1 | 2 |
| 317G5 | 1 | ND | 0 | 0 | 1 | ND | ND | 0 | 0 |
| 520C9 | 0 | ND | 0 | 2 | 0 | ND | ND | 2 | 0 |
| 369F10 | 2 | 2 | 2 | 2 | 0 | 1 | ND | 1 | 0 |
| 650E2 | 1 | ND | 1 | ND | 1 | ND | ND | 0 | 0 |

| Antibody | UA | RA | SA | O | R | MA | BA | NA | FA |
|---|---|---|---|---|---|---|---|---|---|
| 2G3 | 2 | 2 | 2 | 2 | 2 | 1 | 2 | 2 | 2 |
| 33F8 | 0 | 0 | 0 | 1 | 0 | 0 | 0 | 0 | 0 |
| 113F1 | 0 | 1 | 0 | 0 | 0 | 0 | 0 | 0 | 0 |
| 260F9 | 0 | 0 | 0 | 1 | 0 | 0 | 1 | 1 | 1 |
| 317G5 | 0 | 1 | 1 | ND | 0 | 1 | 0 | 1 | 1 |
| 520C9 | 1 | 0 | 0 | ND | 0 | 2 | 0 | 1 | 0 |
| 369F10 | 1 | 1 | 2 | 2 | 0 | 6 | 2 | 2 | 2 |
| 650E2 | 1 | 1 | 1 | ND | ND | 2 | 1 | 2 | 1 |

| Antibody | LMA | LME | MBA | Z | YA | KB | GB | IC | EC |
|---|---|---|---|---|---|---|---|---|---|
| 2G3 | 2 | 2 | 2 | 2 | ND | ND | ND | ND | ND |
| 33F8 | 0 | 0 | 0 | ND | ND | ND | ND | ND | ND |
| 113F1 | 0 | 0 | 0 | ND | ND | ND | ND | ND | ND |
| 260F9 | 0 | 1 | 1 | 0 | ND | ND | ND | ND | ND |
| 317G5 | 0 | 0 | 0 | 0 | 0 | 1 | 1 | ND | ND |
| 520C9 | 0 | 0 | 0 | 0 | ND | ND | ND | ND | ND |

TABLE 2-continued

| ANTIBODY BINDING TO BREAST CANCER TISSUE SECTIONS* | | | | | | | | | |
|---|---|---|---|---|---|---|---|---|---|
| 369F10 | 2 | 2 | 2 | 1 | ND | ND | ND | ND | ND |
| 650E2 | 1 | 0 | 1 | 1 | 1 | 2 | 1 | 2 | 2 |

*Staining intensity: 2 = strong; 1 = weak; 0 = negative; ND = not determined

The antibodies were further evaluated for range of breast cancer recognition by cell line immunofluorescence assays on 14 breast cancer cell lines. Table 3 below reports the results of these tests for the subject antibodies.

Seventeen antibodies (32A1, 33F8, 41B4, 44B2, 44F4, 106A10, 87H7, 113F1, 200F9, 219F3, 245E7, 2G3, 260F9, 274G6, 280D11, 266B2, and 454C11) in PBS at 1–2 mg/ml were treated with SPDP as described by Carlsson, J., et al.

TABLE 3

| ANTIBODY BINDING TO BREAST CANCER CELL LINES | | | | | | | |
|---|---|---|---|---|---|---|---|
| Antibody | SKBr3 | BT483 | MCF7 | BT20 | ZR751 | MDAMB231 | CAMA1 |
| 2G3 | + | + | + | + | + | + | + |
| 33F8 | + | + | + | + | + | − | + |
| 113F1 | + | + | + | + | + | + | + |
| 260F9 | + | + | + | + | + | + | + |
| 317G5 | + | + | + | + | + | − | + |
| 520C9 | + | + | − | − | − | NT | + |
| 369F10 | − | + | − | − | − | − | + |
| 650E2 | + | + | + | + | + | NT | + |
| Antibody | ALAB | BT549 | BT474 | T47D | MDAMB157 | MDAMB330 | ZR7530 |
| 2G3 | + | + | + | + | + | − | + |
| 33F8 | + | + | + | − | + | + | − |
| 113F1 | − | − | + | + | + | + | − |
| 260F9 | + | − | + | + | + | + | + |
| 317G5 | + | − | NT | + | + | − | + |
| 520C9 | NT | − | NT | − | NT | NT | + |
| 369F10 | − | − | NT | − | NT | NT | − |
| 650E2 | NT | − | NT | + | + | NT | + |

Cell line binding: + = positive; − = negative; NT = not tested.

The antibodies were tested by immunoperoxidase staining on eleven non-breast malignancies. The results for the subject antibodies are reported in Table 4 below.

*Biochem J* (1978) 173:723–737. SPDP (20 mM in ethanol) was added in a 20-fold molar excess to antibody and following a 30 min incubation at room temperature, the

TABLE 4

| ANTIBODY BINDING TO CANCERS* | | | | | | |
|---|---|---|---|---|---|---|
| Antibody | Colon | Lung | Prostate | Pancreas | Uterine | Lymphoma |
| 2G3 | 2 | 0 | 2 | 0 | 2 | 0 |
| 33F8 | 0 | 1 | 0 | 0 | 1 | 0 |
| 113F1 | 0 | 2 | 0 | 2 | 1 | 2 |
| 260F9 | 0 | 0 | 1 | 1 | 1 | 0 |
| 317G5 | 1 | 1 | 0 | 0 | 1 | 0 |
| 520C9 | 0 | 1 | 1 | 1 | 1 | 0 |
| 369F10 | 0 | 1 | 1 | 1 | 0 | 0 |
| 650E2 | 2 | 2 | 2 | 2 | 2 | 0 |
| Antibody | Stomach | Bladder | Esophagus | Melanoma | Ovarian | |
| 2G3 | 2 | 0 | 0 | 2 | 2 | |
| 33F8 | 0 | 0 | 0 | 0 | 1 | |
| 113F1 | 2 | 0 | 1 | 0 | 0 | |
| 260F9 | 0 | 0 | 1 | 0 | 2 | |
| 317G5 | 0 | 0 | 0 | 0 | 0 | |
| 520C9 | 0 | 0 | 0 | 0 | 0 | |
| 369F10 | 0 | 0 | 0 | 0 | 2 | |
| 650EZ | 0 | 0 | 0 | 0 | 2 | |

Staining intensity: 2 = strong; 1 = weak; 0 = negative. Only one tumor of each type examined.

unreacted SPDP was removed by dialysis against PBS. The extent of derivatization was determined by measuring the release of pyridine-2-thione at 343 nm after reduction with dithiothreitol (DTT). Depending on the antibody, three to eight lysine amino acid groups (per antibody molecule) were converted to the pyridyl-disulfide derivative.

The SPDP-treated antibodies were conjugated with ricin toxin A chain (RTA). Immediately prior to conjugation, the RTA was reduced with 50 mm DTT, then desalted on a Sephadex G-25 column to remove DTT from protein. Reduced RTA was added in a three- to five-fold molar excess over pyridyl-disulfide antibody. A typical reaction mixture (1 ml) consisted of 7 $\mu$M antibody and 30 $\mu$M RTA. The reaction was allowed to proceed overnight at 4° C. The extent of conjugation of RTA to antibody was determined spectrophotometrically by measuring the release of pyridine-2-thione. On the average, conjugates contained two to three RTA molecules per antibody molecule. This was confirmed by nonreducing SDS-PAGE gels (7.5%), which also revealed that the typical conjugate preparation contained 10%–30% free antibody.

The conjugate mixture was chromatographed on an HPLC size exclusion column (TSK-250, BioRad) to separate conjugates from residual unreacted RTA. The column was equilibrated in 0.1 M sodium sulfate/0.02 M sodium phosphate pH 6.8. Conjugate mixture (0.7 ml) was injected, then chromatographed at a flow rate of 1 ml/min (room temperature). Fractions of 0.5 ml were collected and the peak conjugate fractions were pooled and filter sterilized prior to cytotoxicity testing.

Forty thousand MCF-7 or CC95 (negative control) cells in 1 ml medium were added to a set of 8 ml glass vials, followed by the addition of conjugate dilutions (in PBS containing 100 $\mu$g/ml BSA). After incubation at 37° C. for 22 hr, the medium was aspirated, the monolayers were washed with PBS, and methionine-free medium supplemented with $^{35}$S methionine was added. The vials were further incubated 2 hr at 37° C., the medium was removed, and the cells were washed twice with 2 ml of 10% trichloroacetic acid containing 1 mg/ml methionine. The cells were dried, scintillation fluid was added, and the radioactivity was counted in a scintillation counter. Cytotoxicity was expressed as the tissue culture inhibitory dose of conjugate that resulted in 50% of control (untreated) protein synthesis (TCID 50%).

The results of these cytotoxicity tests are reported in Table 7 below.

TABLE 7

CYTOTOXICITY OF IMMUNOTOXINS

| Antibody | Ig Class | TCID 50% (nM) | | |
|---|---|---|---|---|
| | | MCF-7 | | CC95 |
| 260F9 | G1 | 0.11 | (0.06–0.19)* | >50 |
| 113F1 | G3 | 0.46 | (0.4–0.5) | >50 |
| 2G3 | G1 | 0.8 | (0.6–1.0) | >50 |
| 454C11 | G2a | 1.0 | | ND* |
| 280D11 | G1 | 1.4 | (0.8–2.9) | >50 |
| 266B2 | G1 | 2.7 | | ND |
| 33F8 | G1 | 5.6 | (1–9) | >50 |
| 245E7 | G1 | 5.9 | (0.6–15) | >50 |
| 274G6 | G3 | 10 | | >50 |
| 32A1 | G1 | >10 | | >50 |
| 44F4 | G3 | >10 | | >50 |
| 41B4 | G1 | >50 | | ND |
| 44B2 | G1 | >50 | | ND |
| 87H7 | G1 | >50 | | ND |
| 200F9 | G1 | >50 | | >50 |
| 219F3 | G1 | >50 | | >50 |

TABLE 7-continued

CYTOTOXICITY OF IMMUNOTOXINS

| Antibody | Ig Class | TCID 50% (nM) | |
|---|---|---|---|
| | | MCF-7 | CC95 |
| 106A10 | G1 | >50 | >50 |

*( ) gives the range of TCID 50%. ND means not determined.

Cytotoxicity was further evaluated as follows, for the antibodies shown in Table 8 (below). Approximately 30 mg/ml antibody in 0.10M Na phosphate, 0.001M Na EDTA, pH 8.0 (hereafter referred to as P-EDTA buffer) is reacted with 1 mM 5,5'-dithiobis-(2-nitrobenzoic acid) (DTNB) at room temperature for about 15 min and then chilled to 0° C. in an ice bath. Enough IT is added to this solution to give 2.5 IT molecules/antibody molecule, and the resulting solution is stored at 0°–5° C. against three 100-fold excess volumes of P-EDTA buffer.

RTA, normally stored in P-EDTA containing 1 mM DTT, is ultrafiltered to a concentration between 10 and 15 mg/ml and dialyzed at 0°–5° C. against three 100-fold excess volumes of P-EDTA. Enough RTA is added to the derivatized antibody to give 1.0–1.2 free thiols on RTA/blocked thiol on derivatized antibody. This mixture is incubated at room temperature for 2 hr.

The coupling reaction mixture is applied to a column of a chromatographic resin based on a blue dye hooked up to a solid support, which mixture is then eluted with P-EDTA at room temperature. The column is scaled to contain approximately 2 ml of bed volume per mg of starting antibody. After an initial peak of unconjugated antibody has been eluted from the column, the eulant is switched to P-EDTA containing 1M NaCl. Immunoconjugate and unreacted RTA are eluted in this buffer as a very sharp peak, which is pooled and dialyzed at 0°–5° C. against one 10-fold excess volume of 0.15M Na phosphate, pH 7.1 (hereafter referred to as $p_i$ buffer). The dialyzed protein is applied to a column of a gel at 0°–5° C. and eluted with buffer at a flow rate of 6 cm/hr. The column is scaled to contain at least 25 ml of bed volume/ml of applied protein. Immunoconjugate is eluted as a single peak, slightly after the excluded volume, baseline-resolved from following peaks of dimerized and monomeric RTA. The pooled immunoconjugate peak is ultrafiltered at 35 psi to a final concentration of 5.0 mg/ml and filter-sterilized.

The test human breast cancer lines used in the cytotoxicity tests were MCF-7, CAMA-1, SKBR-3, and BT-20. The human fibroblast cell lines CC95 and WI-38 were used as negative controls.

Forty thousand test cells in 1 ml medium were added to a set of 8 ml glass vials, followed by the addition of conjugate dilutions (in PBS containing 100 $\mu$g/ml BSA). After incubation at 37° C. for 22 hr, the medium was aspirated, the monolayers were washed with PBS, and methionine-free medium supplemented with $^{35}$S methionine was added. The vials were further incubated 2 hr at 37° C., the medium was removed, and the cells were washed twice with 2 ml of 10% trichloroacetic acid containing 1 mg/ml methionine. The cells were dried, scintillation fluid was added, and the radioactivity was counted in a scintillation counter. Cytotoxicity was expressed as the tissue culture inhibitory dose of conjugate that resulted in 50% of control (untreated) protein synthesis (TCID 50%).

The results of these cytotoxicity tests are reported in Table 8 below.

TABLE 8

Cytoxicity of Breast Tumor Immunotoxins

| RTA Conjugate | Isotype | TCID 50% (nM) | | | | | |
|---|---|---|---|---|---|---|---|
| | | MCF-7 | CAM-1 | SKBR-3 | BT-20 | CC95 | WI-38 |
| 260F9 | G1 | 0.1 | 0.4 | 0.06 | 9 | >50 | >50 |
| 317G5 | G1 | 0.4 | 5 | 10 | 2 | >50 | >50 |
| 113F1 | G3 | 0.5 | 0.6 | 10 | 6 | >50 | >50 |
| 2G3 | G1 | 0.8 | 1 | >50 | 15 | >50 | ND |
| 266B2 | G1 | 1 | 5 | 0.5 | 10 | >50 | ND |
| 280D11 | G1 | 1 | 1 | 0.9 | >40 | >50 | >50 |
| 245E7 | G1 | 6 | 8 | 8 | 4 | >50 | >50 |
| 454C11 | G2a | 6 | >20 | 0.3 | 30 | >50 | >50 |
| 33F8 | G1 | 10 | ND | ND | ND | ND | ND |
| 369F10 | M | 10 | ND | ND | ND | ND | ND |
| 520C9 | G1 | >50 | >50 | 10 | >50 | | |
| 452F2 | G1 | 20 | | 10 | | | |
| 736G9 | G1 | >50 | >50 | 1.3 | >50 | | |
| 741F8 | G1 | >80 | >80 | | >80 | | |
| 758G5 | G1 | >50 | | 0.3 | | | |
| 761B10 | G1 | >50 | | 1.0 | | | |

*ND means not determined.

Several of the antibodies were iodinated and tested for binding to MCF-7 or BT-20 cells. The antibodies were labeled with 125-I using chloramine T to a specific activity of approximately 10 $\mu$Ci/$\mu$g. To determine immunoradiochemical purity, 100,000 cpm of two of the labeled antibodies in 0.5 ml fetal calf serum was serially absorbed with five aliquots of target cells for 15 min at 0° C. (generally 4,000,000 MCF-7 breast cancer cells per aliquot), and the remaining radioactivity in the supernatant after each absorption was determined.

For measurements of association constants, known concentrations of labeled and unlabeled monoclonal antibodies were incubated with target cells in fetal calf serum for 15 min in ice. Aliquots of the cell/antibody mix were then counted in a gamma counter or filtered through Microfold® filter plates (V & P Scientific) and the filters counted. To account for unbound antibody retained in liquid on the filters, controls containing the same concentrations of antibody but no cells were done in parallel. Association constants and antigen copy number per target are calculated from the affinity test results and reported in Table 5 below.

TABLE 5

| Antibody | n | Ka | nKA |
|---|---|---|---|
| 2G3 | 3.7e6 | 9.1e6 | 3.4e13 |
| 113F1 | 2.3e6 | 1.1e9 | 2.5e15 |
| 260F9 | 3.1e5 | 5.6e7 | 1.7e13 |
| 317G5 | 3.2e6 | 1.6e6 | 5.1e12 |
| 520C9 | 5.0e5 | 8.2e6 | 4.1e12 | n = the antigen copy number per MCF-7 cell; ka = association constant on MCF-7. nKa is the product of n and Ka and relates antibody concentration to antibody bound per cell.

In order to identify the antigens recognized by the monoclonal antibodies, immunoprecipitation was carried out according to the following method. Eight mm diameter polystyrene balls (Precision Plastic Ball Co.) were covered with 10% fuming nitric acid in glacial acetic acid and were incubated for three hours in a 50° C. water bath. Following the acid treatment, the balls were rinsed three times with distilled water, covered with 1% sodium dithionite in 0.1 M NaOH and incubated for three hours in a 50° C. water bath. The balls were again rinsed three times with distilled water, covered with 0.1% 1-ethyl-3-(3-dimethylaminopropyl)-carbodiimide (EDAC), 0.2% suberic acid (suberic acid dissolved in dimethylformamide) and incubated overnight at room temperature. The balls were rinsed three times with distilled water, and marked for identification.

Purified monoclonal antibodies were diluted 0.2 mg/ml in 2-(N-morpholino)ethane sulfonic acid buffer, and the previously treated and marked polystyrene balls were placed in individual tubes and covered with 450 microliters diluted antibody and 50 microliters of fresh 1% EDAC. Tubes were capped and incubated at 25° C. for 24 hours. Following this incubation, the balls were rinsed twice with PBS and were either used fresh or were stored for several days at 4° C. before use.

Freshly labeled target cell extracts were prepared from human breast cancer cell lines labeled with 125-I by the lactoperoxidase method of Marchalonis, J. (1969) *Biochem. J.* 113:299–305, or with 35-S by growth in 35-S methionine. The labeled cells were dissolved in solubilization buffer (1% (v/v) Triton X-100, 150 mM NaCl, 5 mM EDTA, 25 mM Tris-HCl, pH 7.5). Four parts of labeled extract were mixed in a vessel with one part solubilization buffer containing 50 mg/ml bovine serum albumin, to give a final concentration of 10 mg/ml BSA. The balls coated with monoclonal antibody were added to the vessel and were incubated four hours on ice with shaking. Labeled antigen was pipetted from the vessel and the balls were rinsed four times with solubilization buffer. The balls were then removed, placed in individual tubes with 100 microliter Laemmli SDS gel sample buffer, and were incubated three minutes in boiling water. The balls were removed and the samples were run on an ADS gel with appropriate standards.

Immunoprecipitation tests on the antibodies indicated that two of them (2G3 and 369F10) bind to high molecular weight mucins (HMW mucins) present in cancerous human breast tissue. In this regard, HMW mucin antigens are also recognized by HMFG1, MC1 and B72.3 antibodies. See, e.g., Thor et al. (1986) *Cancer Res.* 46:3118–3124. The 260F9 antibody binds to an epitope of an approximately 55 kD glycoprotein antigen prevalent in cancerous human tissue. Two antibodies (317G5 and 650E2) bind to an approximately 42 kD antigen prevalent in cancerous colorectal tissue and other adenocarcinomas.

Immunoprecipitation tests on the antibodies indicated that seven of them (454C 11, 452F2, 520C9, 736G9, 741F8, 758G5, and 761B10) bind a common monomeric c.a. 210,000 dalton protein found in cancerous breast tissue. Six of the seven (452F2, 520C9, 736G9, 741F8, 75G5, and 7611B10) are believed to recognize the same epitope on the 210,000 dalton protein. Of these six, relative affinity studies indicated that 520C9 had the highest association constant. 452F2, 736G9, 741F8, 758G5, and 761B10 are considered to be functionally equivalent to 520C9. The 520C9 antibody binds an approximately 200 kD protein found in cancerous breast tissue which has been identified as c-erbB-2 (Ring et al. (1991) *Molec.* Immunol. 28:915). The 200 kd proteinaceous antigen bound by monoclonal antibody 520C9 is identical to the 210 kd antigen mentioned herein above, see, col.17, co-owned, U.S. Pat. No. 5,629,197. The 200 kd antigen bound by 520C9 and 454C11 was designated as the 210,000 dalton protein in U.S. Pat. No. 4,753,894. The 33F8 antibody binds to an approximately 66 kD antigen prevalent in cancerous human breast tissue. In immunoprecipitation experiments, the 113F1 antibody was found to recognize a number of diffuse bands with approximate molecular weights of 40, 60, 100 and 200 kD. These are suspected to be one or more glycoproteins bearing the same or similar carbohydrate. The antigen binding characteristics of the monoclonal antibodies that were tested are summarized below in Table 6.

TABLE 6

Antigens Recognized By Ovarian Monoclonal Antibodies

| | |
|---|---|
| 2G3 | HMW mucin |
| 33F8 | 66 Kd |
| 113F1 | 40, 60, 100, 200 Kd (diffuse bands) |
| 260F9 | 55 Kd |
| 317G5 | 42 Kd |
| 369F10 | TAG72 HMW mucin |
| 520C9 | 200 Kd (c-erbB-2) |
| 650E2 | 42 Kd |

The sequences of the variable regions from the heavy ($V_H$) and light ($V_L$) chains of monoclonal antibodies produced by the 2G3, 33F8, 113F1, 260F9, 317G5, 369F10, 520C9 and the 650E2 hybridoma cell lines were determined as follows. RNA encoding the heavy and light chains of each immunoglobulin was extracted from the subject hybridomas using standard methods involving cellular solubilization with guanidinium isothiocyanate (Chirgwin et al. (1979) *Biochem.* 18:5294–5299). The mRNA was then used to prepare cDNA for subsequent isolation of $V_H$ and $V_L$ genes by PCR methodology known in the art (Sambrook et al., eds., *Molecular Cloning* (1989) Cold Spring Harbor laboratories Press, N.Y.). The N-terminal amino acid sequence of the heavy and light chains can be independently determined by automated Edman sequencing. Further stretches of the CDRs and flanking FRs can also be determined by amino acid sequencing of the $V_H$ and $V_L$ fragments if necessary. Such sequence analysis is now conducted routinely. Synthetic primers were then designed for isolation of the $V_H$ and $V_L$ genes from the 2G3, 33F8, 113F1, 260F9, 317G5, 369F10, 520C9 and 650E2 monoclonal antibodies, and the isolated genes were ligated into an appropriate vector for sequencing, such as pBK-CMV, available from Stratagene (San Diego, Calif.) or the sequencing vector pUC19 (Yanisch-Perron (1985) *Gene* 33:103, available from ATCC (Manassas, Va.).

The Applied Biosystems Taq DyeDeoxy Terminator Cycle Sequencing®0 method was used to determine the sequences of the CDRs and FRs from the $V_H$ and $V_L$ domain of each of the 2G3, 33F8, 113F1, 260F9, 317G5, 369F10, 520C9 and 650E2 monoclonal antibodies. The method involves sequential enzymatic chain extension and termination reactions to produce a set of nested fragments which, when resolved, yield data from which a DNA sequence can readily be ascertained. Such techniques have been described in the art. See, e.g., Applied Biosystems Taq Dye Deoxy Terminator Cycle Sequencing P/N 901497. Rev. E; Connell et al. (1987) *BioTechniques* 5:342–348; Sanger et al. (1977) *Proc. Natl. Acad. Sci. USA* 74:5463–5467; Smith et al. (1986) *Nature* 321:674–679; and Gelfand, D. H. (1989) "Taq DNA polymerase", in *PCR Technology, Principles and Applications for DNA Amplification* (H. A. Erlich, ed.), Stockton Press, New York. The major steps of the method entail: (1) denaturation; (2) annealing; (3) chain extension; (4) chain termination; (5) several repeats of steps 1–4 to generate more fragments; (6) gel electrophoresis; and (7) detection. Denaturation involves separation of the template strands by exposure to heat. Annealing involves the hybridization of a synthetic oligonucleotide primer with the template DNA. By means of Taq polymerase, a synthetic DNA strand starting from the 3' end of the primer is enzymatically formed in the presence of four deoxynucleotide triphosphates (dNTP) and four dideoxynucleotide triphosphates (ddNTP) which are labeled with a dye specific for each base. The DNA strand is either elongated or terminated by the incorporation of dNTP or ddNTP, respectively. The double stranded molecules created can be used as "templates" for further cycles. After an optimal number of cycles, gel electrophoresis is used to resolve the synthesized DNA fragments. The DNA fragments on the gel are then detected by fluorescence in an ABI 373 Sequencer®, and the signals are analyzed by computer. With each primer, approximately 300 bases can be read.

The nucleic acid sequence and the predicted amino acid sequence of the $V_H$ encoding domain derived from 2G3, 33F8, 113F1, 260F9, 317G5 and 520C9 monoclonal antibodies are depicted in FIGS. 1, 3, 5, 7, 9 and 12, respectively. Proceeding from the amino terminus, the sequences of the three CDRs are generally indicated at HCDR1, HCDR2 and HCDR3; and the sequences of the four FRs are generally indicated at HFR1, HFR2, HFR3 and HFR4.

The nucleic acid sequence and the predicted amino acid sequence of the $V_L$ encoding domain derived from 2G3, 33F8, 113F1, 260F9, 317G5, 369F10, 520C9 and 650E2 monoclonal antibodies are depicted in FIGS. 2, 4, 6, 8, 10, 11, 13 and 14, respectively. Proceeding from the amino terminus, the sequences of the three CDRs are generally indicated at LCDR1, LCDR2 and LCDR3; and the sequences of the four FRs are generally indicated at LFR1, LFR2, LFR3 and LFR4.

Thus, one aspect of the invention involves the design and construction of a nucleic acid molecule comprising a plurality of nucleotide sequences which encode a monomeric polypeptide. The monomeric polypeptide exhibits immunological binding properties of an immunoglobulin prepared in response to an immunogen consisting essentially of membrane extracts derived from cancerous human breast tissue, or cells derived from a human cancer cell line selected from the group consisting of SKBr3, MCF7, BT20, ZR751, ZR7530 and MDAMB231. More particularly, the polypeptide includes a group of amino acid residues that are homologous to a set of CDRs derived from a variable region of a heavy or light chain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1, wherein the CDRs are interposed between flanking FR amino acid residues also derived from a variable region of a heavy or light chain of an antibody molecule.

In one particular embodiment, a nucleic acid molecule is provided which comprises a nucleotide sequence which is substantially homologous to the nucleotide sequence of a single $V_H$ domain derived from any one of the 2G3, 33F8, 113F1, 260F9, 317G5 and 520C9 monoclonal antibodies, which sequences are respectively depicted in FIGS. 1, 3, 5, 7, 9 and 12. In this manner, the nucleic acid molecule encodes a monomeric heavy chain variable domain polypeptide (e.g., half of an Fv comprising a single CDR set specific for an antigen interposed by a single flanking FR set) which has the ability to recognize and bind antigen, although at lower affinity than an entire antigen-binding site. See, e.g., Painter et al. (1972) *Biochem.* 11:1327–1337. The three CDRs (e.g., HCDR1, HCDR2 and HCDR3) in the monomeric variable domain polypeptide interact to define an antigen-binding region. The FRs flanking the CDRs impart a tertiary structure to the molecule which is essentially conserved in native human and murine immunoglobulins.

In another particular embodiment, a nucleic acid molecule is provided which comprises a nucleotide sequence which is substantially homologous to the nucleotide sequence of a single $V_L$ domain derived from any one of the 2G3, 33F8, 113F1, 260F9, 317G5, 369F10, 520C9 and 650E2 monoclonal antibodies, which sequences are respectively depicted in FIGS. 2, 4, 6, 8, 10, 11, 13 and 14. In this manner, the nucleic acid molecule encodes a monomeric light chain variable domain which also has the ability to recognize and bind antigen. The three CDRs (e.g., LCDR1, LCDR2 and LCDR3) in the monomeric variable domain polypeptide interact to define an antigen-binding region which is supported by the flanking FRs.

In a further aspect of the invention, a process for producing a monomeric heavy or light chain variable domain polypeptide is provided. Initially, an expression cassette is provided which comprises a nucleic acid molecule encoding either a $V_H$ or $V_L$ molecule as described above operably linked to a control sequence capable of directing the expression of the nucleic acid molecule. The expression cassette may further include an origin of replication for autonomous replication in a suitable host cell, one or more selectable markers, one or more restriction sites, a potential for high copy number and a strong promoter.

The expression cassette is placed into a suitable vector using molecular biology techniques well known in the art. See, e.g., Sambrook, et al., *Molecular Cloning: A Laboratory Manual* (2nd Edition, 1989); Maniatis et al., *Molecular Cloning: A Laboratory Manual* (1982); and *DNA Cloning: A Practical Approach*, vol. I & II (D. Glover, ed.). Suitable vectors include, but are not limited to, plasmids, phages, transposons, cosmids, chromosomes or viruses which are capable of replication when associated with the proper control elements and which can transfer the variable region gene sequences between cells.

Nucleic acid molecules comprising nucleotide sequences which are substantially homologous to either the nucleotide sequence of a single $V_H$ or $V_L$ domain derived from any one of the 2G3, 33F8, 113F1, 260F9, 317G5, 369F10, 520C9 and 650E2 monoclonal antibodies can thus be stably integrated into a host cell genome or maintained on a stable episomal element in a suitable host cell using various gene delivery techniques well known in the art. See, e.g., U.S. Pat. No. 5,399,346.

In yet a further embodiment of the invention, a coexpression system can be established in a suitable host cell. "Coexpression" as used herein refers to the expression of two or more polypeptides in a host cell. Thus, one such system comprises nucleic acid molecules encoding for monomeric $V_H$ and $V_L$ domain polypeptides which are harbored in a single plasmid, either under the control of the same regulatory elements or under the control of separate elements. Similarly, monomeric variable domain polypeptides expressed from the same vector but driven by separate regulatory elements would also be considered "coexpressed." In one particular embodiment, a coexpression system is provided by the expression of two or more polypeptides from separate constructs.

More particularly, suitable host cells can be transfected with two vectors; the first vector containing an expression cassette which includes nucleotide sequences substantially homologous to a nucleotide sequence encoding a $V_H$ domain polypeptide derived from any one of the 2G3, 33F8, 113F1, 260F9, 317G5, 369F10, 520C9 and 650E2 monoclonal antibodies, and the second vector containing an expression cassette which includes nucleotide sequences substantially homologous to a nucleotide sequence encoding a complementary $V_L$ domain polypeptide derived from the same monoclonal antibody. Generally, the vectors are identical—except in so far as the coding sequences and selectable markers are concerned—so as to ensure that the complementary $V_H$ and $V_L$ polypeptides are substantially equally expressed in the transfected host cell.

In this manner, a non-covalent heterodimer which exhibits immunological binding properties of an immunoglobulin which binds to a human tumor cell (expressing a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1) can be readily produced using a coexpression system. More particularly, a heterodimer can be formed by the coexpression of complementary $V_H$ and $V_L$ polypeptides in a transfected host cell. The coexpressed polypeptides dimerize under the influence of non-covalent (e.g., electrostatic) interdomain contacts to form an antigen-binding site. The dimeric molecule thus formed is substantially homologous to an Fv fragment isolated from a native immunoglobulin. In this regard, the heterodimer comprises six CDRs (a heavy chain CDR set and a light chain CDR set) disposed relative to each other in three dimensional space to form an antigen-binding surface. The antigen-binding surface is maintained by flanking FR residues to provide an antigen-binding site which retains much of the antigen recognition and binding capabilities of a native antibody molecule.

One particular heterodimer which can be produced using the coexpression system of the invention is characterized as an antigen-binding molecule having first and second polypeptide domains which are non-covalently associated via electrostatic, hydrophobic, or other non-covalent interdomain contacts between amino acid residues present in the subject polypeptide domains. The first polypeptide domain includes a first group of amino acid residues that are homologous to a CDR set which is derived from a $V_H$ domain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1, wherein the first group of residues are interposed between a plurality of flanking amino acid residues that are homologous to a FR set which is also derived from a $V_H$ domain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The second polypeptide domain includes a first group of amino acid residues that are homologous to a CDR set which is derived from a $V_L$ domain of an antibody capable of binding specifically to a human tumor antigen selected from the group consisting of the HMW mucins bound by 2G3 and 369Fl0, c-erbB-2 tumor antigen, an approximately 42 kD glycoprotein, an approximately 55 kD glycoprotein, and the approximately 40, 60, 100 and 200 kD antigens bound by 113F1, wherein the first group of residues are interposed between a plurality of flanking amino acid residues that are homologous to a FR set which is also derived from a $V_L$ domain of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. In one particular embodiment, the first and second polypeptide domains are derived from the $V_H$ and $V_L$ domains, respectively, of a monoclonal antibody produced by a hybridoma cell line selected from the group consisting of 2G3, 33F8, 113F1, 260F9, 317G5, 369F10, 520C9 and 650E2.

Polynucleotides encoding the monomeric $V_H$ or $V_L$ polypeptides can be introduced into a suitable insect host cell for expression using baculovirus systems. Materials and methods for baculovirus/insect cell expression systems are commercially available in kit form from, inter alia, Invitrogen, San Diego, Calif. ("MaxBac" kit). Baculovirus expression systems generally include a transfer vector, (e.g. a bacterial plasmid) which contains a fragment of the baculovirus genome, a wild-type baculovirus with a sequence homologous to the baculovirus-specific fragment in the transfer vector, and appropriate host insect cells. Such systems are known to those skilled in the art. See, e.g, Summers and Smith (1987) *Texas Agricultural Experiment Station Bulletin No.* 1555, (hereinafter "Summers and Smith").

A number of suitable baculovirus transfer vectors have been described and can include useful control sequences, such as the late promoter derived from the p10 protein (Vlak et al. (1988) *J. Gen. Virol.* 69:765), selectable markers, enhancer sequences and other suitable signal sequences. DNA encoding suitable signal sequences can be derived from genes for secreted insect or baculovirus proteins, such as the baculovirus polyhedrin gene (Carbonell et al. (1988) *Gene* 73:409), and leader sequences of non-insect origin, such as those derived from genes encoding human α-interferon (Maeda et al. (1985) *Nature* 315:592), human gastrin-releasing peptide (Lebacq-Verheyden et al. (1988) *Molec. Cell. Biol.* 8:3129), human IL-2 (Smith et al. (1985) *Proc. Natl Acad. Sci. USA* 82:8404), mouse IL-3 (Miyajima et al. (1987) *Gene* 58:273), and human glucocerebrosidase (Martin et al. (1988) *DNA* 7:99) to provide for secretion in insect host cells.

After insertion of coding sequences encoding the $V_H$ and/or $V_L$ molecules, a suitable host insect cell can be co-transfected with the heterologous DNA of the transfer vector and the genomic DNA of a wild-type baculovirus.

Methods for introducing heterologous DNA into a desired site in the baculovirus virus are known in the art. See, e.g., Summers and Smith supra; and Smith et al. (1983) *Mol. Cell. Biol.* 3:2156. For example, the insertion can be into a gene such as the polyhedrin gene, by homologous double crossover recombination. Insertion can also be into a restriction enzyme site engineered into the desired baculovirus gene. Miller et al. (1989) *Bioessays* 4:91.

The newly formed baculovirus expression vector can then be packaged into an infectious recombinant baculovirus. A number of recombinant baculovirus expression vectors have been developed for infection into various insect host cells. For example, recombinant baculoviruses have been developed for, inter alia: *Aedes aegypti, Autographa californica, Bombyx mori, Drosophila melanogaster, Spodoptera frugiperda*, and *Trichoplusia ni*. See, e.g., International Publication No. WO 89/046699; Carbonell et al. (1985) *J. Virol.* 56:153; Wright (1986) *Nature* 321:718; Smith et al. (1983) *Molec. Cell. Biol.* 3:2156; and Fraser, et al. (1989) *In Vitro Cell. Dev. Biol.* 25:225.

Cells infected with recombinant viruses are selected and cultured. Suitable host insect cells and cell culture media are commercially available for both direct and fusion expression of heterologous polypeptides in a baculovirus/expression system, and insect cell culture technology is generally known to those skilled in the art. See, e.g., Summers and Smith, supra.

Modified insect cells can thus be readily grown in an appropriate nutrient medium which allows for stable maintenance of the plasmid(s) present in the modified insect host. Where the expression product gene is under inducible control, the host can be grown to high density, and expression induced. Alternatively, where expression is constitutive, the $V_H$ and/or $V_L$ polypeptide product will be continuously expressed into the medium, and the nutrient medium must be continuously circulated to remove the product of interest and augment depleted nutrients. The $V_H$ and/or $V_L$ polypeptide product can then be purified by such techniques as chromatography, including HPLC, affinity chromatography, ion exchange chromatography; electrophoresis; density gradient centrifugation; solvent extraction, or like methods known in the art. As appropriate, the molecules can be further purified, as required, so as to remove substantially any insect proteins which are also secreted in the medium or result from lysis of insect cells.

Polynucleotides encoding the monomeric $V_H$ or $V_L$ polypeptides can also be introduced into a suitable mammalian host cell for expression or coexpression using a number of viral based systems which have been developed for gene transfer into mammalian cells. In this regard, retroviruses provide a convenient platform for gene delivery systems. A selected nucleotide sequence encoding a $V_H$ and/or a $V_L$ domain polypeptide can be inserted into a vector and packaged in retroviral particles using techniques known in the art. The recombinant virus can then be isolated and delivered to a subject. A number of suitable retroviral systems have been described (U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109. A number of suitable adenovirus vectors have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; and Rich et al. (1993) *Human Gene Therapy* 4:461–476). Various adeno-associated virus (AAV) vector systems have been developed recently for gene delivery. Such systems can include control sequences, such as promoter and polyadenylation sites, as well as selectable markers or reporter genes, enhancer sequences, and other control elements which allow for the induction of transcription. AAV vectors can be readily constructed using techniques well known in the art. See, e.g., U.S. Pat. Nos. 5,173,414 and 5,139,941; International Publication Nos. Wo 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Additional viral vectors which will find use for delivering the nucleic acid molecules encoding the variable domain molecules of the present invention by gene transfer include those derived from the pox family of viruses, such as vaccinia virus and avian poxvirus. By way of example, vaccinia virus recombinants expressing the novel molecules can be constructed as follows. The DNA encoding a $V_H$ and/or a $V_L$ domain polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting $TK^{(-)}$ recombinant can be selected by culturing the cells in the presence of 5-bromodeoxyuridine and picking viral plaques resistant thereto.

A vaccinia based infection/transfection system can be conveniently used to provide for inducible, transient expression or coexpression of the $V_H$ and/or $V_L$ domain molecules in a host cell. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747; Fuerst et al. *Proc. Natl. Acad. Sci. USA* (1986) 83:8122–8126.

Aternatively, Avipoxviruses, such as the fowlpox and canarypox viruses, can also be used to deliver the $V_H$ or $V_L$ domain coding sequences. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al. *J. Biol. Chem.* (1993) 268:6866–6869 and Wagner et al. *Proc. Natl. Acad. Sci. USA* (1992) 89:6099–6103, can also be used for gene delivery under the invention.

Vectors encoding the subject $V_H$ and/or $V_L$ molecules can also be packaged in liposomes prior to delivery to the vertebrate subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight *Biochim. Biophys. Acta.* (1991) 1097:1–17; and Straubinger et al. in *Methods of Enzymology* (1983), Vol. 101, pp. 512–527.

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner et al. *Proc. Natl. Acad. Sci. USA* (1987) 84:7413–7416); mRNA (Malone et al. *Proc. Natl. Acad. Sci. USA* (1989) 86:6077–6081); and purified transcription factors (Debs et al. *J. Biol. Chem.* (1990) 265:10189–10192), in functional form.

Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. (See, also, Felgner et al. *Proc. Natl. Acad. Sci. USA* (1987) 84:7413–7416). Other commercially available liposomes include transfectase (DDAB/DOPE) and DOTAP/DOPE (Boehringer). Other cationic liposomes can be prepared from readily available materials using techniques well known in the art. See, e.g., Szoka et al. *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger et al. in *Methods of Immunology* (1983), Vol. 101, pp. 512–527; Szoka et al. *Proc. Natl. Acad. Sci. USA* (1978) 75:4194–4198; Papahadjopoulos et al. *Biochim. Biophys. Acta* (1975) 394:483; Wilson et al. *Cell* (1979) 17:77); Deamer and Bangham *Biochim. Biophys.*

*Acta* (1976) 443:629; Ostro et al. *Biochem. Biophys. Res. Commun.* (1977) 76:836; Fraley et al. *Proc. Natl. Acad. Sci. USA* (1979) 76:3348); Enoch and Strittmatter *Proc. Natl. Acad. Sci. USA* (1979) 76:145); Fraley et al. *J. Biol. Chem.* (1980) 255:10431; Szoka and Papahadjopoulos *Proc. Natl. Acad. Sci. USA* (1978) 75:145; and Schaefer-Ridder et al. *Science* (1982) 215:166.

Thus, a number of nucleic acid molecules which comprise nucleotide sequences encoding polypeptides that are substantially homologous to $V_H$ and/or $V_L$ domains of an antibody capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The subject nucleic acid molecules may be expressed or coexpressed to provide monomeric or heterodimeric polypeptides, respectively. In particular embodiments, the polypeptides are derived from $V_H$ and/or $V_L$ domains of a monoclonal antibody produced by any one of the 2G3, 33F8, 113F1, 260F9, 317G5, 369F10, 520C9 and 650E2 hybridoma cell lines.

In another aspect of the invention, standard techniques of molecular biology can be used to prepare nucleic acid molecules encoding synthetic or recombinant polypeptides derived from antibody $V_H$ or $V_L$ domains. Particular nucleotide sequences can be synthesized completely or in part using various oligonucleotide synthesis techniques known in the art, such as site-directed mutagenesis and polymerase chain reaction (PCR) techniques where appropriate. See, e.g., Sambrook, and Maniatis, supra. In particular, one method of obtaining nucleotide sequences encoding the FR and CDR sequences disclosed herein is by annealing of complementary sets of overlapping synthetic oligonucleotides produced in a conventional, automated polynucleotide synthesizer, followed by ligation with an appropriate DNA ligase and amplification of the ligated nucleotide sequence via PVR. See, e.g., Jayaraman et al. (1991) *Proc. Natl. Acad. Sci. USA* 88:4084–4088. Additionally, oligonucleotide directed synthesis (Jones et al. (1986) *Nature* 54:75–82), oligonucleotide directed mutagenesis of pre-existing nucleotide regions (Riechmann et al. (1988) *Nature* 332:323–327 and Verhoeyen et al. (1988) *Science* 239:1534–1536), and enzymatic filling in of gapped oligonucleotides using $T_4$ DNA polymerase (Queen et al. (1989) *Proc. Natl. Acad. Sci. USA* 86:10029–10033) can be used under the invention to provide molecules having altered or enhanced antigen-binding capabilities, and/or reduced immunogenicity.

In one particular embodiment of the invention, knowledge of the nucleotide sequences of the $V_H$ domains of antibody molecules produced by the 2G3, 33F8, 113F1, 260F9, 317G5, 369F10, 520C9 and 650E2 hybridoma cell lines allows for selective optimization of binding affinity in antigen-binding sites produced with those moieties. In this regard, point substitutions can be made in one or more CDRs using conventional cassette mutagenesis or other molecular biology techniques to enhance binding capabilities of an antigen-binding site.

Further, in a related embodiment, entire CDRs may be selectively shuttled into and out of a $V_H$ or $V_L$ coding sequence using recombinant methods known in the art. More particularly, the presence of restriction sites in regions flanking the CDRs makes it possible to cleave one or more CDRs from a molecule. Such restriction sites may in some cases be found in the native coding sequence. Aternatively, recombinant techniques can be used to engineer unique restriction sites into the nucleotide sequences resulting in a synthetic gene which encodes the same V region amino acid sequence due to the degeneracy of the genetic code. Fragments resulting from endonuclease digestion of the V domain nucleotide sequences which comprise the flanking FR-encoding sequences are then ligated to replacement CDR-encoding sequences to provide a synthetic variable domain molecule which displays an altered antigen binding specificity.

Replacement CDR-encoding sequences can be designed empirically under the invention based on sequence analysis of the Fv region of preexisting antibodies. Further, using a computer program such as, for example, Compugenes, and known variable region DNA sequences, those of ordinary skill in the art can design and directly synthesize native or near-native CDR-encoding sequences.

Using transfection and gene delivery techniques as described above, replacement CDR sequences can be readily expressed and the resultant polypeptides tested for binding and empirically refined by exchanging selected amino acids in relatively conserved regions based on observation of trends in amino acid sequence data and/or computer modeling techniques. Thus, significant flexibility in $V_H$ and $V_L$ molecule design is possible under the invention because alterations in amino acid sequences can be made at the DNA level.

Accordingly, in one particular embodiment of the invention, a monomeric $V_H$ domain polypeptide derived from an antibody molecule produced by any one of the 2G3, 33F8, 113F1, 260F9, 317G5, 369F10, 520C9 and 650E2 hybridoma cell lines is provided wherein the polypeptide has one CDR selected from the group consisting of HCDR1, HCDR2 and HCDR3. The CDR set in the molecule is completed by two CDRs wherein point substitutions have been introduced into native CDR sequences using conventional cassette mutagenesis, or wherein the CDR comprises a synthetic replacement CDR.

In a related embodiment, a monomeric $V_H$ domain polypeptide derived from an antibody molecule produced by any one of the 2G3, 33F8, 113F1, 260F9, 317G5, 369F10, 520C9 and 650E2 hybridoma cell lines is provided, wherein the polypeptide has two CDRs selected from the group consisting of HCDR1, HCDR2 and HCDR3. The third CDR comprises either a point substituted native CDR sequence or a synthetic CDR.

In another particular embodiment of the invention, a monomeric $V_L$ domain polypeptide derived from an antibody molecule produced by any one of the 2G3, 33F8, 113F1, 260F9, 317G5, 369F10, 520C9 and 650E2 hybridoma cell lines is provided wherein the polypeptide has one CDR selected from the group consisting of LCDR1, LCDR2 and LCDR3. The CDR set in the molecule is completed by two CDRs wherein point substitutions have been introduced into native CDR sequences using conventional cassette mutagenesis, or wherein the CDR comprises a synthetic replacement CDR.

In a related embodiment, a monomeric $V_L$ domain polypeptide derived from an antibody molecule produced by any one of the 2G3, 33F8, 113F1, 260F9, 317G5, 369F10, 520C9 and 650E2 hybridoma cell lines is provided wherein the polypeptide has two CDRs selected from the group consisting of LCDR1, LCDR2 and LCDR3. The third CDR comprises either a point substituted native CDR sequence or a synthetic CDR.

In another aspect of the invention, an isolated nucleic acid molecule is provided which comprises a nucleotide sequence encoding a single molecular recognition unit.

More particularly, the nucleotide sequence encodes an amino acid sequence that is homologous to a CDR derived from a $V_H$ or $V_L$ domain of an antibody molecule capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. In a particular embodiment, the molecular recognition unit is homologous to a CDR selected from the $V_H$ or $V_L$ domain of an antibody molecule produced by any one of the 2G3, 33F8, 113F1, 260F9, 317G5, 369F10, 520C9 and 650E2 hybridoma cell lines.

The isolated nucleic acid molecule therefore consists essentially of a single coding sequence for the selected CDR; however, the molecule may also include some additional bases or moieties which do not deleteriously affect the basic characteristics of the CDR such as, but not limited to, flanking nucleotide sequences comprising unique restriction sites to enable ligation of nucleotides encoding the subject molecular recognition units into an appropriate site of an antibody variable domain-encoding molecule using recombinant techniques known in the art.

In further related embodiments of the invention, nucleic acid molecules are provided which comprise a plurality of nucleotide sequences, each encoding a molecular recognition unit comprising an amino acid sequence homologous to a CDR derived from a $V_H$ or $V_L$ domain of an antibody molecule capable of binding specifically to a human tumor antigen selected from the group consisting of the HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. In one embodiment, each molecular recognition unit is homologous to a CDR selected from the $V_H$ or $V_L$ domain of an antibody molecule produced by any one of the 2G3, 33F8, 113F1, 260F9, 317G5, 369F10, 520C9 and 650E2 hybridoma cell lines.

In yet a further aspect of the invention, knowledge of the nucleotide sequences of the $V_H$ and $V_L$ domains of an antibody molecule produced by the 2G3, 33F8, 113F1, 260F9, 317G5, 369F10, 520C9 and 650E2 hybridoma cell lines allows for the construction of synthetic nucleic acid molecules comprising nucleotide sequences which encode CDRs flanked by recombinantly engineered polypeptide regions. In one embodiment, a nucleic acid molecule is provided which includes nucleotide sequences encoding either a heavy or light chain V domain having a CDR set derived from the $V_H$ or $V_L$ domain of an antibody molecule produced by any one of the 2G3, 33F8, 113F1, 260F9, 317G5, 369F10, 520C9 and 650E2 hybridoma cell lines. The encoded CDRs are flanked by FRs derived from a heavy or light chain, respectively, of a human immunoglobulin. The resultant xenogeneic chimeric molecule displays immunological binding characteristics imparted by the murine antibody-derived CDRS, but has reduced immunogenicity in humans due to the human antibody-derived FRs. See, e.g., Riechmann et al. (1988) *Nature* 332:323–327; Verhoeyen et al. (1988) *Science* 239:1534–1536; and Jones et al. (1986) *Nature* 321:522–525.

Thus, under the invention, the coexpression of two nucleic acid molecules in a suitable host cell; where the first molecule includes nucleotide sequences encoding a CDR set derived from the $V_H$ domain of a murine antibody produced by any one of the 2G3, 33F8, 113F1, 260F9, 317G5, 369F10, 520C9 and 650E2 hybridoma cell lines, wherein the encoded CDRs are flanked by FRs derived from a heavy chain of a human immunoglobulin, and the second molecule includes nucleotide sequences encoding a CDR set derived from the complementary $V_L$ domain of the same murine monoclonal antibody, wherein the encoded CDRs are flanked by FRs derived from a light chain of a human immunoglobulin; provides a convenient method of producing a heterodimeric polypeptide—having an antigen-binding site that binds specifically to a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1—and which is weakly-immunogenic or non-immunogenic in a human recipient.

In a further related embodiment, a nucleic acid molecule is provided which comprises a nucleotide sequence encoding a CDR selected from the group consisting of HCDR1, HCDR2, HCDR3, LCDR1, LCDR2 and LCDR3 (derived from one of the 2G3, 33F8, 113F1, 260F9, 317G5, 369F10, 520C9 and 650E2 monoclonal antibodies), wherein the CDR sequence is interposed by first and second flanking nucleotide sequences. In a particular embodiment, the flanking nucleotide sequences encode FRs derived from murine or human antibody heavy or light chain variable domains. Also provided herein are nucleic acid molecules which comprise a plurality of CDR-encoding sequences selected from the group consisting of HCDR1, HCDR2, HCDR3, LCDR1, LCDR2 and LCDR3 (derived from one of the 2G3, 33F8, 113F1, 260F9, 317G5, 369F10, 520C9 and 650E2 monoclonal antibodies), wherein the CDRs are interposed by flanking nucleotide sequences derived from murine or human antibody $V_H$ and $V_L$ domains.

Each of the above-described synthetic DNAs are used under the invention to facilitate the empirical refinement of recombinant amino acid sequences encoded by combinations of those nucleic acid molecules to provide synthetic molecules having particularly desired antigen-binding properties. The recombined nucleic acid molecules can be expressed directly in an appropriate host cell, or can be further engineered before expression by the exchange of CDR, FR and FR:CDR:FR sequences with new sequences. CDR and/or FR exchange manipulations are facilitated by PCR techniques (e.g., overlap methods) well known in the art. Such methods generally entail the synthesis of staggered overlapping oligomers including CDR and/or FR sequences derived from both heavy and light chain variable domains using known techniques. The subject oligomers are annealed, ligated and then subjected to PCR amplification using terminal sequences as primers. Jayaraman et al. (1991) *Proc. Natl. Acad. Sci. USA* 8:4084–4088. Other exchange methods are facilitated by the presence of restriction sites which can be engineered into the subject nucleic acid molecules at the FR-CDR and CDR-FR borders.

In yet another aspect of the invention, standard techniques of molecular biology can be used to prepare nucleic acid molecules encoding synthetic or recombinant polypeptides derived from antibody $V_H$ or $V_L$ domains wherein the molecules comprise murine CDRs interposed by flanking recombinantly veneered FR polypeptide regions. The veneering process used herein has been described in the art (see, European Patent Publication No. 519,596, published Dec. 23, 1992, and International Publication No. WO 92/22653, published Dec. 23, 1992, incorporated herein by reference in their entireties).

In one particular embodiment, a synthetic nucleic acid molecule is provided including nucleotide sequences encoding a CDR set derived from the $V_H$ domain of an antibody molecule produced by any one of the 2G3, 33F8, 113F1, 260F9, 317G5, 369F10, 520C9 and 650E2 hybridoma cell lines, wherein the CDRs are flanked by recombinantly veneered FR sequences derived from the $V_H$ domain of the same antibody molecule. Thus, the molecule includes three CDR sequences comprising HCDR1, HCDR2 and HCDR3 that encode CDRs which are supported relative to each other to form an antigen-binding region by flanking veneered FRs.

In a related embodiment, a synthetic nucleic acid molecule is provided including nucleotide sequences encoding a CDR set derived from the $V_L$ domain of an antibody molecule produced by any one of the 2G3, 33F8, 113F1, 260F9, 317G5, 369F10, 520C9 and 650E2 hybridoma cell lines, wherein the CDRs are flanked by recombinantly veneered FRs derived from the $V_L$ domain of the same antibody molecule. Thus, the molecule includes three CDR sequences comprising LCDR1, LCDR2 and LCDR3 that encode CDRs which are supported relative to each other to form an antigen-binding region by flanking veneered FRs.

The veneering method used herein to provide the above-described synthetic molecules includes the following steps. Initially, the FR sequences derived from the $V_H$ and $V_L$ domains of an antibody molecule produced by any one of the 2G3, 33F8, 113F1, 260F9, 317G5, 369F10, 520C9 and 650E2 hybridoma cell lines are compared with corresponding FR sequences of human variable domains obtained from an appropriate database. See, e.g., Kabat et al., in *Sequences of Proteins of Immunological Interest*, 4th ed., (U.S. Dept. of Health and Human Services, U.S. Government Printing Office, 1987). Human frameworks with a high degree of sequence similarity to those of the murine regions are identified. Sequence similarity is measured using identical residues as well as evolutionarily conservative amino acid substitutions. Similarity searches are performed using the selected murine framework sequence from which the CDRs have been removed. The framework sequence is used to query a database of human immunoglobulin sequences derived from multiple sources. Sequences with a high degree of sequence similarity are examined individually for their potential as humanizing framework sequences. In this way, the human homologue providing the CDRs from the selected 2G3, 33F8, 113F1, 260F9, 317G5, 369F10, 520C9 or 650E2 molecule with the structure most similar to their native murine framework is selected as the template for the construction of the veneered FRs.

The selected human V regions are then compared residue by residue to the corresponding murine amino acids. The residues in the murine FRs which differ from the selected human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" FRs are designed to retain the murine CDR residues, the residues substantially adjacent to the CDRS, the residues identified as buried or mostly buried (solvent inaccessible), the residues believed to participate in non-covalent (e.g., electrostatic) interchain contacts, and the residues from conserved structural regions of the FRs which are believed to influence the "canonical" tertiary structures of the CDR loops.

Accordingly, recombinant nucleotide sequences which combine CDRs derived from an antibody molecule produced by any one of the 2G3, 33F8, 113F1, 260F9, 317G5, 369F10, 520C9 and 650E2 hybridoma cell lines with the human-appearing veneered FRs can be introduced into suitable host cells for the expression of recombinant human antibodies which exhibit the antigen specificity of the murine antibody molecule. More particularly, expression cassettes, comprising polynucleotide sequences encoding the subject recombinant molecules—operably linked to a control sequence that is capable of directing the expression thereof—can be introduced into a suitable host cell for expression using standard gene transfer protocols. The subject polypeptides can thus be expressed in appropriate prokaryotic or eukaryotic hosts as described above. Additionally, coexpression of complementary $V_H$ and $V_L$ molecules having veneered frameworks provides a convenient method of producing a heterodimeric polypeptide—featuring an antigen-binding site that binds specifically to a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1—and which is weakly-immunogenic, or substantially non-immunogenic in a human recipient.

Each of the synthetic molecules described herein may be expressed using a monovalent phage display system as described by Garrad et al. (1991) *Biotechnology* 9:1373–1377, to identify $V_H/V_L$ pairs with a desired specificity or to modify the specificity or affinity of a given $V_H/V_L$ pair. In this regard, improvement of antigen binding affinity of a given $V_H/V_L$ pair can be accomplished by constructing phage libraries—in which at least one CDR comprises a synthetic or point mutated CDR—and screening the phage system for molecules which exhibit enhanced binding characteristics or lower off rates using ligand affinity analysis methods well known in the art. Additionally, a phage display system can be used under the invention to facilitate "chain shuffling" in which a given $V_H$ or $V_L$ is re-paired with a library of random $V_H$ or $V_L$ sequences and the resulting phage screened for desired antigen binding behavior. Suitable phage display systems have been described (McCafferty et al. (1990) *Nature* 348:552–554), and chain shuffling techniques are known in the art. See, e.g., Figini et al. (1994) *J. Mol. Biol.* 239:68–78.

In another aspect of the invention, biosynthetic single-chain Fv (sFv) molecules are provided. The sFv polypeptides are termed "biosynthetic" in the sense that they are synthesized and re-cloned in a cellular host made to express a protein encoded by a plasmid which includes a coding sequence based in part on synthetic DNA, that is, a recombinant DNA made from ligation of plural, chemically synthesized and re-cloned oligonucleotides, or by ligation of fragments of DNA derived from the genome of any one of the 2G3, 33F8, 113F1, 260F9, 317G5, 369F10, 520C9 and 650E2 hybridomas. The sFv molecules are properly characterized as "antibody binding sites" in that the synthetic single polypeptide chains are able to refold into a 3-dimensional conformation designed specifically to have affinity for a human tumor antigen selected from the group consisting of HMW mucins bound by 2G3 and 369F10, c-erbB-2 tumor antigen, an approximately 42 kD glycoprotein, an approximately 55 kD glycoprotein, the approximately 40, 60, 100 and 200 kD antigens bound by 113F1, or related tumor antigens. The inventive sFv molecules are produced herein using methods described in the art. See, e.g., Huston et al. (1988) *Proc. Nat. Acad. Sci. USA* 85(16):5879–5883; U.S. Pat. Nos. 5,091,513 and 5,132,405, to Huston et al.; and U.S. Pat. No. 4,946,778, to Ladner et al.

In one particular embodiment, an sFv molecule is provided wherein the CDRs and FRs are derived from an antibody molecule capable of binding specifically to a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The subject sFv polypeptide includes a series of residues consisting of amino acids defining at least three polypeptide segments which together form the tertiary molecular structure responsible for affinity and binding. The CDRs are held in appropriate conformation by polypeptide segments analogous to the FRs of a Fv fragment derived from a native antibody molecule.

More particularly, an isolated nucleic acid molecule is provided having a nucleotide sequence encoding a sFv polypeptide that exhibits antibody-binding specificity of an antibody capable of binding to a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. The sFv molecule comprises first, second and third domains; wherein the first polypeptide domain has an amino acid sequence that is homologous to a $V_H$ domain of an antibody molecule, the second polypeptide domain has an amino acid sequence that is homologous to a $V_L$ domain of an antibody molecule, and the third polypeptide domain comprises an amino acid sequence spanning the distance between the C-terminus of one of the first or second domains and the N-terminus of the other to provide a single chain polypeptide.

In one particular embodiment, the sFv molecule comprises a first polypeptide domain that comprises an amino acid sequence homologous to the $V_H$ domain of an antibody produced by any one of the 2G3, 33F8, 113F1, 260F9, 317G5, 369F10, 520C9 and 650E2 hybridoma cell lines, and the second polypeptide domain comprises an amino acid sequence that is homologous to a complementary $V_L$ domain from the same antibody. The first and second polypeptide domains are linked together by a polypeptide linker that is not necessarily derived from an antibody molecule.

Under the invention, recombinant design methods can be used to develop suitable chemical structures (linkers) for converting two naturally associated—but chemically separate—heavy and light polypeptide chains from an antibody variable region into a sFv molecule which will fold into a three-dimensional structure that is substantially similar to native antibody structure. Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. One particular linker under the invention has the amino acid sequence $[(Gly)_4Ser]_3$(SEQ ID NO: 29). Another particularly preferred linker has the amino acid sequence comprising 2 or 3 repeats of $[(Ser)_4Gly]$(SEQ ID NO: 30), such as $[(Ser)_4Gly]_3$ (SEQ ID NO: 31). Nucleotide sequences encoding such linker moieties can be readily provided using various oligonucleotide synthesis techniques known in the art. See, e.g., Sambrook, and Maniatis, supra.

In further related embodiments, nucleic acid molecules encoding various synthetic antibody variable domain moieties can be combined to provide sFv molecules comprising murine CDRs supported by human frameworks, antigen-binding sites having recombinantly veneered heavy and light chain FRs, and re-paired CDRs and/or CDR sets as described above. Accordingly, the construction of nucleic acid molecules including nucleotide sequences encoding the single-chain Fv and sFv fusion molecules of the invention can be practiced using known techniques. Such methods include the use of various restriction enzymes which make sequence-specific cuts in DNA to produce blunt ends or cohesive ends, DNA ligases, techniques enabling enzymatic addition of sticky ends to blunt-ended DNA, construction of synthetic polynucleotides by assembly of short or medium length oligonucleotides, cDNA synthesis techniques, and synthetic probes for isolating immunoglobulin genes.

In particular, one method of obtaining nucleotide sequences encoding the sFv molecules disclosed herein is by an overlap PCR approach. See, e.g., Horton et al. (1990) *BioTechniques* 8:528–535. The ends of the light and heavy chain variable regions that are to be joined through a linker sequence are first extended by PCR amplification of each variable region, using primers that contain the terminal sequence of the variable region followed by all or most of the desired linker sequence. After this extension step, the light and heavy chain variable regions contain overlapping extensions which jointly contain the entire linker sequence, and which can be annealed at the overlap and extended by PCR to obtain the complete sFv sequence using methods known in the art.

Practice of the invention enables the design and biosynthesis of a wide variety of molecules, all of which are characterized by a region having affinity for a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1. Additional regions of the biosynthetic proteins are designed with the particular planned utility of the molecule in mind. Thus, if the molecule is designed for intravascular use in mammals, the FRs may include amino acid sequences that are similar, or identical to at least a portion of immunoglobulin FRs native to that mammalian species.

More particularly, the invention includes the use of sFv molecules and humanized sFv binding sites in diagnostic imaging methods and tumor therapies. The subject molecules can be administered by intravenous or intramuscular injection. Effective dosages for the sFv constructs in anti-tumor therapies or in effective tumor imaging can be determined by routine experimentation, keeping in mind the objective of the treatment.

Pharmaceutical forms suitable for injectable use include sterile aqueous solutions or dispersions. In all cases, the form must be sterile and must be fluid so as to be easily administered by syringe. The sFv molecules must further be stable under the conditions of manufacture and storage, and must be preserved against the contaminating action of microorganisms. This may, for example, be achieved by filtration through a sterile 0.22 micron filter and/or lyophilization followed by sterilization with a gamma ray source.

Sterile injectable solutions are prepared by incorporating the single chain polypeptide constructs of the invention in the required amount in the appropriate solvent, such as sodium phosphate-buffered saline, followed by filter sterilization. As used herein, "a physiologically acceptable carrier" includes any and all solvents, dispersion media, antibacterial and antifungal agents that are non-toxic to humans, and the like. The use of such media and agents for pharmaceutically active substances is well known in the art. The media or agent must be compatible with maintenance of proper conformation of the single polypeptide chains, and its use in the therapeutic compositions. Supplementary active ingredients can also be incorporated into the compositions.

The above-described biosynthetic sFv molecules (having affinity for a human tumor antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1) can be used to develop retroviral vectors that target human cancer cells expressing those antigens, and are thus useful in the design and development of gene therapy strategies. In this regard, mammalian retrovirus vectors commonly used for gene transfer are capable of infecting a host range determined primarily by the binding interaction between viral envelope glycoproteins and specific proteins on the host cell surface that act as viral receptors. Varmus, H. (1988) *Science* 240:1427; and Weiss et al., eds., *RNA Tumor Viruses: Molecular Biology of Tumor Viruses* (Cold Spring Harbor Laboratory, Cold Spring Harbor, N.Y., 1984). It has been demonstrated that the host range of viruses can be altered by pseudotyping, using alternative envelope proteins derived from naturally occurring viral sequences such as those of the avian leukosis virus and the human immunodeficiency virus. Wilson et al. (1989) *J. Virol.* 63:2374. Recently, the polypeptide hormone erythropoietin (EPO) has been introduced into the ecotropic Moloney murine leukemia virus (Mo-MuLV) envelope. Kasahara et al. (1994) *Science* 266:1373. The resultant murine virus became several times more infectious for murine cells bearing the EPO receptor, and also became infectious for human cells bearing the EPO receptor, indicating that tissue-specific targeting using recombinantly engineered viral envelopes has broad application in a variety of gene delivery systems.

A recombinant virus containing in its envelope a sequence encoding a sFv molecule including an antigen-binding site has been shown to bind to a solid matrix containing the appropriate polypeptide antigen, and the bound viruses were infectious for NIH 3T3 cells. Russell et al. (1993) *Nucl. Acids Res.* 21:1081. Thus, in one embodiment of the invention, the nucleic acid molecules provided under the invention can be recombinantly engineered into various retroviral systems (U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109), using recombinant techniques known in the art. The nucleic acid molecules of the invention can also be engineered into a suitable adenovirus vector, such as those which have been described in the art. (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; and Rich et al. (1993) *Human Gene Therapy* 4:461–476). The methods generally entail removal of a portion of a viral envelope gene and replacement, in frame, with nucleotide sequences encoding the polypeptides of the invention. The constructs can be cotransfected into appropriate packaging cells, and transfected cells selected and screened using known techniques. Cells containing correctly oriented chimeric envelope proteins can then be selected and isolated, and virus-producing cell lines generated by infection of packaging cells with virion-containing cell culture medium harvested after transient transfection with wild-type packaging cells using known techniques. See, e.g., Miller et al. (1986) *Molec. Cell. Biol.* 6:2895; Bender et al. (1987) *J. Virol.* 61:1639; Eglitis et al. (1988) *BioTechniques* 6:608; and Mann et al. (1983) *Cell* 33:153.

The single chain polypeptide motif of sFv molecules formed under the invention provides a convenient means for designing multi-functional molecules such as immunotoxins and the like. In this regard, additional nucleotide sequences encoding, for example, antibody constant region fragments can be linked to sFv coding sequences to provide a bifunctional molecule. The single polypeptide chains of the invention may also include ancillary polypeptide regions defining a leader sequence or a second polypeptide chain that is bioactive such as a cytokine, toxin, ligand, hormone, or enzyme, or a site onto which a toxin, drug, or a remotely detectable moiety can be attached.

Thus, in a further aspect of the invention, a nucleic acid molecule is provided that encodes a sFv polypeptide comprising a third polypeptide domain. The third polypeptide domain is joined to either the first or second polypeptide domain by a second polypeptide linker moiety spanning the distance between the C-terminus or N-terminus of one of the first or second domains, and the N-terminus or C-terminus, respectively, of the third polypeptide domain.

In one embodiment, the third polypeptide domain comprises a second antigen-binding site. The second antigen-binding site is formed from a first portion derived from a $V_H$ domain of an antibody, a second portion derived from a $V_L$ domain of an antibody and a third portion comprising a polypeptide linker spanning the distance between the C-terminus of one of the first or second portions and the N-terminus of the other, whereby the linker joins the first and second portions to define a second antigen-binding site which is capable of immunological binding activity. In one embodiment, the CDRs in the first and second portions of the third polypeptide domain are derived from an antibody produced by any one of the 2G3, 33F8, 113F1, 260F9, 317G5, 369F10, 520C9 and 650E2 hybridoma cell lines.

In another embodiment, the third polypeptide domain comprises at least a portion of a human or murine antibody Fc polypeptide. More particularly, a sFv-encoding nucleic acid molecule is provided under the invention wherein an attached nucleotide sequence encodes an ancillary amino acid sequence homologous to an Fc polypeptide fragment such as an IgG fragment, whereby the third polypeptide region is capable of binding IgG-isotype specific Fc receptors. In one particular embodiment, the third polypeptide-encoding sequence encodes a Fc fragment derived from a human IgG molecule, or a peptide sequence substantially homologous thereto.

In a related embodiment, a sFv molecule is provided wherein the molecule is fused to a third polypeptide domain comprising an amino acid sequence derived from the transmembrane and cytoplasmic domain of the ζ chain of the T-cell receptor CD3 complex. More particularly, a chimeric nucleic acid molecule is provided which includes a nucleotide sequence encoding a sFv molecule as described above fused to a nucleotide sequence encoding a polypeptide which is substantially homologous to the ζ chain of the CD3 complex. See e.g., U.S. Pat. No. 5,359,046. In this regard, it has been shown that the cytoplasmic tail of the ζ chain can activate T cells independently of the rest of the receptor complex. Letourneur et al. (1992) *Science* 255: 79–82. Thus, in one embodiment, a nucleic acid molecule is provided comprising a nucleotide sequence encoding a sFv molecule, said sFv molecule having first and second polypeptide domains derived from the $V_H$ and $V_L$ domain, respectively, of an antibody produced by any one of the 2G3, 33F8, 113F1, 260F9, 317G5, 369F10, 520C9 and 650E2 hybridoma cell lines, wherein the sFv-encoding sequence is fused to a nucleotide sequence encoding a polypeptide hinge region which, in turn, is fused to a nucleotide sequence encoding a polypeptide derived from the ζ chain of a T-cell receptor complex using methods described in the art. See e.g., Moritz, et al. (1994) *Proc. Natl. Acad. Sci. USA* 91:4318–4322. The subject chimera confers an antigen-specific immunological binding function on the ζ chain of the T cell receptor complex, thereby circumventing major histocompatibility complex (MHC)-restricted antigen recognition. The subject nucleic acid molecule can be transferred into cytotoxic T-cells using retroviral and other gene transfer techniques as described above.

In yet a further embodiment, the third polypeptide domain comprises an amino acid sequence capable of covalently or non-covalently associating with a detectable moiety. In this regard, the third polypeptide domain can be designed to enable the attachment of a detectable moiety such as, but not limited to, radioactive isotopes, fluorescers, chemiluminescers, enzymes, enzyme substrates, enzyme cofactors, enzyme inhibitors, dyes, and metal ions using chemical attachment techniques known in the art.

In one particular embodiment, the third polypeptide domain includes a site which can be labelled with radioisotopes such as Iodine-131, Indium-111, and Technetium-99m, for example. Beta emitters such as Technetium-99m and Indium-111 are preferred because they are detectable with a gamma camera and have favorable half-lives for imagining in vivo. The single polypeptide chains can be labelled, for example, with radioactive atoms such as, but not limited to, Yttrium-90. Technetium-99m, or Indium-111 via a conjugated metal chelator (see, e.g., Khaw et al. (1980) *Science* 209:295; U.S. Pat. No. 4,472,509 to Gansow et al.; and U.S. Pat. No. 4,479,930 to Hnatowich), or by other standard means of isotope linkage to proteins known to those with skill in the art.

In another embodiment of the invention, the third polypeptide domain can be designed to include a site capable of attaching a chemotherapeutic agent using immunoconjugate techniques well known in the art. In this regard, conjugation of a number of chemotherapeutic agents to immunoglobulin molecules have been described, including doxorubicin (Yang et al. (1988) *Proc. Natl. Acad. Sci. USA* 85:1189–1193), daunorubicin (Diener et al. (1985) *Science* 231:148–150; Dillman et al. (1988) *Cancer Res.* 48:6097–6102), methotrexate (Uadia et al. (1985) *J Natl Cancer Inst*. 74:29–35; Deguchi et al. (1986) *Cancer Res*. 46:3751–3755), and chlorambucil (Symth et al. (1986) *J Immunol*. 137:3361–3366).

In yet a further related embodiment, the third polypeptide domain comprises an amino acid sequence capable of attaching to, or comprising a toxin such as ricin, abrin, diphtheria toxin and Pseudomonas exotoxin, or an enzymatically active portion (A chains) thereof. See, e.g., U.S. Pat. No. 4,753,894 to Frankel et al.; Nevelle, et al. (1982) *Immunol Rev* 62:75–91; Ross et al. (1980) *European J Biochem* 104; Vitteta et al. (1982) *Immunol Rev* 62:158–183; Raso et al. (1982) *Cancer Res* 42:457–464, and Trowbridge et al. (1981) *Nature* 294:171–173.

Thus, in one particular embodiment, a toxin is attached to the sFv-encoding nucleic acid molecule using methods known in the art. More particularly the toxin comprises ricin, an enzyme from the castor bean that is highly toxic, or a portion of ricin that confers toxicity. At concentrations as low as 1 ng/ml ricin efficiently inhibits the growth of cells in culture. The ricin A chain has a molecular weight of about 30,000 and is glycosylated. The ricin B chain has a larger size (about,34,000 molecular weight) and is also glycosylated. The B chain contains two galactose binding sites, one in each of the two domains in the folded subunit. The crystallographic structure for ricin shows the backbone tracing of the A chain. There is a cleft, which is probably the active site, that runs diagonally across the molecule. Also present is a mixture of α-helix, β-structure, and irregular structure in the molecule.

The A chain enzymatically inactivates the 60S ribosomal subunit of eukaryotic ribosomes. The B chain binds to galactose-based carbohydrate residues on the surfaces of cells. It appears to be necessary to bind the toxin to the cell surface, and also facilitates and participates in the mechanics of entry of the toxin into the cell. Because all cells have galactose-containing cell surface receptors, ricin inhibits all types of mammalian cells with nearly the same efficiency.

Ricin A chain and ricin B chain are encoded by a gene that specifies both the A and B chains. The polypeptide synthesized from the mRNA transcribed from the gene contains A chain sequences linked to B chain sequences by a 'J' (for joining) peptide. The J peptide fragment is removed by post-translational modification to release the A and B chains. However, A and B chains are still held together by the interchain disulfide bond. The preferred form of ricin is recombinant A chain as it is totally free of B chain and, when expressed in *E. coli*, is unglycosylated and thus cleared from the blood more slowly than the glycosylated form. The specific activity of the recombinant ricin A chain against ribosomes and that of native A chain isolated from castor bean ricin are equivalent. The nucleotide sequence and corresponding amino acid sequence of ricin A chain are known in the art. Roberts et al. (1992) *Targeted Diagn. Therap.* 7:81–97

Recombinant ricin A chain, plant-derived ricin A chain, deglycosylated ricin A chain, or derivatives thereof, can be targeted to a human cancer cell (expressing an antigen selected from the group consisting of HMW mucins bound by 2G3 and 369F10, c-erbB-2 tumor antigen, an approximately 42 kD glycoprotein, an approximately 55 kD glycoprotein, and the approximately 40, 60, 100 and 200 kD antigens bound by 113F1) by the sFv polypeptide of the present invention. To do this, the third polypeptide domain of the sFv molecule can be chemically crosslinked to the ricin A chain form of choice. In one particular embodiment a single-chain Fv-ricin A chain immunotoxin can be formed by fusing the single-chain Fv polypeptide to one or more ricin A chains through the corresponding gene fusion. By replacing the B chain of ricin with an antigen-binding site specific to the P-glycoprotein antigen, the A chain is guided to such antigens on the tumor cell surface. In this way the selective killing of tumor cells expressing these antigens can be achieved. Such target cell selectivity has been demonstrated in many cases against cells grown in culture and generally depends on the presence or absence of antigens on the surface of the cells to which the immunotoxin is directed.

In yet another aspect of the invention, expression cassettes, comprising polynucleotide sequences encoding the sFv polypeptide molecules operably linked to a control sequence that is capable of directing the expression of sFv molecules (and sFv molecules with ancillary polypeptide regions), can be introduced into a suitable host cell for expression using standard gene transfer protocols. The subject polypeptides can thus be expressed in appropriate prokaryotic hosts such as various strains of E. coli, and in eukaryotic hosts such as Chinese hamster ovary cells (CHO), mouse myeloma, hybridoma, transfectoma, and human myeloma cells.

More particularly, the sFv molecules can be expressed in E. coli. The nucleic acid molecule encoding a sFv molecule of interest is first cloned into an expression vector. This can be accomplished by positioning the engineered polynucleotide sequence downstream from a promoter sequence such as Trp or Tac, and a nucleotide sequence coding for a leader polypeptide such as fragment B (FB) of staphylococcal protein A. The resulting expressed fusion protein accumulates in refractile bodies in the cytoplasm of the cells, and may be harvested after disruption of the cells by French press or sonication. The refractile bodies are solubilized, and the expressed fusion molecules are cleaved and refolded by the methods already established for may other recombinant proteins (Huston et al. (1988) Proc. Natl. Acad. Sci. USA 85:5879) or, for direct expression methods, there is no leader and the inclusion bodies may be refolded without cleavage (Huston et al. (1991) Methods in Enzymology 203:46–88).

Further under the invention, subsequent proteolytic cleavage of the isolated sFv from its leader sequence fusions can be performed to yield free sFvs, which can be renatured to obtain an intact biosynthetic, hybrid antigen-binding site. The cleavage site can be immediately adjacent to the sFv polypeptide and include one amino acid or a sequence of amino acids exclusive of any one amino acid or amino acid sequence found in the amino acid structure of the single polypeptide chain.

The cleavage site is designed for specific cleavage by a selected agent. Endopeptidases are preferred, although non-enzymatic (chemical) cleavage agents can be used. Many useful cleavage agents, for instance, cyanogen bromide, dilute acid, trypsin, Staphylococcus aureus V-8 protease, post-proline cleaving enzyme, blood coagulation Factor Xa, enterokinase, andrenin, recognize and preferentially or exclusively cleave-at particular cleavage sites. One particularly preferred peptide sequence cleavage agent is V-8 protease, and the preferred cleavage site is at a Glu residue. Other useful enzymes recognize multiple residues as a cleavage site, e.g., factor Xa (Ile-Glu-Gly-Arg)(SEQ ID NO: 32), or enterokinase (Asp-Asp-Asp-Asp-Lys)(SEQ ID NO: 33). Dilute acid preferentially leaves the peptide bond between Asp-Pro residues, and CNBr in acid cleaves after Met, unless it is followed by Tyr.

In a related embodiment, the subject sFv molecules can be expressed in eukaryotic hybridoma cells. The nucleic acid molecule is first inserted into an expression vector containing, for example, the immunoglobulin promoter, a secretion signal, immunoglobulin enhancers, and various introns. The resultant vector can also contain sequences encoding an ancillary polypeptide such as described above. The vector is then transfected into myeloma cells via established electroporation or protoplast fusion methods. Transfected host cells thus express $V_H$-linker-$V_H$ or $V_L$-linker-$V_H$ sFv polypeptides, each of which may be attached in the various ways discussed above to a protein domain having another function (e.g., cytotoxicity).

It is to be understood that while the invention has been described in conjunction with specific embodi-ments thereof, that the description above is intended to illustrate and not limit the scope of the invention. Other aspects, advantages and modifications within the scope of the invention will be apparent to those skilled in the art to which the invention pertains.

Deposits of Strains Useful in Practicing the Invention

A deposit of biologically pure cultures of the following strains was made with the American Type Culture Collection (ATCC), 10801 University Boulevard, Manassa, Va. 20110-2209, U.S.A. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 USC §122 and the Commissioner's rules pursuant thereto (including 37 CFR §1.12).

These deposits are provided merely as convenience to those of skill in the art, and are not an admission that a deposit is required under 35 USC §112. The nucleic acid sequences of these hybridomas, as well as the amino acid sequences of the polypeptides encoded thereby, are incorporated herein by reference and are controlling in the event of any conflict with the description herein. A license may be required to make, use, or sell the deposited materials, and no such license is hereby granted.

| Hybridoma/Antibody Designation | Deposit Date | ATCC No. |
|---|---|---|
| 2G3 | January 27, 1984 | HB8491 |
| 33F8 | January 9, 1985 | HB8697 |
| 113F1 | January 27, 1984 | HB8489 |
| 260F9 | January 27, 1984 | HB8488 |
| 260F9-1C9* | November 7, 1984 | HB8662 |
| 317G5 | January 27, 1984 | HB8485 |
| 369F10 | December 23, 1984 | HB8682 |
| 520C9 | January 8, 1985 | HB8696 |
| 650E2 | June 18, 1985 | HB10812 |
| 454C11 | January 27, 1984 | HB8484 |
| 452F2 | June 18, 1985 | HB 10811 |
| 741F8 | June 18, 1985 | HB 10807 |

*This clone is a progeny of 260F9 and was found to be a better antibody producer than 260F9.

I claim:

1. A monoclonal antibody that binds to a human breast cancer antigen that is also bound by monoclonal antibody 454C11 which is produced by the hybridoma deposited with the American Type Culture Collection having Accession No. HB 8484.

2. The monoclonal antibody of claim 1, wherein the monoclonal antibody exhibits strong staining intensity as determined in an immunoassay with three or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

3. The monoclonal antibody of claim 2, wherein the monoclonal antibody binds to the extracellular domain of the human breast cancer antigen.

4. The monoclonal antibody of claim 1, wherein the monoclonal antibody exhibits strong staining intensity as determined in an immunoassay with one or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

5. The monoclonal antibody of claim 1, wherein the monoclonal antibody binds to at least one human breast cancer cell line.

6. The monoclonal antibody of claim 5, wherein the human breast cancer cell line is at least one cell line selected from the group consisting of SKBr3 and BT483.

7. The monoclonal antibody of claim 1, wherein the monoclonal antibody binds to the extracellular domain of the human breast cancer antigen.

8. The monoclonal antibody of claim 1, wherein the human breast cancer antigen is c-erbB-2.

9. A monoclonal antibody that binds to a human breast cancer antigen that is also bound by monoclonal antibody 520C9 which is produced by the hybridoma deposited with the American Type Culture Collection having Accession No. HB 8696.

10. The monoclonal antibody of claim 9, wherein the monoclonal antibody exhibits strong staining intensity as determined in an immunoassay with three or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

11. The monoclonal antibody of claim 10, wherein the monoclonal antibody binds to the extracellular domain of the human breast cancer antigen.

12. The monoclonal antibody of claim 9, wherein the monoclonal antibody exhibits strong staining intensity as determined in an immunoassay with one or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

13. The monoclonal antibody of claim 9, wherein the monoclonal antibody binds to at least one human breast cancer cell line.

14. The monoclonal antibody of claim 13, wherein the human breast cancer cell line is at least one cell line selected from the group consisting of SKBr3 and BT483.

15. The monoclonal antibody of claim 9, wherein the monoclonal antibody binds to the extracellular domain of the human breast cancer antigen.

16. The monoclonal antibody of claim 9, wherein the breast cancer antigen is also bound by monoclonal antibody 454C11 which is produced by the hybridoma deposited with the American Type Culture Collection having Accession No. HB 8484.

17. The monoclonal antibody of claim 9, wherein the human breast cancer antigen is also bound by monoclonal antibodies 452F2 and 741F8 which are produced, respectively, by the hybridomas deposited with the American Type Culture Collection having Accession Nos. HB HB110811 and HB10807.

18. The monoclonal antibody of claim 9, wherein the human breast cancer antigen is c-erbB-2.

19. A monoclonal antibody that binds to human c-erbB-2 antigen.

20. The monoclonal antibody of claim 19, wherein the monoclonal antibody exhibits strong staining intensity as determined in an immunoassay with three or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

21. The monoclonal antibody of claim 20, wherein the monoclonal antibody binds to the extracellular domain of human c-erbB-2 antigen.

22. The monoclonal antibody of claim 19, wherein the monoclonal antibody exhibits strong staining intensity as determined in an immunoassay with one or less of the normal tissues and blood cells selected from the group consisting of pancreas, esophagus, lung, kidney, colon, stomach, brain, tonsil, liver, heart, ovary, skin, breast, platelets, red cells, lymphocytes, monocytes and granulocytes.

23. The monoclonal antibody of claim 19, wherein the monoclonal antibody binds to at least one human breast cancer cell line.

24. The monoclonal antibody of claim 23, wherein the human breast cancer cell line is at least one cell line selected from the group consisting of SKBr3 and BT483.

25. The monoclonal antibody of claim 19, wherein the monoclonal antibody binds to the extracellular domain of human c-erbB-2 antigen.

26. The monoclonal antibody of claim 1, prepared by a process comprising:
   (a) providing a hybridoma capable of producing the monoclonal antibody; and
   (b) culturing the hybridoma under conditions that provide for the production of the monoclonal antibody by the hybridoma.

27. The monoclonal antibody of claim 1, prepared by a process comprising:
   (a) providing a hybridoma capable of producing the monoclonal antibody; and
   (b) culturing the hybridoma under conditions that provide for the production of the monoclonal antibody by the hybridoina.

28. The monoclonal antibody of claim 19, prepared by a process comprising:
   (a) providing a hybridoma capable of producing the monoclonal antibody; and
   (b) culturing the hybridoma under conditions that provide for the production of the monoclonal antibody by the hybridoma.

29. A hybridoma that produces the monoclonal antibody of claim 1.

30. A hybridoma that produces the monoclonal antibody of claim 9.

31. A hybridoma that produces the monoclonal antibody of claim 19.

* * * * *

UNITED STATES PATENT AND TRADEMARK OFFICE
CERTIFICATE OF CORRECTION

PATENT NO. : 6,054,561

DATED : April 25, 2000

INVENTOR(S) : Ring, David B.

It is certified that error appears in the above-identified patent and that said Letters Patent is hereby corrected as shown below:

On title page 1, section [75], after "David B. Ring, Palo Alto, Calif.", please insert --Arthur E. Frankel, Winston-Salem, NC--.

On title page 1, section [63], please delete "which is a continuation of application No. 07/190,778, May 8, 1988, Pat. No. 5,169,774,".

On title page 1, section [56], U.S. Patent Documents, please insert
--4,956,453  9/1990   Bjorn et al.--
--5,091,513  2/1992   Huston et al.--
--5,132,405  7/1992   Huston et al.--.

On front page 1, section [56], Other Publications, line 2 of the Verhoeyen et al. citation, please replace "Antilyxozyme" with --Antilysozyme--.

On title page 1, section [56], Other Publications, line 1 of the Cohen et al. citation, please replace "on neu" with --of neu--.

On title page 1, section [56], Other Publications, line 2 of the third Drebin et al. citation, please replace "neu" with --neu--.

On title page 1, section [56], Other Publications, line 3 of the Fendly et al. citation, please replace "HER2/neu" with --HER2/neu--.

On title page 2, section [56], Other Publications, line 1 of the Gullick et al. citation, please replace "c-erbB-2" with --c-erbB-2--.

On title page 2, section [56], Other Publications, line 2 of the Hudziak et al. citation, please replace "In Vitro" with --In Vitro--.

On title page 2, section [56], Other Publications, line 2 of the first Ring et al. citation, please replace "M$_r$" with --M$_r$--.

On title page 2, section [56], Other Publications, line 1 of the Schechter et al. citation, please replace "neu" with --neu--, and please replace "erb-B" with --erb-B--; in line 2, please replace "M$_r$"

UNITED STATES PATENT AND TRADEMARK OFFICE

CERTIFICATE OF CORRECTION

Page 2 of 6

PATENT NO. : 6,054,561

DATED : April 25, 2000

INVENTOR(S) : Ring, David B.

It is certified that error appears in the above-identified patent and that said Letters Patent is hereby corrected as shown below:

with --$M_r$--.

In column 1, line 13, please replace "(abondoned)" with --(abandoned)--.

In column 1, line 17, please replace "(abondoned)" with --(abandoned)--.

In column 3, line 18, please replace "(CDRS)" with --(CDRs)--.

In column 10, line 43, please replace "CDRS" with --CDRs--.

In column 10, line 48, please replace ""CDR3"" with --"CDR3,"--.

In column 10, line 66, please replace "CDRS" with --CDRs--.

In column 12, line 50, please replace "im-munologically" with --immunologically--.

In column 13, line 38, please replace "for-example" with --for example--.

In column 17, line 35, please replace "involved;" with --involved:--.

In column 19, Table 1, part 1, please replace

"Tissue
Antibody  Pancreas  Esophagus  Lung  Kidney  Colon  Stomach  Brain  Tonsil"

with the following:

--                            Tissue
Antibody  Pancreas  Esophagus  Lung  Kidney  Colon  Stomach  Brain  Tonsil--.

In column 19, Table 1, part 2, please replace

"           Tissue
Antibody  Liver  Heart  Ovary  Skin  Breast  Bone Marrow  Uterus  Bladder"

with the following:

--           Tissue
Antibody  Liver  Heart  Ovary  Skin  Breast  Bone Marrow  Uterus  Bladder--.

In column 19, Table 1, part 1, after

"650E2        1Ac, I       0   1-2A   2T    2G    0    0    0"

please insert the following:

UNITED STATES PATENT AND TRADEMARK OFFICE

CERTIFICATE OF CORRECTION

Page 3 of 6

PATENT NO. : 6,054,561

DATED : April 25, 2000

INVENTOR(S) : Ring, David B.

It is certified that error appears in the above-identified patent and that said Letters Patent is hereby corrected as shown below:

```
--454C11    1D    1-2E    0   1T    0    0    0    1E--.
    In column 19, Table 1, part 2, after
"650E2       2D    0      0   0     1    0    2G   0"
please insert the following:
--454C11    1D    0      0   1E,H  1E   ND   ND   ND--.
    In column 19, Table 1, line 4 of the legend, after "S =
sepaceous", please replace "St = stroita" with --ST = stroma--.
    In column 20, Table 2, part 1, after
"650E2       1     ND     1   ND    1    ND   ND   0    0"
please insert the following:
--454C11    1     2      0   2     1    1    ND   2    1--.
    In column 20, Table 2, part 2, row 369F10, column MA, please
replace "6" with --0--.
    In column 20, Table 2, part 2, after
"650E2       1     1      1   ND    ND   2    1    2    1"
please insert the following:
--454C11    1     0      0   ND    0    2    0    0    1--.
    In column 21, Table 2, part 3, after
"650E2       1     0      1   1     1    2    1    2    2"
please insert the following:
--454C11    0     1      1   ND    ND   ND   ND   ND   ND--.
    In column 21, Table 3, part 1, after
"650E2       +     +      +   +     +         NT   +"
please insert the following:
--454C11    +     NT     +   +     +         +--.
    In column 21, Table 3, part 2, after
"650E2       NT    -      NT  +     +         NT   +"
please insert the following:
--454C11    +     -      NT  NT    NT        NT   ND--.
```

UNITED STATES PATENT AND TRADEMARK OFFICE
CERTIFICATE OF CORRECTION

Page 4 of 6

PATENT NO. : 6,054,561

DATED : April 25, 2000

INVENTOR(S) : Ring, David B.

It is certified that error appears in the above-identified patent and that said Letters Patent is hereby corrected as shown below:

In column 21, Table 4, part 2, please replace "650EZ" with --650E2--.

In column 23, line 38, please replace "trichioroacetic" with --trichloroacetic--.

In column 25, Table 8, row 2G3, please replace
"2G3　G1　0.8　1　>50　15　>50　ND"
with the following:
--2G3　G1　0.8　1　>50　15　>50　ND*--.

In column 25, Table 8, please replace
"454C11　G2a　6　>20　0.3　30　>50　>50"
with the following:
--454C11　G2a　6　>20　0.3　30　$\geq$50　$\geq$50--.

In column 25, Table 5, after
"520C9　5.0e5　8.2e6　4.1e12"
please insert the following:
--454C11　3.9e5　4.8e7　1.9e13--.

In column 27, line 2, please replace "454C 11" with --454C11--.

In column 27, line 5, please replace "75G5" with --758G5--.

In column 27, line 6, please replace "7611B10" with --761B10--.

In column 27, line 13, please replace "Immunol." with --*Immunol.*--.

In column 27, line 66, please replace "Tag" with --*Taq*--.

In column 27, line 67, please replace "Sequencing®0" with --Sequencing®--.

In column 28, line 8, please replace "Tag" with --*Taq*--.

In column 28, line 9, please replace "901497." with --901497,--.

In column 28, line 13, please replace "Tag" with --*Taq*--.

In column 36, line 13, please replace "Compugenes" with --Compugene®--.

UNITED STATES PATENT AND TRADEMARK OFFICE

CERTIFICATE OF CORRECTION

PATENT NO. : 6,054,561

DATED : April 25, 2000

INVENTOR(S) : Ring, David B.

It is certified that error appears in the above-identified patent and that said Letters Patent is hereby corrected as shown below:

In column 37, line 56, please replace "CDRS" with --CDRs--.
In column 48, line 7, please replace "$V_H$-linker-$V_H$" with --$V_H$-linker-$V_L$--.
In column 48, line 23, please replace "Manassa" with --Manassas--.
In column 79, line 29, Claim 3, after "monoclonal antibody of", please replace "claim 2" with --claim 1--.
In column 79, line 45, Claim 7, after "monoclonal antibody of", please replace "claim 1" with --claim 2--.
In column 80, line 38, Claim 17, after "Accession Nos.", please replace "HBHB110811" with --HB110811--.
In column 80, line 52, Claim 21, after "monoclonal antibody of", please replace "claim 20" with --claim 19--.
In column 81, line 1, Claim 25, after "monoclonal antibody of", please replace "claim 19" with --claim 20--.
In column 81, line 11, Claim 27, after "monoclonal antibody of", please replace "claim 1" with --claim 9--.

In column 8, line 28, please replace "phopholipids" with --phospholipids--.
In column 18, line 36, please replace "know" with --known--.
In column 34, line 54, please replace "dioleoylphoshatidyl" with --dioleoylphosphatidyl--.

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

It is certified that error appears in the above-identified patent and that said Letters Patent is hereby corrected as shown below:

In column 34, line 67, please replace "17:77);" with --17:77;--.
In column 47, line 35, please replace "may" with --many--.

Signed and Sealed this

Sixth Day of March, 2001

NICHOLAS P. GODICI

Attesting Officer     Acting Director of the United States Patent and Trademark Office

UNITED STATES PATENT AND TRADEMARK OFFICE

CERTIFICATE OF CORRECTION

Page 1 of 6

PATENT NO. : 6,054,561

DATED : April 25, 2000

INVENTOR(S) : Ring, David B.

It is certified that error appears in the above-identified patent and that said Letters Patent is hereby corrected as shown below:

On title page 1, section [75], after "David B. Ring, Palo Alto, Calif.", please insert --Arthur E. Frankel, Winston-Salem, NC--.

On title page 1, section [63], please delete "which is a continuation of application No. 07/190,778, May 8, 1988, Pat. No. 5,169,774,".

On title page 1, section [56], U.S. Patent Documents, please insert
--4,956,453  9/1990    Bjorn et al.--
--5,091,513  2/1992    Huston et al.--
--5,132,405  7/1992    Huston et al.--.

On front page 1, section [56], Other Publications, line 2 of the Verhoeyen et al. citation, please replace "Antilyxozyme" with --Antilysozyme--.

On title page 1, section [56], Other Publications, line 1 of the Cohen et al. citation, please replace "on neu" with --of neu--.

On title page 1, section [56], Other Publications, line 2 of the third Drebin et al. citation, please replace "neu" with --neu--.

On title page 1, section [56], Other Publications, line 3 of the Fendly et al. citation, please replace "HER2/neu" with --HER2/neu--.

On title page 2, section [56], Other Publications, line 1 of the Gullick et al. citation, please replace "c-erbB-2" with --c-erbB-2--.

On title page 2, section [56], Other Publications, line 2 of the Hudziak et al. citation, please replace "In Vitro" with --In Vitro--.

On title page 2, section [56], Other Publications, line 2 of the first Ring et al. citation, please replace "M$_r$" with --$M_r$--.

On title page 2, section [56], Other Publications, line 1 of the Schechter et al. citation, please replace "neu" with --neu--, and please replace "erb-B" with --erb-B--; in line 2, please replace "M$_r$"

UNITED STATES PATENT AND TRADEMARK OFFICE

CERTIFICATE OF CORRECTION

Page 2 of 6

PATENT NO. : 6,054,561

DATED : April 25, 2000

INVENTOR(S) : Ring, David B.

It is certified that error appears in the above-identified patent and that said Letters Patent is hereby corrected as shown below:

with --$M_r$--.

In column 1, line 13, please replace "(abondoned)" with --(abandoned)--.

In column 1, line 17, please replace "(abondoned)" with --(abandoned)--.

In column 3, line 18, please replace "(CDRS)" with --(CDRs)--.

In column 10, line 43, please replace "CDRS" with --CDRs--.

In column 10, line 48, please replace ""CDR3"" with --"CDR3,"--.

In column 10, line 66, please replace "CDRS" with --CDRs--.

In column 12, line 50, please replace "im-munologically" with --immunologically--.

In column 13, line 38, please replace "for-example" with --for example--.

In column 17, line 35, please replace "involved;" with --involved:--.

In column 19, Table 1, part 1, please replace
"Tissue
Antibody Pancreas Esophagus Lung Kidney Colon Stomach Brain Tonsil"
with the following:
--                     Tissue
Antibody Pancreas Esophagus Lung Kidney Colon Stomach Brain Tonsil--.

In column 19, Table 1, part 2, please replace
"     Tissue
Antibody Liver Heart Ovary Skin Breast Bone Marrow Uterus Bladder"
with the following:
--               Tissue
Antibody Liver Heart Ovary Skin Breast Bone Marrow Uterus Bladder--.

In column 19, Table 1, part 1, after
"650E2         1Ac, I        0   1-2A   2T   2G   0   0   0"
please insert the following:

UNITED STATES PATENT AND TRADEMARK OFFICE
CERTIFICATE OF CORRECTION

PATENT NO. : 6,054,561

DATED : April 25, 2000

INVENTOR(S) : Ring, David B.

It is certified that error appears in the above-identified patent and that said Letters Patent is hereby corrected as shown below:

```
--454C11    1D    1-2E    0   1T    0     0     0    1E--.
     In column 19, Table 1, part 2, after
"650E2       2D    0      0    0    1     0    2G    0"
please insert the following:
--454C11    1D    0      0    1E,H  1E    ND   ND   ND--.
     In column 19, Table 1, line 4 of the legend, after "S =
sepaceous", please replace "St = stroita" with --ST = stroma--.
     In column 20, Table 2, part 1, after
"650E2        1    ND     1   ND    1    ND   ND    0     0"
please insert the following:
--454C11     1    2      0    2     1     1   ND    2    1--.
     In column 20, Table 2, part 2, row 369F10, column MA, please
replace "6" with --0--.
     In column 20, Table 2, part 2, after
"650E2        1    1      1   ND   ND     2    1    2    1"
please insert the following:
--454C11     1    0      0   ND    0     2    0    0    1--.
     In column 21, Table 2, part 3, after
"650E2        1    0      1    1    1     2    1    2    2"
please insert the following:
--454C11     0    1      1   ND   ND    ND   ND   ND   ND--.
     In column 21, Table 3, part 1, after
"650E2        +    +      +    +    +    NT    +"
please insert the following:
--454C11     +    NT     +    +    +     +    +--.
     In column 21, Table 3, part 2, after
"650E2       NT    -     NT    +    +    NT    +"
please insert the following:
--454C11     +    -     NT   NT   NT    NT   ND--.
```

UNITED STATES PATENT AND TRADEMARK OFFICE
CERTIFICATE OF CORRECTION

PATENT NO. : 6,054,561

DATED : April 25, 2000

INVENTOR(S) : Ring, David B.

It is certified that error appears in the above-identified patent and that said Letters Patent is hereby corrected as shown below:

In column 21, Table 4, part 2, please replace "650EZ" with --650E2--.

In column 23, line 38, please replace "trichioroacetic" with --trichloroacetic--.

In column 25, Table 8, row 2G3, please replace
"2G3    G1    0.8    1    >50    15    >50    ND"
with the following:
--2G3   G1    0.8    1    >50    15    >50    ND*--.

In column 25, Table 8, please replace
"454C11    G2a    6    >20    0.3    30    >50    >50"
with the following:
--454C11   G2a    6    >20    0.3    30    ≥50    ≥50--.

In column 25, Table 5, after
"520C9    5.0e5    8.2e6    4.1e12"
please insert the following:
--454C11    3.9e5    4.8e7    1.9e13--.

In column 27, line 2, please replace "454C 11" with --454C11--.
In column 27, line 5, please replace "75G5" with --758G5--.
In column 27, line 6, please replace "7611B10" with --761B10--.
In column 27, line 13, please replace "Immunol." with --Immunol.--.
In column 27, line 66, please replace "Tag" with --Taq--.
In column 27, line 67, please replace "Sequencing®0" with --Sequencing®--.
In column 28, line 8, please replace "Tag" with --Taq--.
In column 28, line 9, please replace "901497." with --901497,--.
In column 28, line 13, please replace "Tag" with --Taq--.
In column 36, line 13, please replace "Compugenes" with --Compugene®--.

UNITED STATES PATENT AND TRADEMARK OFFICE

CERTIFICATE OF CORRECTION

PATENT NO. : 6,054,561

DATED : April 25, 2000

INVENTOR(S) : Ring, David B.

It is certified that error appears in the above-identified patent and that said Letters Patent is hereby corrected as shown below:

In column 37, line 56, please replace "CDRS" with --CDRs--.
In column 48, line 7, please replace "$V_H$-linker-$V_H$" with --$V_H$-linker-$V_L$--.
In column 48, line 23, please replace "Manassa" with --Manassas--.
In column 79, line 29, Claim 3, after "monoclonal antibody of", please replace "claim 2" with --claim 1--.
In column 79, line 45, Claim 7, after "monoclonal antibody of", please replace "claim 1" with --claim 2--.
In column 80, line 38, Claim 17, after "Accession Nos.", please replace "HBHB110811" with --HB110811--.
In column 80, line 52, Claim 21, after "monoclonal antibody of", please replace "claim 20" with --claim 19--.
In column 81, line 1, Claim 25, after "monoclonal antibody of", please replace "claim 19" with --claim 20--.
In column 81, line 11, Claim 27, after "monoclonal antibody of", please replace "claim 1" with --claim 9--.

In column 8, line 28, please replace "phopholipids" with --phospholipids--.
In column 18, line 36, please replace "know" with --known--.
In column 34, line 54, please replace "dioleoylphoshatidyl" with --dioleoylphosphatidyl--.

UNITED STATES PATENT AND TRADEMARK OFFICE
CERTIFICATE OF CORRECTION

PATENT NO. : 6,054,561
DATED : April 25, 2000
INVENTOR(S) : Ring, David B.

It is certified that error appears in the above-identified patent and that said Letters Patent is hereby corrected as shown below:

In column 34, line 67, please replace "17:77);" with --17:77;--.
In column 47, line 35, please replace "may" with --many--.

This certificate supersedes Certificate of Correction issued March 6, 2001.

Signed and Sealed this

Seventeenth Day of April, 2001

Attest:

NICHOLAS P. GODICI

Attesting Officer            Acting Director of the United States Patent and Trademark Office